United States Patent
Fan et al.

(10) Patent No.: US 11,220,490 B2
(45) Date of Patent: Jan. 11, 2022

(54) UREAS HAVING ANDROGEN RECEPTOR DEGRADATION ACTIVITY AND USES THEREOF

(71) Applicant: ACCUTAR BIOTECHNOLOGY INC., Brooklyn, NY (US)

(72) Inventors: Jie Fan, New York, NY (US); Yimin Qian, Plainsboro, NJ (US); Wei He, Zionsville, IN (US); Ke Liu, Shanghai (CN)

(73) Assignee: Accutar Biotechnology Inc., Brooklyn, NY (US)

( * ) Notice: Subject to any disclaimer, the term of this patent is extended or adjusted under 35 U.S.C. 154(b) by 0 days.

(21) Appl. No.: 17/331,015

(22) Filed: May 26, 2021

(65) Prior Publication Data

US 2021/0300901 A1    Sep. 30, 2021

Related U.S. Application Data

(63) Continuation of application No. 17/028,612, filed on Sep. 22, 2020.

(60) Provisional application No. 62/903,997, filed on Sep. 23, 2019.

(51) Int. Cl.
*C07D 401/14* (2006.01)
*C07D 401/04* (2006.01)

(52) U.S. Cl.
CPC .................. *C07D 401/14* (2013.01)

(58) Field of Classification Search
CPC ..................... C07D 401/14; C07D 401/04
See application file for complete search history.

(56) References Cited

U.S. PATENT DOCUMENTS

| 8,158,653 B2 | 4/2012 | Muller et al. |
| 2004/0010037 A1 | 1/2004 | Taniguchi et al. |
| 2015/0291562 A1 | 10/2015 | Crew et al. |
| 2018/0179183 A1 | 6/2018 | Crew et al. |

FOREIGN PATENT DOCUMENTS

WO    WO 1998/003502 A1    1/1998

OTHER PUBLICATIONS

International Search Report for International Application No. PCT/US2020/051997, dated Dec. 4, 2020.
Written Opinion of the International Search Authority for International Application No. PCT/US2020/051997, dated Dec. 4, 2020.

*Primary Examiner* — Samira J Jean-Louis
(74) *Attorney, Agent, or Firm* — Finnegan, Henderson, Farabow, Garrett & Dunner, LLP

(57) ABSTRACT

The present disclosure relates to novel compounds, pharmaceutical compositions containing such compounds, and their use in prevention and treatment of cancer and related diseases and conditions. In some embodiments, the compounds disclosed herein exhibit androgen receptor degradation activity.

10 Claims, 1 Drawing Sheet

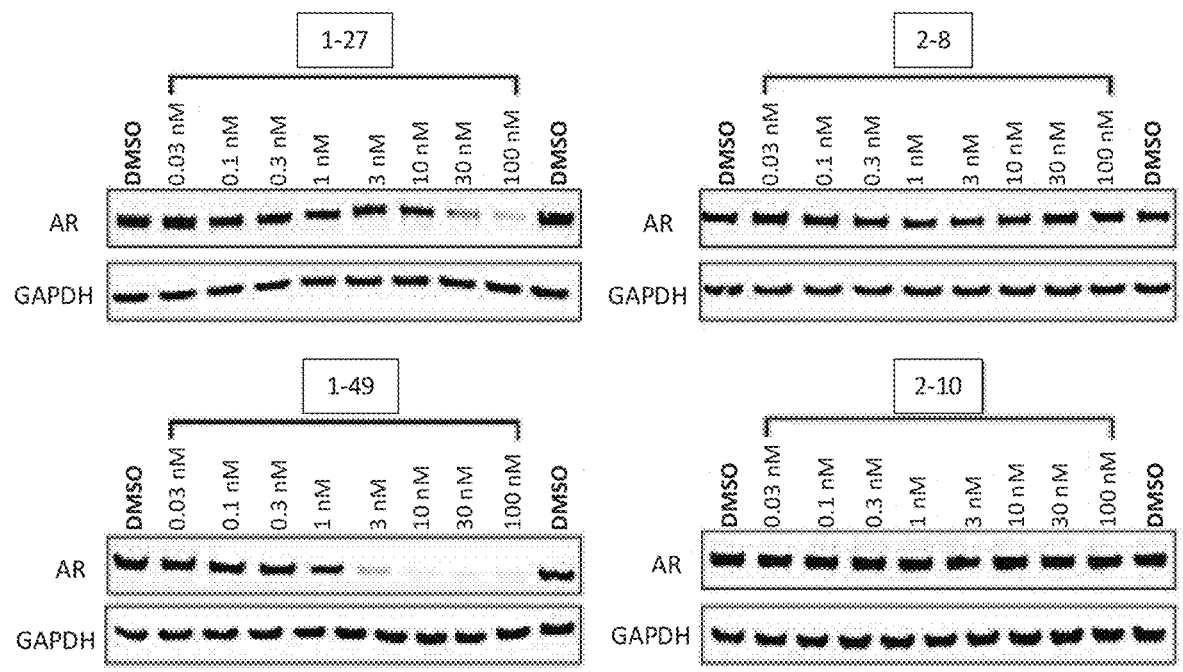

UREAS HAVING ANDROGEN RECEPTOR DEGRADATION ACTIVITY AND USES THEREOF

This application is a continuation of U.S. application Ser. No. 17/028,612, filed Sep. 22, 2020, which claims the benefit of priority to U.S. Provisional Application No. 62/903,997, filed Sep. 23, 2019, which are both hereby incorporated by reference in their entirety.

FIELD OF THE DISCLOSURE

The present disclosure relates to novel compounds, pharmaceutical compositions containing such compounds, and their use in prevention and treatment of diseases and conditions, e.g., cancer. The compounds disclosed herein exhibit androgen receptor degradation activity.

BACKGROUND OF THE DISCLOSURE

Androgens, through binding to the Androgen Receptor (AR), govern a wide range of physiological processes. For example, androgens are required for normal prostate development and function as they are key in the AR signaling pathway. Unfortunately, the AR signaling pathway is also implicated in the development and survival of cancers, such as prostate, breast, and other cancers (see, e.g., "Androgen Receptor in Prostate Cancer", Endocrine Reviews, 2004, 25(2), 276-308; and "Androgen receptors beyond prostate cancer: ann old marker as a new target", Oncotarget, 2014, 6(2), 592-603).

Traditional methods to treat cancers where AR is implicated, such as prostate cancer, involves AR signaling suppression through, for example, androgen deprivation therapy. Such therapy includes chemical and/or surgical castration. Alternatively, anti-androgen therapy may be pursued, whereby a patient is treated with an AR inhibitor, such as enzalutamide (XTANDI®). Although these treatment methods have resulted in improved prognoses for individuals with androgen receptor positive cancer, cancer progression is eventually observed and occurs through, for example, AR gene amplification and/or development of AR mutations.

Accordingly, there exists a need to treat AR positive cancer that halts progression of the cancer, even if the individual has experienced one or more prior therapies. One approach to achieve this goal would be to utilize the naturally occurring cellular ubiquitin-mediated degradation. Without being bound to any theory, it is believed that AR degradation may occur when both AR and a ubiquitin ligase are bound and brought into close proximity.

Cereblon ("CRBN") E3 ubiquitin ligase is a ubiquitin ligase that forms an E3 ubiquitin ligase complex with damaged DNA binding protein 1 and Cullin 4. It functions as a substrate receptor by bringing the substrates to close proximity for ubiquitination and subsequent degradation by proteasomes. Recently, it has been discovered that small molecules drugs, e.g., thalidomide and its close analogs, lenalidomide and pomalidomide, can simultaneously interact with CRBN and some other proteins. In doing so, CRBN may be exploited for target protein degradation, such as IKZF1 and IKZF3. This is thought to account for the anti-myeloma effects of thalidomide and related compounds.

Thus, disclosed herein are compounds useful for the treatment of cancers, such as prostate cancer. In some instances, the cancer is AR positive. The compounds disclosed herein are bifunctional molecules, where one portion of the molecule is capable of interacting with CRBN and the other portion, which is linked to the CRBN-interacting portion of the molecule via a linking moiety, is capable of interacting with AR.

SUMMARY OF THE DISCLOSURE

In some embodiments, the present disclosure is directed to a compound of Formula (1), or a pharmaceutically acceptable salt thereof:

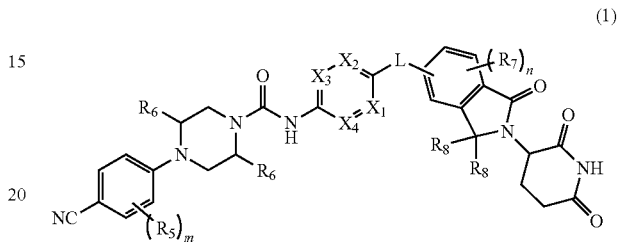

(1)

wherein:
 $X_1$ is $CR_1$ or N;
 $X_2$ is $CR_2$ or N;
 $X_3$ is $CR_3$ or N;
 $X_4$ is $CR_4$ or N;
 each of $R_1$, $R_2$, $R_3$, and $R_4$ is independently selected from hydrogen, halogen, $C_1$-$C_3$alkoxy, and $C_1$-$C_3$haloalkyl, each of which is substituted with 0, 1, 2, or 3 $R_S$;
 each $R_5$ is independently selected from halogen, hydroxyl, $C_1$-$C_3$alkyl, $C_1$-$C_3$alkoxy, $C_1$-$C_3$haloalkyl, —N(R$_9$)$_2$, and —CN, each of which is substituted with 0, 1, 2, or 3 $R_S$;
 each $R_6$ is independently selected from hydrogen, $C_1$-$C_3$alkyl, and $C_1$-$C_3$haloalkyl, each of which is substituted with 0, 1, 2, or 3 $R_S$;
 each $R_7$ is independently selected from halogen, hydroxyl, $C_1$-$C_3$alkyl, $C_1$-$C_3$alkoxy, $C_1$-$C_3$haloalkyl, —N(R$_9$)$_2$, and —CN, each of which is substituted with 0, 1, 2, or 3 $R_S$;
 each $R_8$ is independently selected from hydrogen, hydroxyl, $C_1$-$C_3$alkyl, and $C_1$-$C_3$haloalkyl, each of which is substituted with 0, 1, 2, or 3 $R_S$, or two $R_8$ groups are taken together to form an oxo;
 each $R_9$ is independently selected from hydrogen, $C_1$-$C_3$alkyl, —C(=O)—($C_1$-$C_3$alkyl), —C(=O)—O—($C_1$-$C_3$alkyl), and —C(=O)—NH—($C_1$-$C_3$alkyl), each of which is substituted with 0, 1, 2, or 3 $R_S$, or two $R_9$ groups are taken together to form a 3- to 6-membered heterocycle or heteroaryl;
 each $R_S$ is independently selected from halogen, hydroxyl, $C_1$-$C_3$alkyl, $C_1$-$C_3$alkoxy, $C_1$-$C_3$haloalkyl, —N(R$_9$)$_2$, and —CN;
 L is a linker of 1 to 16 carbon atoms in length, wherein one or more carbon atoms are optionally replaced by C(=O), O, N(R$_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$;
 m is 0, 1, 2, or 3; and
 n is 0, 1, 2, or 3,
 wherein each hydrogen atom is independently and optionally replaced by a deuterium atom.

In some embodiments, the compound of Formula (1) may be a compound of Formula (1A)

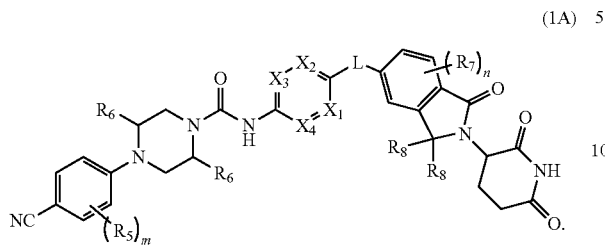

(1A)

In some embodiments, the present disclosure is directed to a compound of Formula (2), or a pharmaceutically acceptable salt thereof:

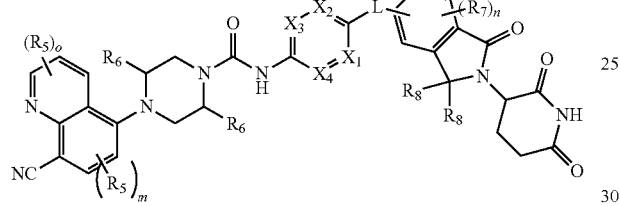

(2)

wherein:
X$_1$ is CR$_1$ or N;
X$_2$ is CR$_2$ or N;
X$_3$ is CR$_3$ or N;
X$_4$ is CR$_4$ or N;
each of R$_1$, R$_2$, R$_3$, and R$_4$ is independently selected from hydrogen, halogen, C$_1$-C$_3$alkoxy, and C$_1$-C$_3$haloalkyl, each of which is substituted with 0, 1, 2, or 3 R$_S$;
each R$_5$ is independently selected from halogen, hydroxyl, C$_1$-C$_3$alkyl, C$_1$-C$_3$alkoxy, C$_1$-C$_3$haloalkyl, —N(R$_9$)$_2$, and —CN, each of which is substituted with 0, 1, 2, or 3 R$_S$;
each R$_6$ is independently selected from hydrogen, C$_1$-C$_3$alkyl, and C$_1$-C$_3$haloalkyl, each of which is substituted with 0, 1, 2, or 3 R$_S$;
each R$_7$ is independently selected from halogen, hydroxyl, C$_1$-C$_3$alkyl, C$_1$-C$_3$alkoxy, C$_1$-C$_3$haloalkyl, —N(R$_9$)$_2$, and —CN, each of which is substituted with 0, 1, 2, or 3 R$_S$;
each R$_8$ is independently selected from hydrogen, hydroxyl, C$_1$-C$_3$alkyl, and C$_1$-C$_3$haloalkyl, each of which is substituted with 0, 1, 2, or 3 R$_S$, or two R$_8$ groups are taken together to form an oxo;
each R$_9$ is independently selected from hydrogen, C$_1$-C$_3$alkyl, —C(=O)—(C$_1$-C$_3$alkyl), —C(=O)—O—(C$_1$-C$_3$alkyl), and —C(=O)—NH—(C$_1$-C$_3$alkyl), each of which is substituted with 0, 1, 2, or 3 R$_S$, or two R$_9$ groups are taken together to form a 3- to 6-membered heterocycle or heteroaryl;
each R$_S$ is independently selected from halogen, hydroxyl, C$_1$-C$_3$alkyl, C$_1$-C$_3$alkoxy, C$_1$-C$_3$haloalkyl, —N(R$_9$)$_2$, and —CN;
L is a linker of 1 to 16 carbon atoms in length, wherein one or more carbon atoms are optionally replaced by C(O), O, N(R$_9$), S, C$_2$-alkenyl, C$_2$-alkynyl, cycloalkyl, aryl, heterocycle, or heteroaryl, wherein the R$_9$, C$_2$-alkenyl, cycloalkyl, aryl, heterocycle, and heteroaryl are each independently substituted with 0, 1, 2, or 3 R$_S$;
m is 0, 1, or 2;
n is 0, 1, 2, or 3; and
o is 0, 1, 2, or 3,
wherein each hydrogen atom is independently and optionally replaced by a deuterium atom.

In some embodiments, the compound of Formula (2) may be a compound of Formula (2A)

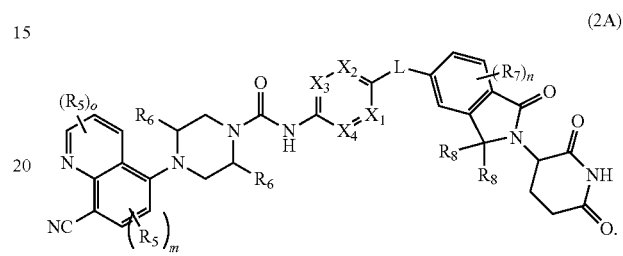

(2A)

In some embodiments, the

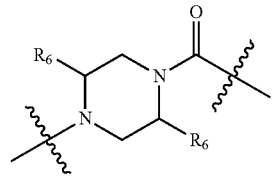

group may be selected from

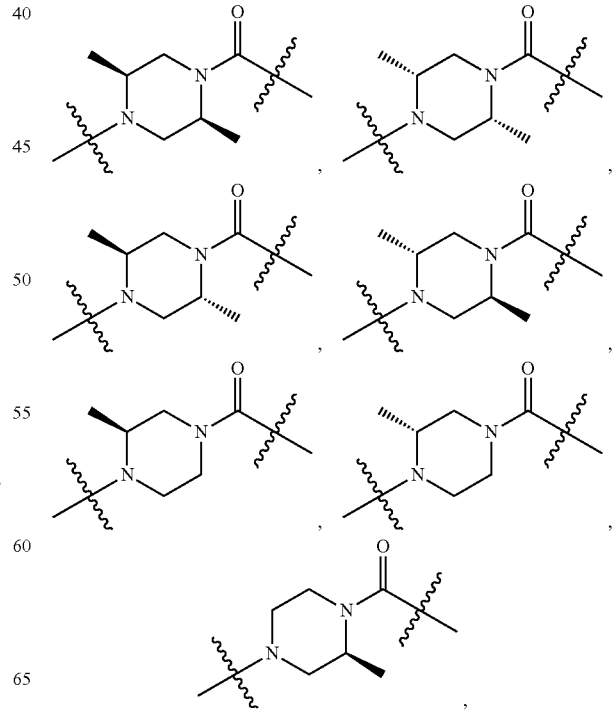

-continued
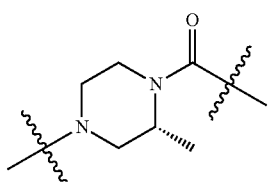
, and
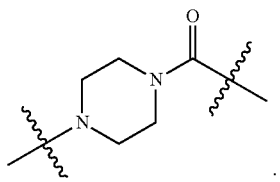
.
In some embodiments, the
group may be selected from
,
In some embodiments, the
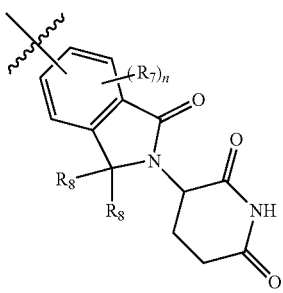
group may be selected from
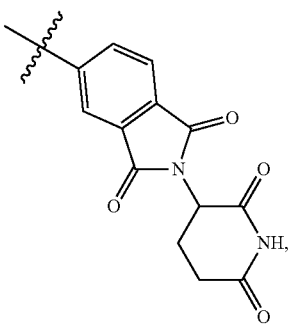
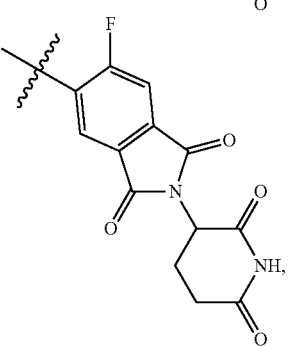
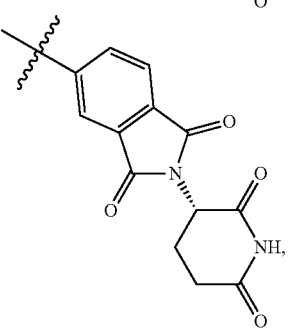
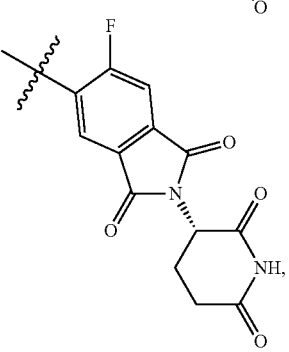

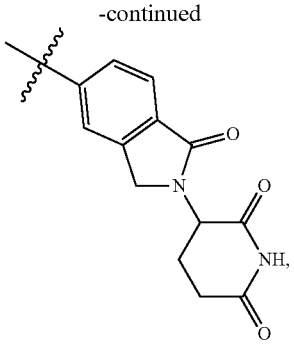
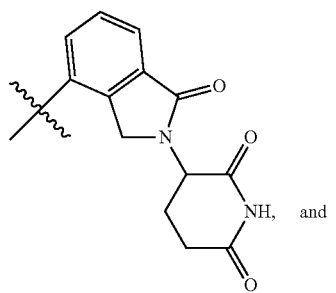
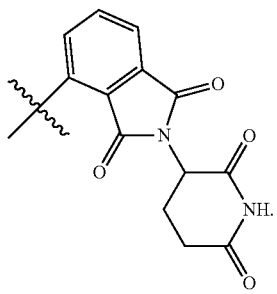 [SMILES: *c1cccc2c1C(=O)N(C1CCC(=O)NC1=O)C2=O]
In some embodiments, L may be selected from:
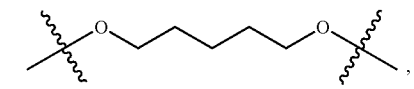
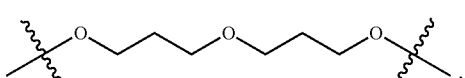
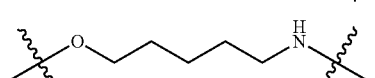
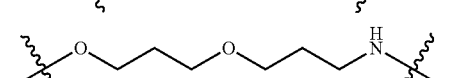
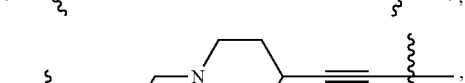
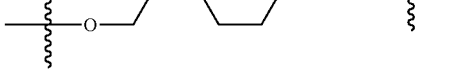
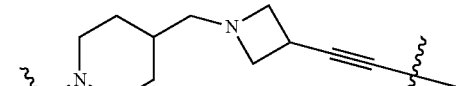
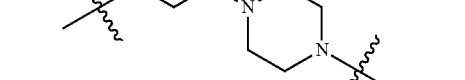
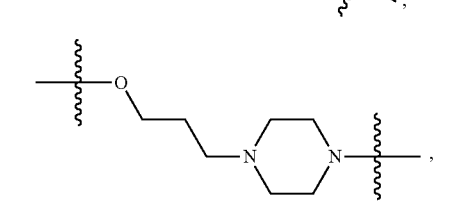

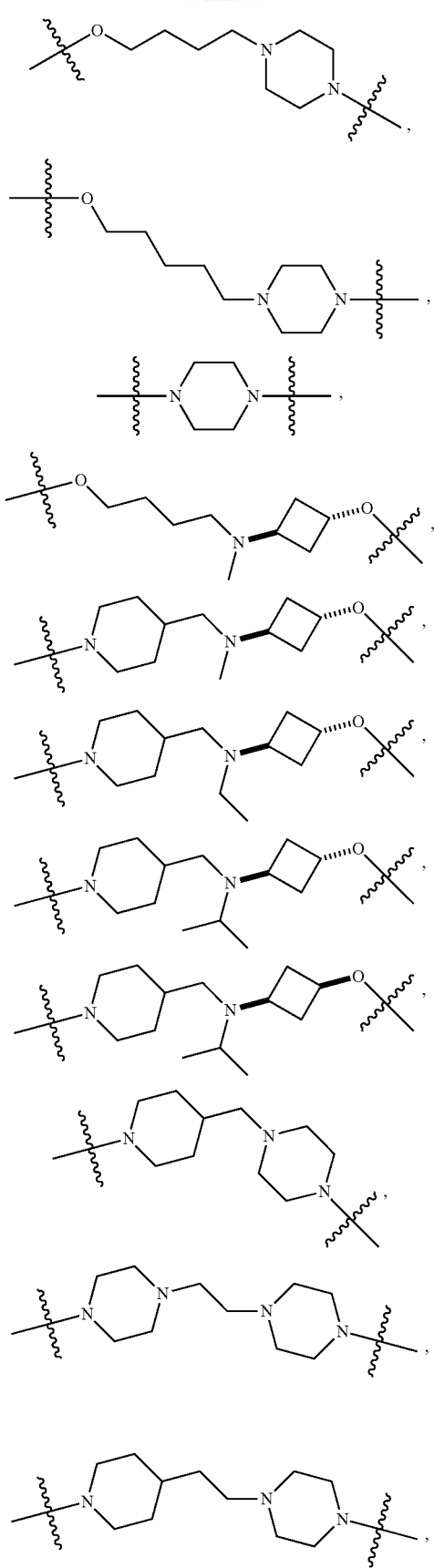

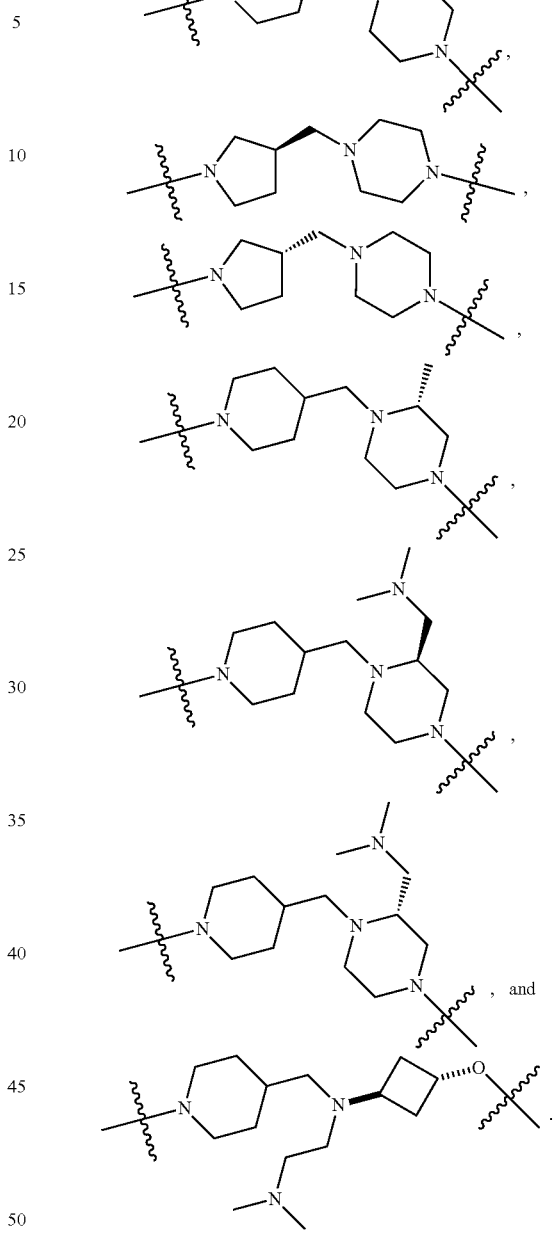

Also disclosed herein is a method of treating cancer, in a subject in need thereof, comprising administering to said subject a compound of Formula (1) (e.g. Formula (1A)) or (2) (e.g. Formula (2A)), or a pharmaceutically acceptable salt thereof, or a pharmaceutical composition comprising a compound of Formula (1) or (2) or a pharmaceutically acceptable salt thereof. In at least one embodiment, the pharmaceutical composition of the present disclosure may be for use in (or in the manufacture of medicaments for) the treatment of cancer in the subject in need thereof.

In at least one embodiment, a therapeutically-effective amount of a pharmaceutical composition of the present disclosure may be administered to a subject diagnosed with cancer. In some embodiments, the cancer is selected from prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer.

BRIEF DESCRIPTION OF THE FIGURES

The accompanying drawings, which are incorporated in and constitute a part of this specification, illustrate the disclosed embodiments and, together with the description, explain the principles of the disclosed embodiments. In the drawings:

FIG. 1 illustrates the androgen receptor (AR) degradative activity of compounds 1-27, 1-49, 2-8, and 2-10 in LNCAP cell lines 24 hours after administration using Western blot analysis.

DETAILED DESCRIPTION OF THE DISCLOSURE

Definitions

As used herein, "cancer" refers to diseases, disorders, and conditions that involve abnormal cell growth with the potential to invade or spread to other parts of the body. Exemplary cancers include, but are not limited to, prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer.

As used herein, the term "androgen receptor positive" means that androgen receptor is detected by one or more analytical methods, e.g., immunohistochemistry. For example, analysis of a biopsy of a subject's tumor may indicate the presence of androgen receptor. AR status may be tested by circulating cancer cells or circulating tumor DNA in a blood test. In some circumstances an AR test may not be performed.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

A dash ("-") that is not between two letters or symbols is used to indicate a point of attachment for a substituent. For example, —CN is attached through the carbon atom.

By "optional" or "optionally" it is meant that the subsequently described event or circumstance may or may not occur, and that the description includes instances where the event or circumstance occurs and instances in which is does not. It will be understood by those skilled in the art, with respect to any group containing one or more substituents, that such groups are not intended to introduce any substitution or substitution patterns that are sterically impractical, synthetically non-feasible and/or inherently unstable.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkenyl" as used herein refers to an unsaturated, two-carbon group having a carbon-carbon double bond, referred to herein as $C_2$-alkenyl.

The term "alkoxy" as used herein refers to an alkyl or cycloalkyl covalently bonded to an oxygen atom.

The term "alkyl" as used herein refers to a saturated straight or branched hydrocarbon, such as a straight or branched group of 1-8 carbon atoms, referred to herein as ($C_1$-$C_8$)alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkynyl" as used herein refers to an unsaturated, two-carbon group having a carbon-carbon triple bond, referred to herein as $C_2$-alkynyl.

The term "aryl" as used herein refers to a mono-, bi-, or other multi-carbocyclic, aromatic ring system with 5 to 14 ring atoms. The aryl group can optionally be fused to one or more rings selected from aryls, cycloalkyls, heteroaryls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include but are not limited to a monocyclic aromatic ring system, wherein the ring comprises 6 carbon atoms, referred to herein as "$C_6$-aryl."

The term "cycloalkyl" as used herein refers to a saturated or unsaturated cyclic, bicyclic, or bridged bicyclic hydrocarbon group of 3-16 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

The term "haloalkyl group" as used herein refers to an alkyl group substituted with one or more halogen atoms.

The term "heteroaryl" as used herein refers to a mono-, bi-, or multi-cyclic, aromatic ring system containing one or more heteroatoms, for example 1-4 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl." In some embodiments, a hetaryl contains 5 to 10 ring atoms, 1 to 4 of which are heteroatoms selected from N, O, and S. In some embodiments, a heteroaryl contains 5 to 8 ring atoms, 1 to 4 of which are heteroatoms selected from N, O, and S.

The terms "heterocycle," "heterocyclyl," or "heterocyclic" as used herein each refer to a saturated or unsaturated 3- to 18-membered ring containing one, two, three, or four heteroatoms independently selected from nitrogen, oxygen, phosphorus, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl. In some embodiments, a heterocycle contains 5 to 10 ring atoms, 1 to 4 of which are heteroatoms selected from N, O, and S. In some embodiments, a heterocycle contains 5 to 8 ring atoms, 1 to 4 of which are heteroatoms selected from N, O, and S.

The terms "hydroxy" and "hydroxyl" as used herein refer to —OH.

The term "oxo" as used herein refers to a double bond to an oxygen atom (i.e., =O). For example, when two geminal groups on a carbon atom are "taken together to form an oxo", then a carbonyl (i.e., C=O) is formed.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. A "free base" form of a compound, for example, does not contain an ionically bonded salt.

The phrase "and pharmaceutically acceptable salts and deuterated derivatives thereof" is used interchangeably with "and pharmaceutically acceptable salts thereof and deuterated derivatives of any of the forgoing" in reference to one or more compounds or formulae of the disclosure. These phrases are intended to encompass pharmaceutically acceptable salts of any one of the referenced compounds, deuterated derivatives of any one of the referenced compounds, and pharmaceutically acceptable salts of those deuterated derivatives.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form.

Suitable pharmaceutically acceptable salts are, for example, those disclosed in S. M. Berge, et al. *J. Pharmaceutical Sciences,* 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Acetate | Iodide | Benzathine |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teoclate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}$ alkyl$)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

As used herein, nomenclature for compounds including organic compounds, can be given using common names, IUPAC, IUBMB, or CAS recommendations for nomenclature. One of skill in the art can readily ascertain the structure of a compound if given a name, either by systemic reduction of compound structure using naming conventions, or by commercially available software, such as CHEMDRAW™ (Cambridgesoft Corporation, U.S.A.).

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "5," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. In some embodiments, an enantiomer or stereoisomer may be provided substantially free of the corresponding enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even if only one tautomeric structure is depicted.

Additionally, unless otherwise stated, structures described herein are also meant to include compounds that differ only in the presence of one or more isotopically enriched atoms. For example, compounds having the present structures except for the replacement of hydrogen by deuterium ($^2$H) or tritium ($^3$H), or the replacement of a carbon by a $^{13}$C- or $^{14}$C-carbon atom are within the scope of this disclosure. Such compounds may be useful as, for example, analytical tools, probes in biological assays, or therapeutic agents.

Compounds

In some embodiments, provided herein are compounds of Formula (1), or a tautomer, stereoisomer, or pharmaceutically acceptable salt thereof, and deuterated derivatives of any of the foregoing:

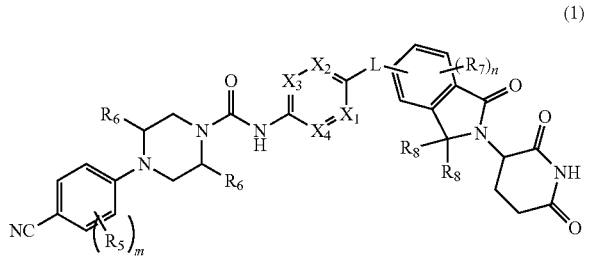

(1)

wherein:
$X_1$ is $CR_1$ or N;
$X_2$ is $CR_2$ or N;
$X_3$ is $CR_3$ or N;
$X_4$ is $CR_4$ or N;
each of $R_1$, $R_2$, $R_3$, and $R_4$ is independently selected from hydrogen, halogen, $C_1$-$C_3$alkoxy, and $C_1$-$C_3$haloalkyl, each of which is substituted with 0, 1, 2, or 3 $R_S$;
each $R_5$ is independently selected from halogen, hydroxyl, $C_1$-$C_3$alkyl, $C_1$-$C_3$alkoxy, $C_1$-$C_3$haloalkyl, —N(R$_9$)$_2$, and —CN, each of which is substituted with 0, 1, 2, or 3 $R_S$;
each $R_6$ is independently selected from hydrogen, $C_1$-$C_3$alkyl, and $C_1$-$C_3$haloalkyl, each of which is substituted with 0, 1, 2, or 3 $R_S$;
each $R_7$ is independently selected from halogen, hydroxyl, $C_1$-$C_3$alkyl, $C_1$-$C_3$alkoxy, $C_1$-$C_3$haloalkyl, —N(R$_9$)$_2$, and —CN, each of which is substituted with 0, 1, 2, or 3 $R_S$;
each $R_8$ is independently selected from hydrogen, hydroxyl, $C_1$-$C_3$alkyl, and $C_1$-$C_3$haloalkyl, each of which is substituted with 0, 1, 2, or 3 $R_S$, or two $R_8$ groups are taken together to form an oxo;
each $R_9$ is independently selected from hydrogen, $C_1$-$C_3$alkyl, —C(=O)—($C_1$-$C_3$alkyl), —C(=O)—O—($C_1$-$C_3$alkyl), and —C(=O)—NH—($C_1$-$C_3$alkyl), each of which is substituted with 0, 1, 2, or 3 $R_S$, or two $R_9$ groups are taken together to form a 3- to 6-membered heterocycle or heteroaryl;
each $R_S$ is independently selected from halogen, hydroxyl, $C_1$-$C_3$alkyl, $C_1$-$C_3$alkoxy, $C_1$-$C_3$haloalkyl, —N(R$_9$)$_2$, and —CN;
L is a linker of 1 to 16 carbon atoms in length, wherein one or more carbon atoms are optionally replaced by C(=O), O, N(R$_9$), S, $C_2$-alkenyl, $C_2$-alkynyl, cycloalkyl, aryl, heterocycle, or heteroaryl, wherein the R$_9$, $C_2$-alkenyl, cycloalkyl, aryl, heterocycle, and heteroaryl are each independently substituted with 0, 1, 2, or 3 $R_S$;
m is 0, 1, 2, or 3; and
n is 0, 1, 2, or 3.

In some embodiments, the compound of Formula (1) may be a compound of Formula (1A)

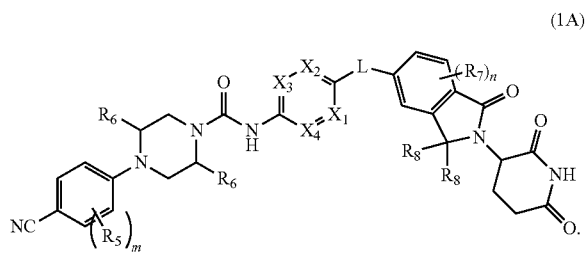

(1A)

In some embodiments, provided herein are compounds of Formula (2), or a tautomer, stereoisomer, or pharmaceutically acceptable salt thereof, and deuterated derivatives of any of the foregoing:

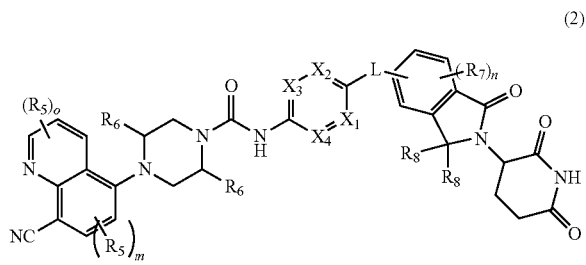

(2)

wherein:
$X_1$ is $CR_1$ or N;
$X_2$ is $CR_2$ or N;
$X_3$ is $CR_3$ or N;
$X_4$ is $CR_4$ or N;
each of $R_1$, $R_2$, $R_3$, and $R_4$ is independently selected from hydrogen, halogen, $C_1$-$C_3$alkoxy, and $C_1$-$C_3$haloalkyl, each of which is substituted with 0, 1, 2, or 3 $R_S$;
each $R_5$ is independently selected from halogen, hydroxyl, $C_1$-$C_3$alkyl, $C_1$-$C_3$alkoxy, $C_1$-$C_3$haloalkyl, —N(R$_9$)$_2$, and —CN, each of which is substituted with 0, 1, 2, or 3 $R_S$;
each $R_6$ is independently selected from hydrogen, $C_1$-$C_3$alkyl, and $C_1$-$C_3$haloalkyl, each of which is substituted with 0, 1, 2, or 3 $R_S$;
each $R_7$ is independently selected from halogen, hydroxyl, $C_1$-$C_3$alkyl, $C_1$-$C_3$alkoxy, $C_1$-$C_3$haloalkyl, —N(R$_9$)$_2$, and —CN, each of which is substituted with 0, 1, 2, or 3 $R_S$;
each $R_8$ is independently selected from hydrogen, hydroxyl, $C_1$-$C_3$alkyl, and $C_1$-$C_3$haloalkyl, each of which is substituted with 0, 1, 2, or 3 $R_S$, or two $R_8$ groups are taken together to form an oxo;
each $R_9$ is independently selected from hydrogen, $C_1$-$C_3$alkyl, —C(=O)—($C_1$-$C_3$alkyl), —C(=O)—O—($C_1$-$C_3$alkyl), and —C(=O)—NH—($C_1$-$C_3$alkyl), each of which is substituted with 0, 1, 2, or 3 $R_S$, or two $R_9$ groups are taken together to form a 3- to 6-membered heterocycle or heteroaryl;

each $R_S$ is independently selected from halogen, hydroxyl, $C_1$-$C_3$alkyl, $C_1$-$C_3$alkoxy, $C_1$-$C_3$haloalkyl, —N($R_9$)$_2$, and —CN;

L is a linker of 1 to 16 carbon atoms in length, wherein one or more carbon atoms are optionally replaced by C(O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$;

m is 0, 1, or 2;
n is 0, 1, 2, or 3; and
o is 0, 1, 2, or 3.

In some embodiments, the compound of Formula (2) may be a compound of Formula (2A)

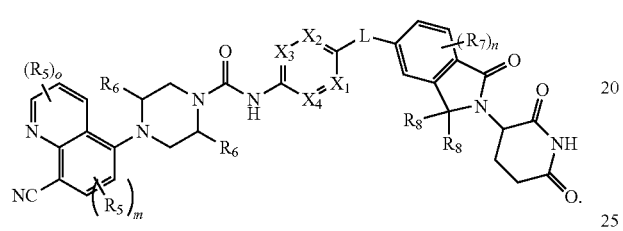

(2A)

In some embodiments, $X_1$ is N. In some embodiments, $X_2$ is N. In some embodiments, $X_1$ and $X_2$ are each N. In some embodiments, $X_2$ is $CR_2$, $X_3$ is $CR_3$, and $X_4$ is $CR_4$. In some embodiments, $R_2$, $R_3$, and $R_4$ are each independently selected from H and F. In some embodiments, $X_2$ is $CR_2$, $X_3$ is $CR_3$, $X_4$ is $CR_4$, and $R_2$, $R_3$, and $R_4$ are each independently selected from H and F. In some embodiments, $X_1$ is $CR_1$, $X_2$ is $CR_2$, $X_3$ is $CR_3$, and $X_4$ is $CR_4$. In some embodiments, $R_1$, $R_2$, $R_3$, and $R_4$ are each independently selected from H and F. In some embodiments, $X_1$ is $CR_1$, $X_2$ is $CR_2$, $X_3$ is $CR_3$, and $X_4$ is $CR_4$, and $R_1$, $R_2$, $R_3$, and $R_4$ are each independently selected from H and F.

In some embodiments, $R_1$ is F. In some embodiments, $R_2$ is F. In some embodiments, $R_3$ is F. In some embodiments, $R_1$ and $R_3$ are each F. In some embodiments, $R_3$ and $R_4$ are each F. In some embodiments, $R_2$, $R_3$, and $R_4$ are each H. In some embodiments, $R_1$, $R_3$, and $R_4$ are each H. In some embodiments, $R_1$, $R_2$, and $R_4$ are each H. In some embodiments, $R_1$, $R_2$, and $R_3$ are each H. In some embodiments, $R_2$ and $R_4$ are each H. In some embodiments, $R_1$ and $R_2$ are each H.

In some embodiments, the

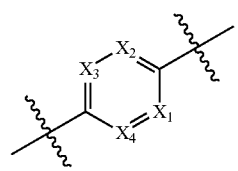

group is selected from

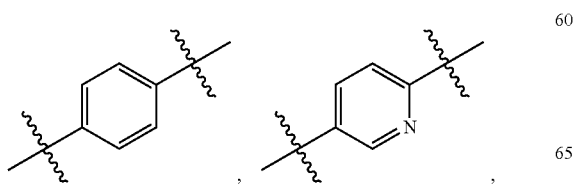

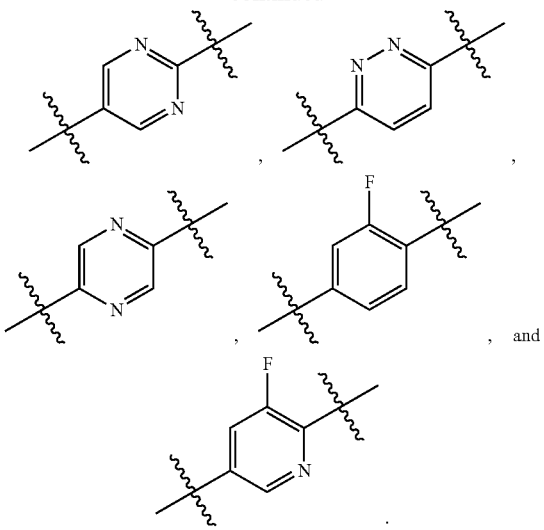

, and

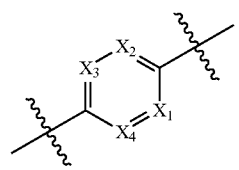

In some embodiments, the group is

In some embodiments, the group is

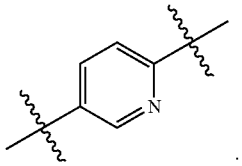 [SMILES: *c1ccc(*)nc1]

In some embodiments, the

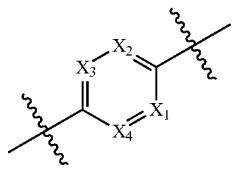

group is

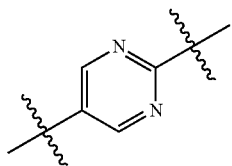

In some embodiments, the

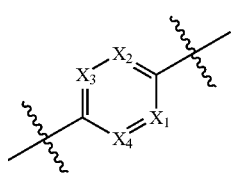

group is

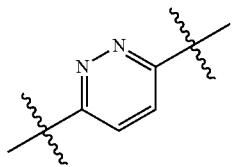

In some embodiments, the

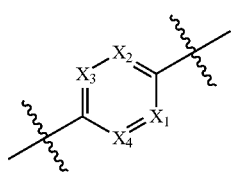

group is

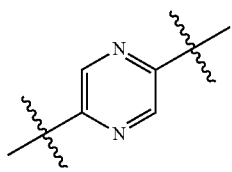

In some embodiments, the

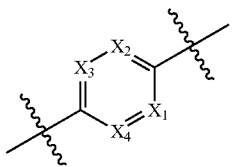

group is

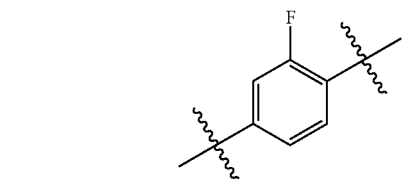

In some embodiments, the

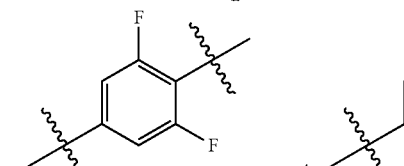

group is

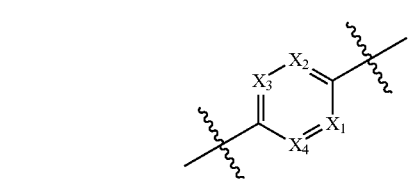

In some embodiments, each $R_5$ is independently selected from halogen, $C_1$-$C_3$alkoxy, and $C_1$-$C_3$haloalkyl. In some embodiments, each $R_5$ is independently selected from —Cl, —OCH$_3$, and —CF$_3$.

In some embodiments, m is 1 or 2. In some embodiments, m is 0. In some embodiments, m is 1. In some embodiments, m is 2.

In some embodiments, o is 0. In some embodiments, o is 1.

In some embodiments, m and o are each 0.

In some embodiments, each $R_6$ is independently selected from H and $C_1$-$C_3$alkyl. In some embodiments, each $R_6$ is independently selected from H and —CH$_3$. In some embodiments, one $R_6$ is H and the other $R_6$ is —CH$_3$. In some embodiments, each $R_6$ is identical. In some embodiments, each $R_6$ is different.

In some embodiments, the group
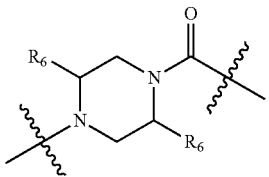
is selected from
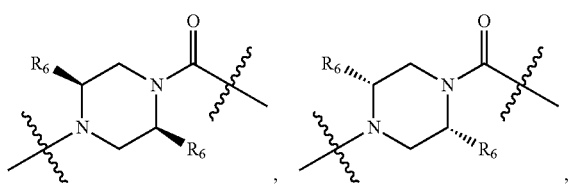
, and
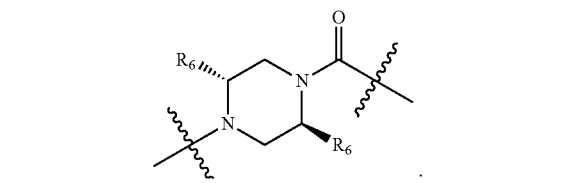
.
In some embodiments, the group
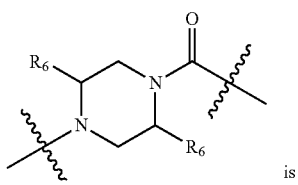
is
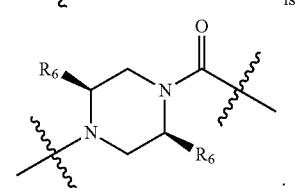
.
In some embodiments, the group
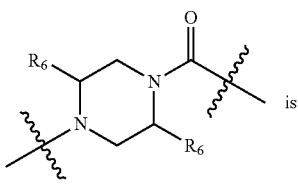
is
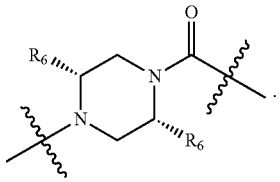
.
In some embodiments, the group
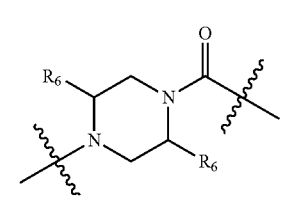
is
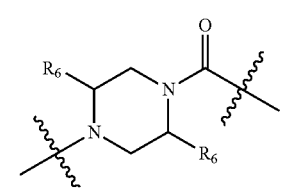
.
In some embodiments, the group
is selected from
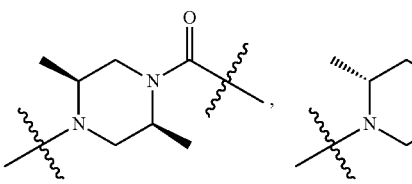 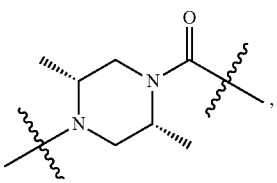

-continued
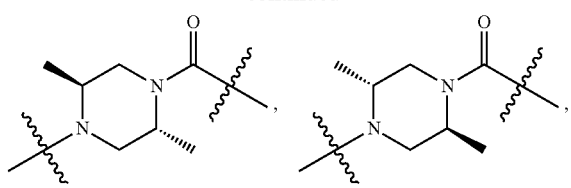
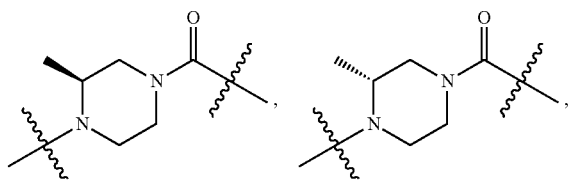
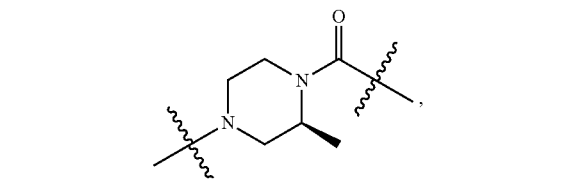
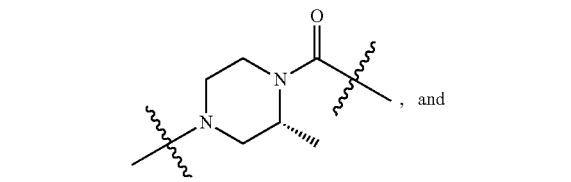
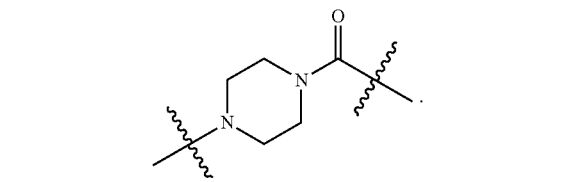
In some embodiments, the group
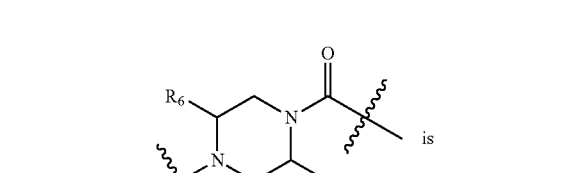
is
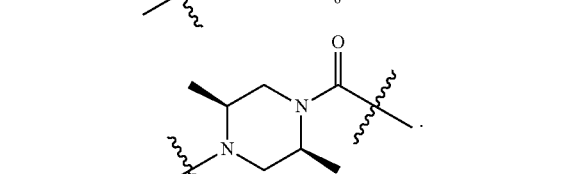
In some embodiments, the group
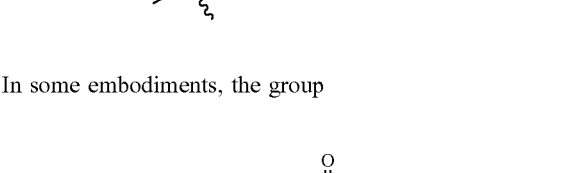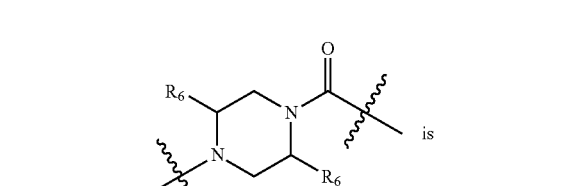
is
-continued
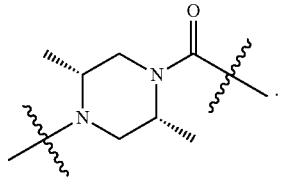
In some embodiments, the group
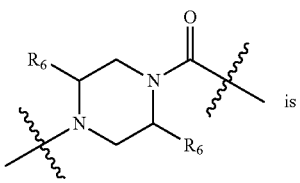
is
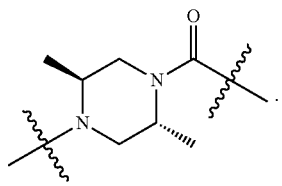
In some embodiments, the group
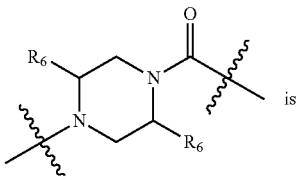
is
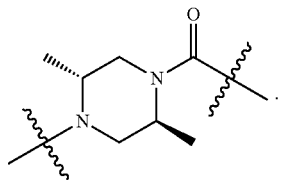
In some embodiments, the group
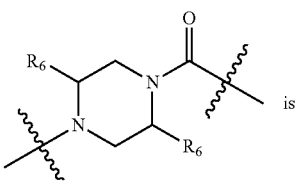
is
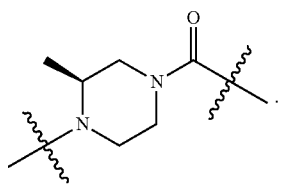

In some embodiments, the group

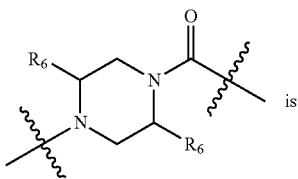 is

In some embodiments, the group

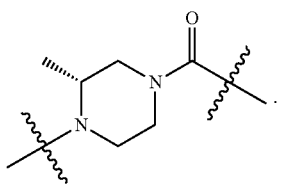.

In some embodiments, the group

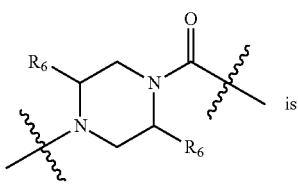 is

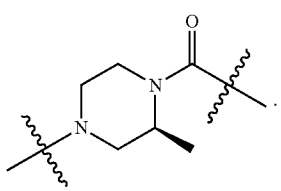.

In some embodiments, the group

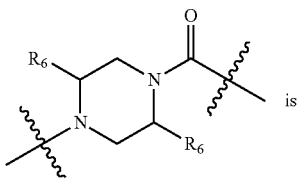 is

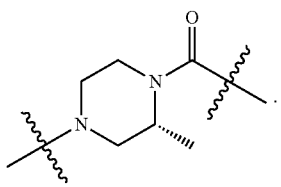.

In some embodiments, the group

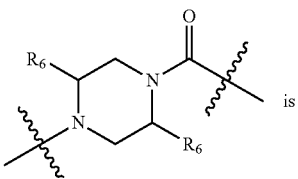 is

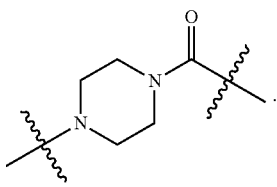.

In some embodiments, each $R_7$ is independently selected from halogen, hydroxyl, $C_1$-$C_3$alkyl, and $C_1$-$C_3$haloalkyl. In some embodiments, each $R_7$ is independently selected from halogen, hydroxyl, —$CH_3$, and —$CF_3$. In some embodiments, each $R_7$ is independently selected from F, hydroxyl, —$CH_3$, and —$CF_3$. In some embodiments, each $R_7$ is independently F.

In some embodiments, n is 0. In some embodiments, n is 1.

In some embodiments, each $R_8$ is hydrogen or two $R_8$ groups are taken together to form an oxo. In some embodiments, each $R_8$ is hydrogen. In some embodiments, two $R_8$ groups are taken together to form an oxo.

In some embodiments, the

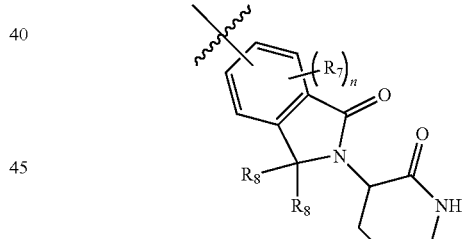

group is

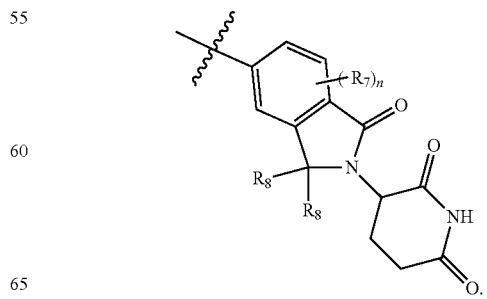

In some embodiments, the group is selected from
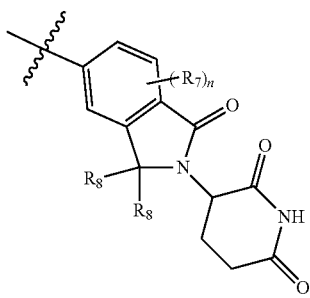
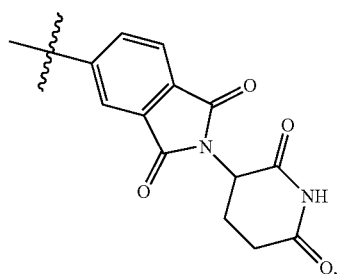
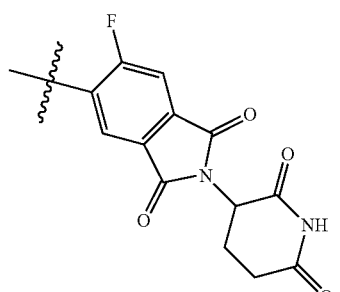
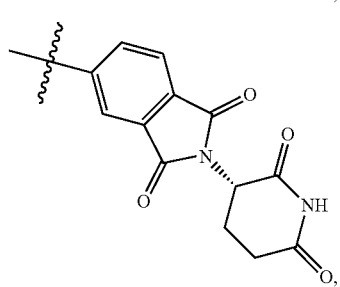 [SMILES: *c1ccc2c(c1)C(=O)N(C1CCC(=O)NC1=O)C2=O]
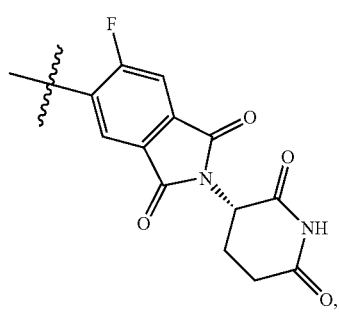
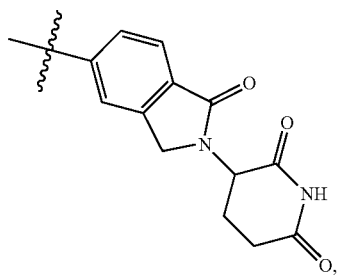
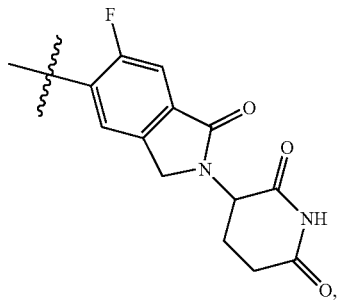
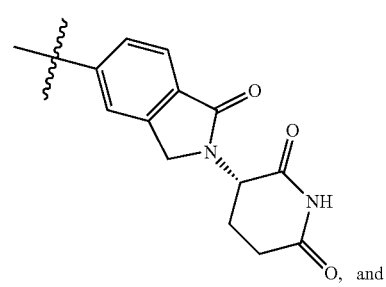
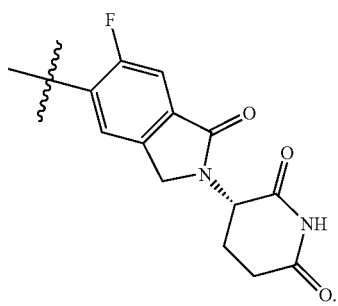
In some embodiments, the
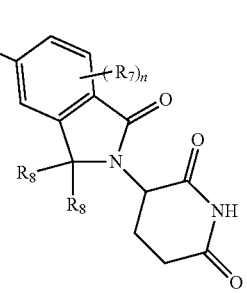

group is
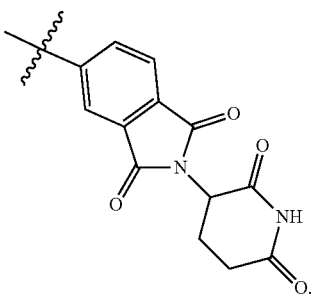 [SMILES: *c1ccc2c(c1)C(=O)N(C1CCC(=O)NC1=O)C2=O]
In some embodiments, the
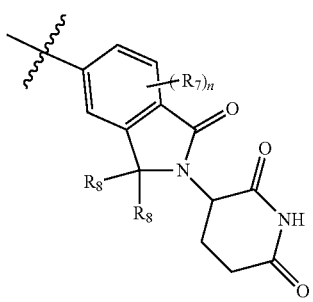
group is
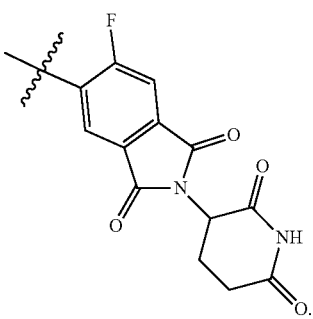
In some embodiments, the
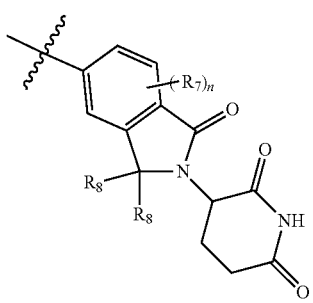
group is
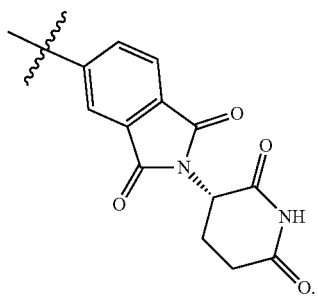 [SMILES: *c1ccc2c(c1)C(=O)N([C@H]1CCC(=O)NC1=O)C2=O]
In some embodiments, the
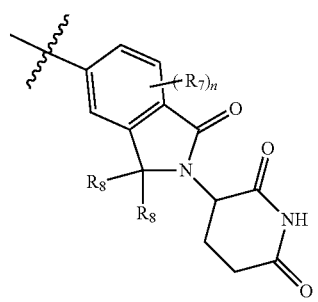
group is
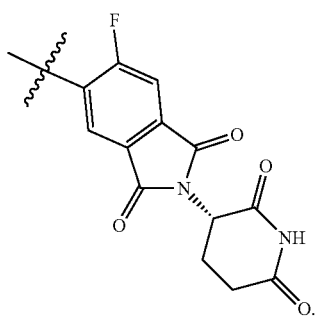 [SMILES: *c1cc2c(cc1F)C(=O)N([C@H]1CCC(=O)NC1=O)C2=O]
In some embodiments, the
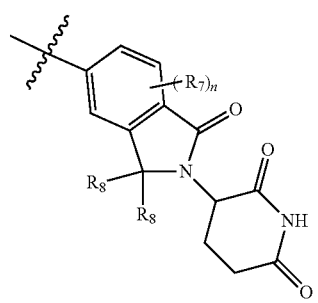

group is
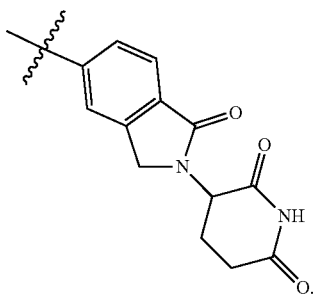 [SMILES: *c1ccc2c(c1)CN(C1CCC(=O)NC1=O)C2=O]
In some embodiments, the
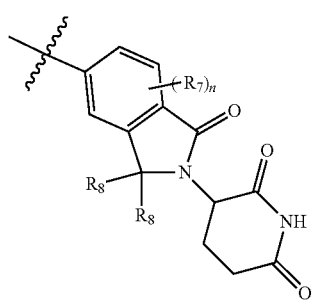
group is
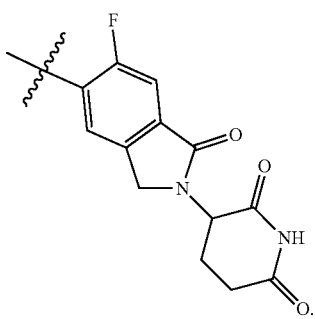 [SMILES: *c1cc2c(cc1F)C(=O)N(C1CCC(=O)NC1=O)C2]
In some embodiments, the
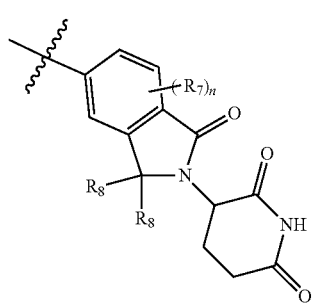
group is
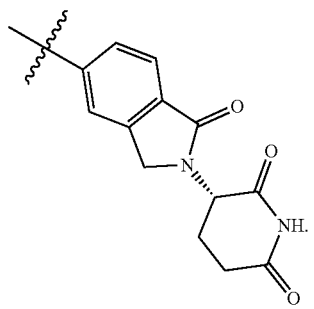 [SMILES: *c1ccc2c(c1)CN([C@H]1CCC(=O)NC1=O)C2=O]
In some embodiments, the
group is
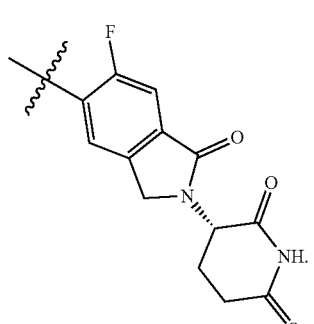
In some embodiments, the
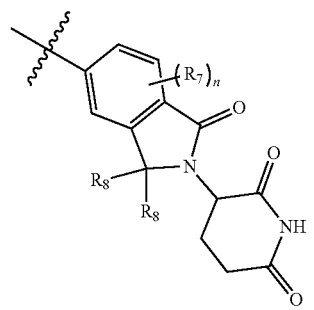

group is
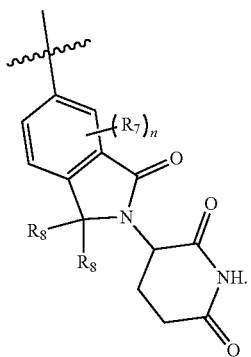
In some embodiments, the
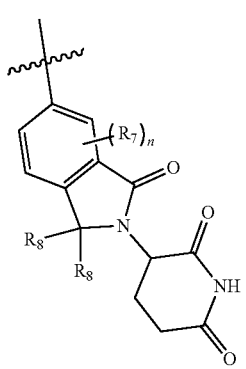
group is
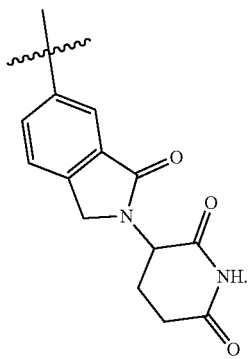 [SMILES: *c1ccc2c(c1)C(=O)N(C1CCC(=O)NC1=O)C2]
In some embodiments, the
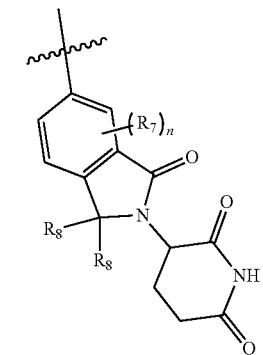
group is
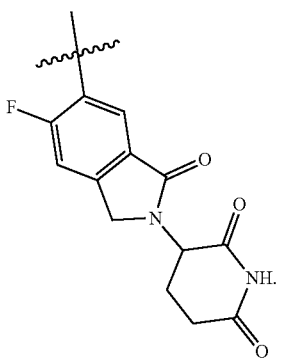 [SMILES: *c1cc2c(cc1F)CN(C1CCC(=O)NC1=O)C2=O]
In some embodiments, the
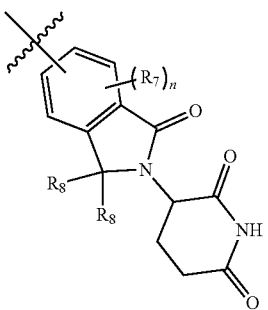
group is
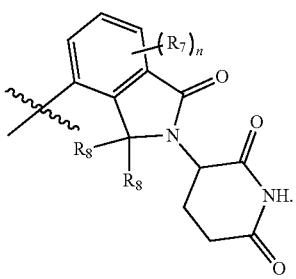

In some embodiments, the

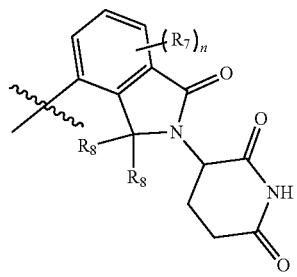

group is

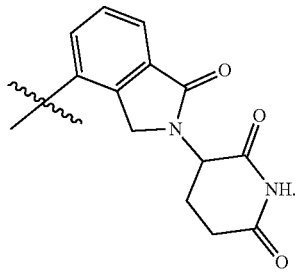

In some embodiments, the

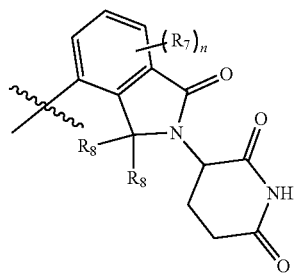

group is

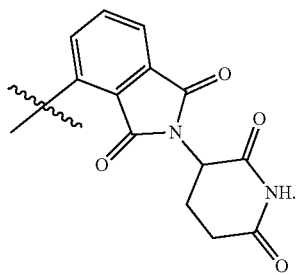 [SMILES: *c1cccc2c1C(=O)N(C1CCC(=O)NC1=O)C2=O]

In some embodiments, each $R_9$ is independently selected from hydrogen, $C_1$-$C_3$alkyl, and —C(=O)—$C_1$-$C_3$alkyl. In some embodiments, each $R_9$ is independently selected from hydrogen and $C_1$-$C_3$alkyl. In some embodiments, each $R_9$ is independently selected from hydrogen, —CH$_3$, —CH$_2$CH$_3$, and —CH(CH$_3$)$_2$.

In some embodiments, L is a linker of 1 to 12 carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$. In some embodiments, L is a linker of 1 to 10 carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$. In some embodiments, L is a linker of 1 to 8 carbon atoms in length, carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$. In some embodiments, L is a linker of 1 to 6 carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 $R_S$.

In some embodiments, one or more carbon atoms of linker L are optionally replaced by C(=O), O, N($R_9$), S, cycloalkyl, aryl, heterocycle, or heteroaryl. In some embodiments, one or more carbon atoms of linker L are optionally replaced by O, N($R_9$), cycloalkyl, or heterocycle, wherein the $R_9$, cycloalkyl, and heterocycle are each independently substituted with 0, 1, 2, or 3 $R_S$.

In some embodiments, the heterocycle in L is selected from piperidine and piperazine, each of which is substituted with 0, 1, 2, or 3 $R_S$. In some embodiments, the heterocycle in L is selected from

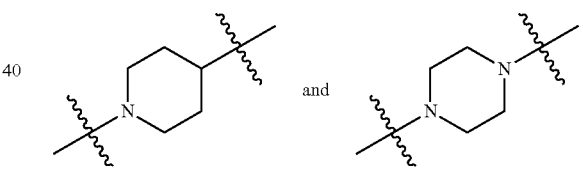

and

In some embodiments, L is selected from:

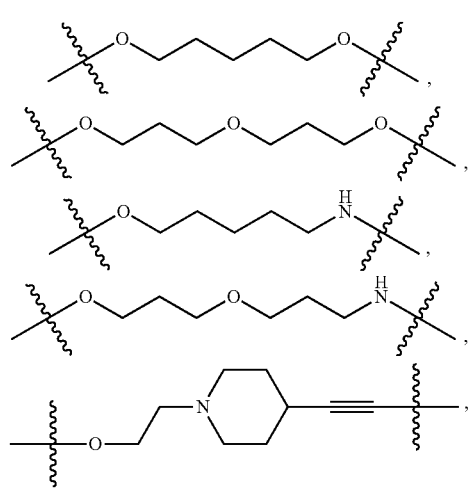

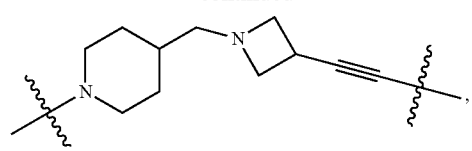
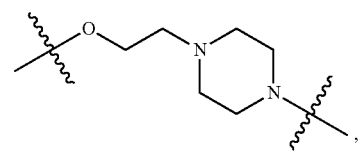
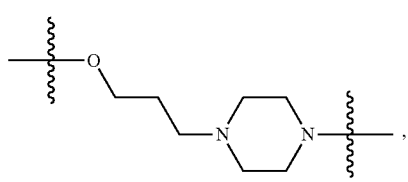
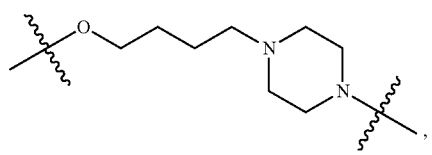
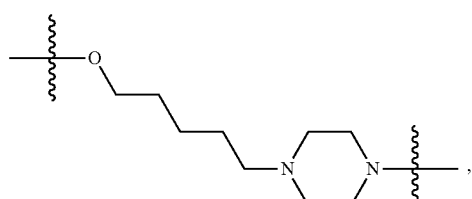
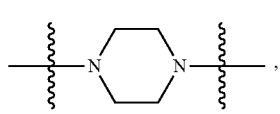
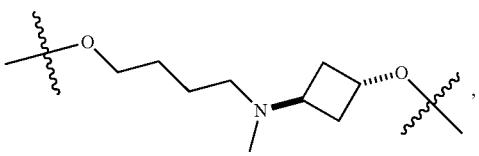
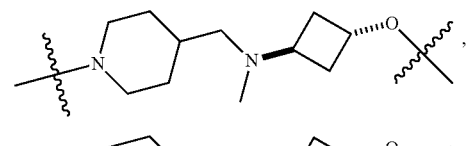
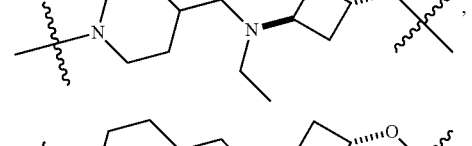
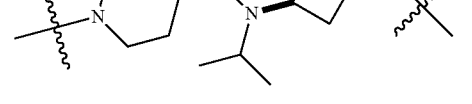
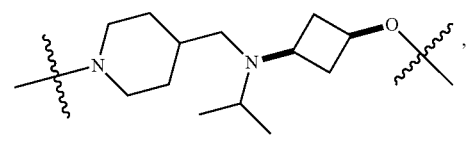
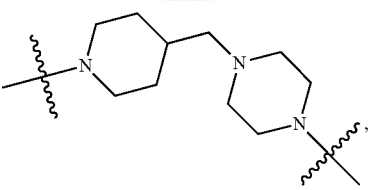
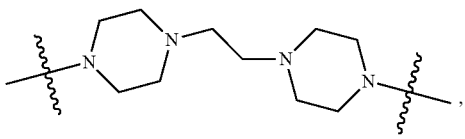
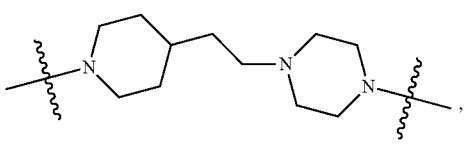
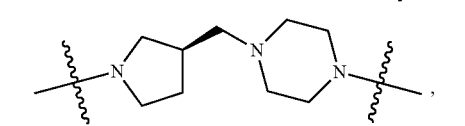
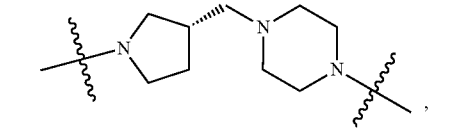
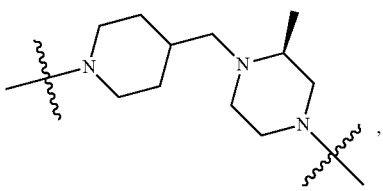
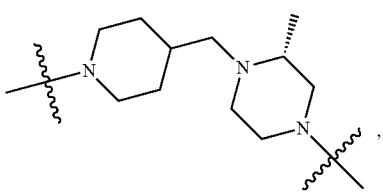
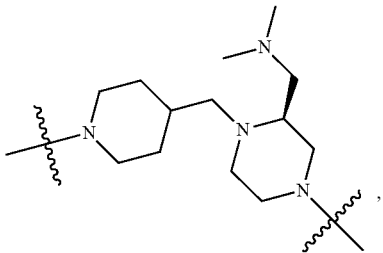
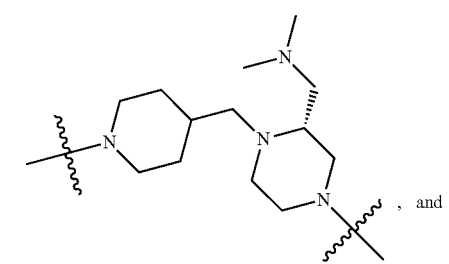
, and -continued

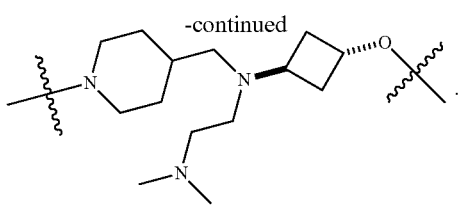

In some embodiments, provided herein is a pharmaceutically acceptable salt of a compound of Formula (1) (e.g. Formula (1A)) or (2) (e.g. Formula (2A)). In some embodiments, provided herein is a deuterated derivative of a pharmaceutically acceptable salt of a compound of Formula (1) or (2). In some embodiments, provided herein is a compound of Formula (1) or (2).

In some embodiments, provided herein is a compound chosen from the compounds listed in Table 2 or a tautomer, stereoisomer, or pharmaceutically acceptable salt thereof, or a deuterated derivative of any of the foregoing.

TABLE 2

Exemplary Compounds of the Present Disclosure

| # | Structure & Name | Reference Number |
|---|---|---|
| 1 | (2R,5S)-4-(3-chloro-4-cyanophenyl)-N-(6-((5-((2-(2,6-dioxopiperidin-3-yl)-1,3-dioxoisoindolin-5-yl)oxy)pentyl)oxy)pyridin-3-yl)-2,5-dimethylpiperazine-1-carboxamide | 1-1 |
| 2 | (2R,5S)-4-(3-chloro-4-cyanophenyl)-N-(6-(3-(3-((2-(2,6-dioxopiperidin-3-yl)-1,3-dioxoisoindolin-5-yl)oxy)propoxy)pyridin-3-yl)-2,5-dimethylpiperazine-1-carboxamide | 1-2 |
| 3 | (2R,5S)-4-(3-chloro-4-cyanophenyl)-N-(6-(2-(4-(2,6-dioxopiperidin-3-yl)-1,3-dioxoisoindolin-5-yl)piperazin-1-yl)ethoxy)pyridin-3-yl)-2,5-dimethylpiperazine-1-carboxamide | 1-3 |
| 4 | (2R,5S)-4-(3-chloro-4-cyanophenyl)-N-(6-(3-(4-(2-(2,6-dioxopiperin-3-yl)-1,3-dioxoisoindolin-5-yl)piperazin-1-yl)propoxy)pyridin-3-yl)-2,5-dimethylpiperazine-1-carboxamide | 1-4 |
| 5 | (2R,5S)-4-(3-chloro-4-cyanophenyl)-N-(6-(4-(4-(2-(2,6-dioxopiperidin-3-yl)-1,3-dioxoisoindolin-5-yl)piperazin-1-yl)butoxy)pyridin-3-yl)-2,5-dimethylpiperazine-1-carboxamide | 1-5 |

TABLE 2-continued

Exemplary Compounds of the Present Disclosure

| # | Structure & Name | Reference Number |
|---|---|---|
| 6 | (2R,5S)-4-(3-chloro-4-cyanophenyl)-N-(6-((5-(4-(2-(2,6-dioxopiperidin-3-yl)-1,3-dioxoisoindolin-5-yl)piperazin-1-yl)pentyl)oxy)pyridin-3-yl)-2,5-dimethylpiperazine-1-carboxamide | 1-6 |
| 7 | (2R,5S)-4-(3-chloro-4-cyanophenyl)-N-(6-(4-(2-(2,6-dioxopiperidin-3-yl)-1,3-dioxoisoindolin-5-yl)piperazin-1-yl)pyridin-3-yl)-2,5-dimethylpiperazine-1-carboxamide | 1-7 |
| 8 | (2R,5S)-4-(3-chloro-4-cyanophenyl)-N-(6-(4-((((1r,3r)-3-((2-(2,6-dioxopiperidin-3-yl)-1,3-dioxoisoindolin-5-yl)oxy)cyclobutyl)(methyl)amino)butoxy)pyridin-3-yl)-2,5-dimethylpiperazine-1-carboxamide | 1-8 |
| 9 | (2R,5S)-4-(3-chloro-4-cyanophenyl)-N-(6-(4-(((((1r,3r)-3-((2-(2,6-dioxopiperidin-3-yl)-1,3-dioxoisoindolin-5-yl)oxy)cyclobutyl)(methyl)amino)methyl)piperidin-1-yl)pyridin-3-yl)-2,5-dimethylpiperazine-1-carboxamide | 1-9 |
| 10 | (2R,5S)-4-(3-chloro-4-cyanophenyl)-N-(6-(4-(((((1r,3r)-3-((2-(2,6-dioxopiperidin-3-yl)-1,3-dioxoisoindolin-5-yl)oxy)cyclobutyl)(ethyl)amino)methyl)piperidin-1-yl)pyridin-3-yl)-2,5-dimethylpiperazine-1-carboxamide | 1-10 |

TABLE 2-continued

Exemplary Compounds of the Present Disclosure

| # | Structure & Name | Reference Number |
|---|---|---|
| 11 | 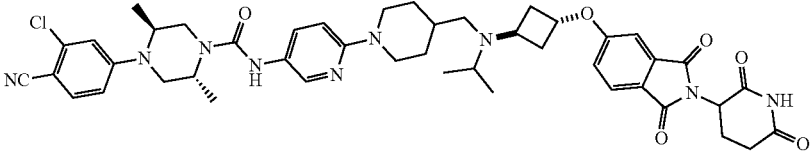<br>(2R,5S)-4-(3-chloro-4-cyanophenyl)-N-(6-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyridin-3-yl)-2,5-dimethylpiperazine-1-carboxamide | 1-11 |
| 12 | 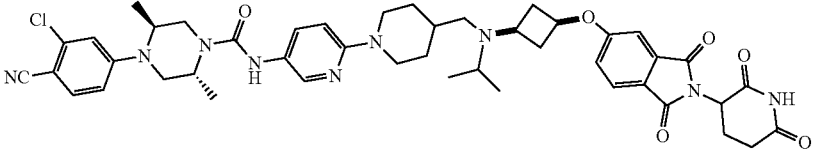<br>(2R,5S)-4-(3-chloro-4-cyanophenyl)-N-(6-(4-((((1s,3s)-3-((2-(2,6-dioxopiperidin-3-yl)-1,3-dioxoisoindolin-5-yl)oxy)cyclobutyl)(isopropyl)amino)methyl)piperidin-1-yl)pyridin-3-yl)-2,5-dimethylpiperazine-1-carboxamide | 1-12 |
| 13 | 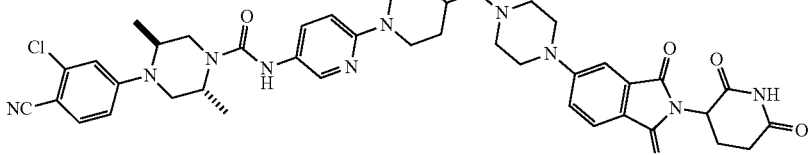<br>(2R,5S)-4-(3-chloro-4-cyanophenyl)-N-(6-(4-((4-(2-(2,6-dioxopiperidin-3-yl)-1,3-dioxoisoindin-5-yl)piperazin-1-yl)methyl)piperidin-1-yl)pyridin-3-yl)-2,5-dimethylpiperazine-1-carboxamide | 1-13 |
| 14 | 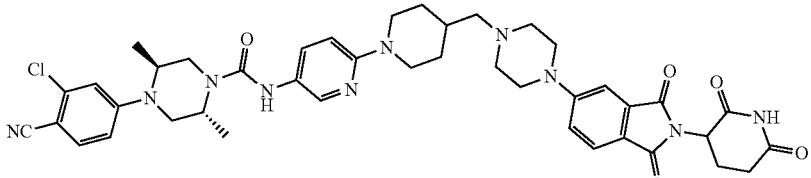<br>(2R,5S)-4-(3-chloro-4-cyanophenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide | 1-14 |
| 15 | 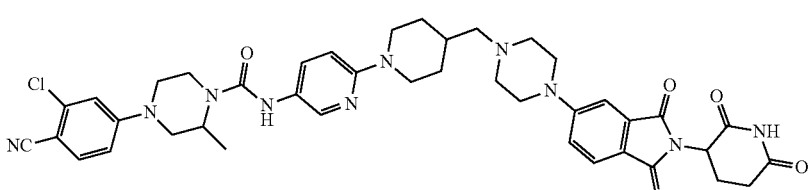<br>4-(3-chloro-4-cyanophenyl)-N-(6-(4-((4-(2-(2,6-dioxopiperidin-3-yl)-1,3-dioxoisoindolin-5-yl)-piperazin-1-yl)methyl)piperidin-1-yl)pyridin-3-yl)-2-methylpiperazine-1-carboxamide | 1-15 |

TABLE 2-continued

Exemplary Compounds of the Present Disclosure

| # | Structure & Name | Reference Number |
|---|---|---|
| 16 | 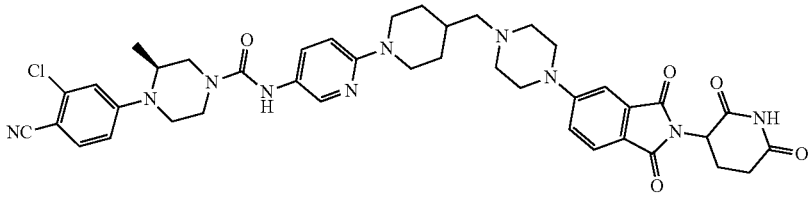<br>(3S)-4-(3-chloro-4-cyanophenyl)-N-(6-(4-((4-(2-(2,6-dioxopiperidin-3-yl)-1,3-dioxoisoindolin-5-yl)-piperazin-1-yl)methyl)piperidin-1-yl)pyridin-3-yl)-3-methylpiperazine-1-carboxamide | 1-16 |
| 17 | 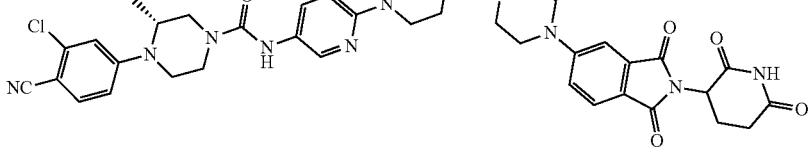<br>(3R)-4-(3-chloro-4-cyanophenyl)-N-(6-(4-((4-(2-(2,6-dioxopiperidin-3-yl)-1,3-dioxoisoindolin-5-yl)-piperazin-1-yl)methyl)piperidin-1-yl)pyridin-3-yl)-3-methylpiperazine-1-carboxamide | 1-17 |
| 18 | 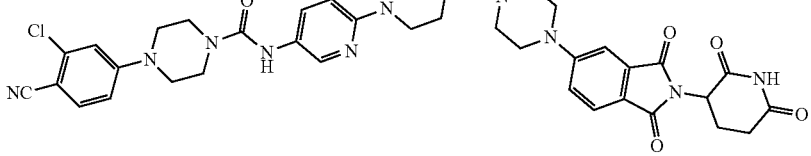<br>4-(3-chloro-4-cyanophenyl)-N-(6-(4-((4-(2-(2,6-dioxopiperidin-3-yl)-1,3-dioxoisoindolin-5-yl)-piperazin-1-yl)methyl)pyridin-3-yl)piperazine-1-carboxamide | 1-18 |
| 19 | 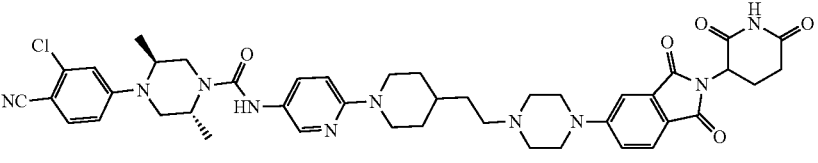<br>(2R,5S)-4-(3-chloro-4-cyanophenyl)-N-(6-(4-(2-(4-(2-(2,6-dioxopiperidin-3-yl)-1,3-dioxoisoindolin-5-yl)piperazin-1-yl)ethyl)piperidin-1-yl)pyridin-3-yl)-2,5-dimethylpiperazine-1-carboxamide | 1-19 |
| 20 | 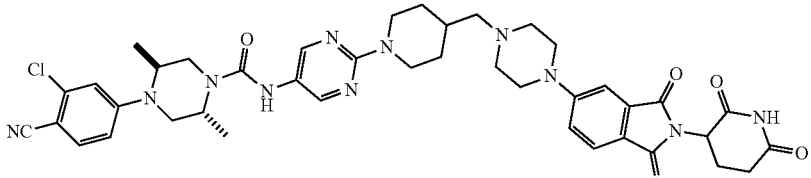<br>(2R,5S)-4-(3-chloro-4-cyanophenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide | 1-20 |

TABLE 2-continued

Exemplary Compounds of the Present Disclosure

| # | Structure & Name | Reference Number |
|---|---|---|
| 21 | 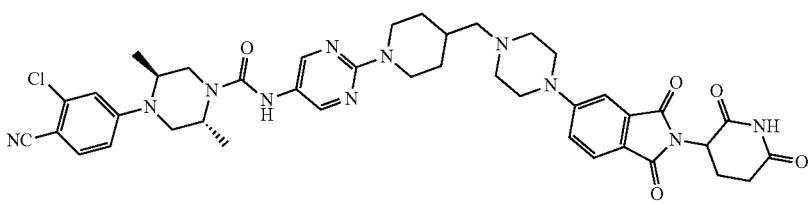<br>(2R,5S)-4-(3-chloro-4-cyanophenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide | 1-21 |
| 22 | 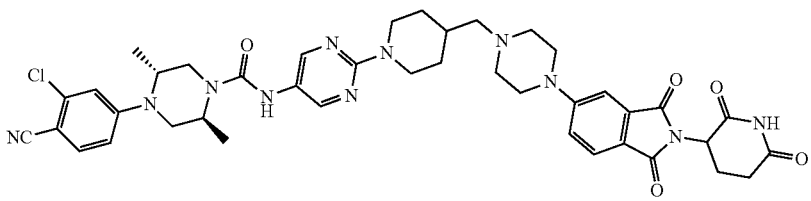<br>(2S,5R)-4-(3-chloro-4-cyanophenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide | 1-22 |
| 23 | 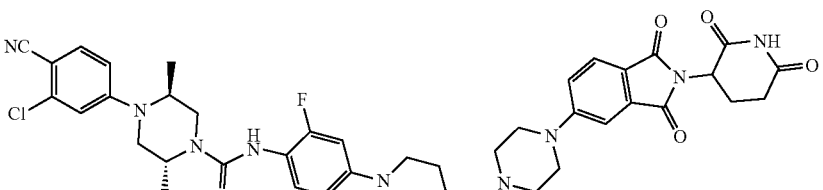<br>(2R,5S)-4-(3-chloro-4-cyanophenyl)-N-(4-(4-((4-(2-(2,6-dioxopiperidin-3-yl)-1,3-dioxoisoindolin-5-yl)-piperazin-1-yl)methyl)piperidin-1-yl)-2-fluorophenyl)-2,5-dimethylpiperazine-1-carboxamide | 1-23 |
| 24 | <br>(2R,5S)-4-(3-chloro-4-cyanophenyl)-N-(4-(4-((4-(2-(2,6-dioxopiperidin-3-yl)-1,3-dioxoisoindolin-5-yl)piperazin-1-yl)methyl)piperidin-1-yl)-2,6-difluorophenyl)-2,5-dimethylpiperazine-1-carboxamide | 1-24 |
| 25 | 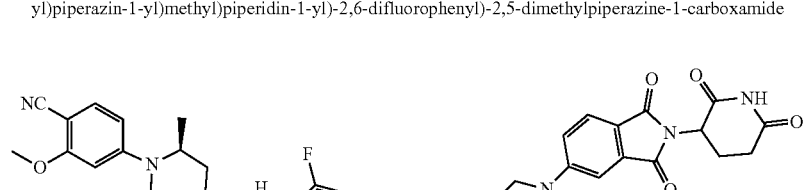<br>(2R,5S)-4-(4-cyano-3-methoxyphenyl)-N-(4-(4-((4-(2-(2,6-dioxopiperidin-3-yl)-1,3-dioxoisoindolin-5-yl)piperazin-1-yl)methyl)piperidin-1-yl)-2-fluorophenyl)-2,5-dimethylpiperazine-1-carboxamide | 1-25 |

TABLE 2-continued

Exemplary Compounds of the Present Disclosure

| # | Structure & Name | Reference Number |
|---|---|---|
| 26 | 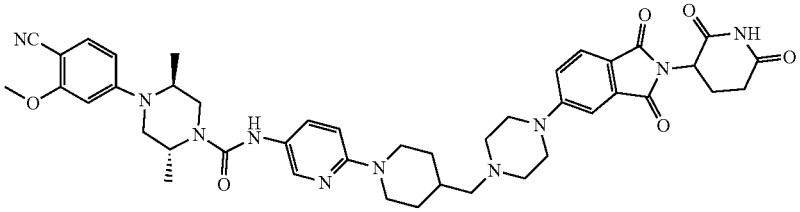<br>(2R,5S)-4-(4-cyano-3-methoxyphenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide | 1-26 |
| 27 | 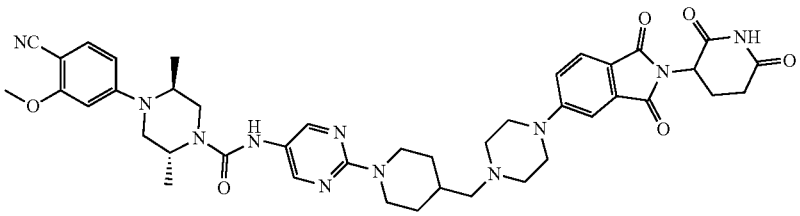<br>(2R,5S)-4-(4-cyano-3-methoxyphenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide | 1-27 |
| 28 | 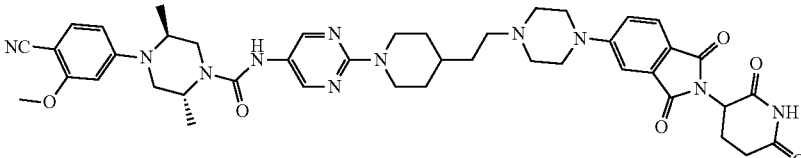<br>(2R,5S)-4-(4-cyano-3-methoxyphenyl)-N-(2-(4-(2-(4-(2-(2,6-dioxopiperidin-3-yl)-1,3-dioxoisoindolin-5-yl)piperazin-1-yl)ethyl)piperidin-1-yl)pyrimidin-5-yl)-2,5-dimethylpiperazine-1-carboxamide | 1-28 |
| 29 | 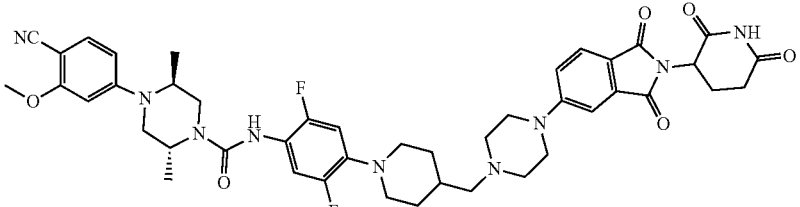<br>(2R,5S)-4-(4-cyano-3-methoxyphenyl)-N-(4-(4-((4-(2-(2,6-dioxopiperidin-3-yl)-1,3-dioxoisoindolin-5-yl)piperazin-1-yl)methyl)piperidin-1-yl)-2,5-difluorophenyl)-2,5-dimethylpiperazine-1-carboxamide | 1-29 |
| 30 | 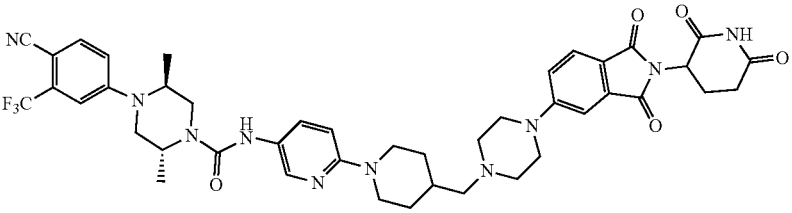<br>(2R,5S)-4-(4-cyano-3-(trifluoromethyl)phenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethyl-piperazine-1-carboxamide | 1-30 |

TABLE 2-continued

Exemplary Compounds of the Present Disclosure

| # | Structure & Name | Reference Number |
|---|---|---|
| 31 | (2R,5S)-4-(4-cyano-3-(trifluoromethyl)phenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethyl-piperazine-1-carboxamide | 1-31 |
| 32 | (2R,5S)-4-(4-cyano-3-(trifluoromethyl)phenyl)-N-(6-(4-((4-(2-((S)-2,6-dioxopiperidin-3-yl)-3-oxoisoindolin-5-yl)piperazin-1-yl)methyl)piperidin-1-yl)pyridin-3-yl)-2,5-dimethylpiperazine-1-carboxamide | 1-32 |
| 33 | (2R,5S)-4-(4-cyano-3-methoxyphenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide | 1-33 |
| 34 | (2R,5S)-4-(4-cyano-3-methoxyphenyl)-N-(4-(4-((4-(2-((S)-2,6-dioxopiperidin-3-yl)-1-oxoisoindolin-5-yl)piperazin-1-yl)methyl)piperidin-1-yl)-2,5-difluorophenyl)-2,5-dimethylpiperazine-1-carboxamide | 1-34 |

TABLE 2-continued

Exemplary Compounds of the Present Disclosure

| # | Structure & Name | Reference Number |
|---|---|---|
| 35 | (2R,5S)-4-(3-chloro-4-cyanophenyl)-N-(4-(4-((4-(2-((S)-2,6-dioxopiperidin-3-yl)-1-oxoisoindolin-5-yl)piperazin-1-yl)methyl)piperidin-1-yl)-2,5-difluorophenyl)-2,5-dimethylpiperazine-1-carboxamide | 1-35 |
| 36 | (2R,5S)-4-(4-cyano-3-fluoro-5-methoxyphenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethyl-piperazine-1-carboxamide | 1-36 |
| 37 | (2R,5S)-4-(4-cyano-3-fluoro-5-methoxyphenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide | 1-37 |
| 38 | (2R,5S)-4-(4-cyano-3-fluoro-5-methoxyphenyl)-N-(4-(4-((4-(2-(2,6-dioxopiperidin-3-yl)-1,3-dioxoisoindolin-5-yl)piperazin-1-yl)methyl)piperidin-1-yl)-2,5-difluorophenyl)-2,5-dimethylpiperazine-1-carboxamide | 1-38 |
| 39 | (2R,5S)-4-(4-cyano-3-methoxyphenyl)-N-(6-(4-((4-(2-(2,6-dioxopiperidin-3-yl)-6-fluoro-1,3-dioxoisoindolin-5-yl)piperazin-1-yl)methyl)piperidin-1-yl)pyridin-3-yl)-2,5-dimethyl-piperazine-1-carboxamide | 1-39 |

TABLE 2-continued

Exemplary Compounds of the Present Disclosure

| # | Structure & Name | Reference Number |
|---|---|---|
| 40 | (2R,5S)-4-(4-cyano-3-methoxyphenyl)-N-(6-(4-((4-(2-((S)-2,6-dioxopiperidin-3-yl)-6-fluoro-1-oxoisoindolin-5-yl)piperazin-1-yl)methyl)piperidin-1-yl)pyridin-3-yl)-2,5-dimethylpiperazine-1-carboxamide | 1-40 |
| 41 | (2R,5S)-4-(3-chloro-4-cyanophenyl)-N-(2-(4-((4-(2-(2,6-dioxopiperidin-3-yl)-6-fluoro-1,3-dioxoisoindolin-5-yl)piperazin-1-yl)methyl)piperidin-1-yl)pyrimidin-5-yl)-2,5-dimethyl-piperazine-1-carboxamide | 1-41 |
| 42 | (2R,5S)-4-(3-chloro-4-cyanophenyl)-N-(2-(4-((4-(2-((S)-2,6-dioxopiperidin-3-yl)-6-fluoro-1-oxoisoindolin-5-yl)piperazin-1-yl)methyl)piperidin-1-yl)pyrimidin-5-yl)-2,5-dimethylpiperazine-1-carboxamide | 1-42 |
| 43 | (2R,5S)-4-(4-cyano-3-(trifluoromethyl)phenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide | 1-43 |
| 44 | (2R,5S)-4-(3-chloro-4-cyanophenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide | 1-44 |

TABLE 2-continued

Exemplary Compounds of the Present Disclosure

| # | Structure & Name | Reference Number |
|---|---|---|
| 45 | (2R,5S)-4-(4-cyano-3-(trifluoromethyl)phenyl)-N-(4-(4-((4-(2-(2,6-dioxopiperidin-3-yl)-1,3-dioxoisoindolin-5-yl)piperazin-1-yl)methyl)piperidin-1-yl)-3-fluorophenyl)-2,5-dimethylpiperazine-1-carboxamide | 1-45 |
| 46 | (2R,5S)-4-(3-chloro-4-cyanophenyl)-N-(4-(4-((4-(2-((S)-2,6-dioxopiperidin-3-yl)-1-oxoisoindolin-5-yl)piperazin-1-yl)methyl)piperidin-1-yl)-3-fluorophenyl)-2,5-dimethylpiperazine-1-carboxamide | 1-46 |
| 47 | (2R,5S)-4-(3-chloro-4-cyanophenyl)-N-(4-(4-((4-(2-(2,6-dioxopiperidin-3-yl)-1,3-dioxoisoindolin-5-yl)piperazin-1-yl)methyl)piperidin-1-yl)-3-fluorophenyl)-2,5-dimethylpiperazine-1-carboxamide | 1-47 |
| 48 | (2R,5S)-4-(4-cyano-3-methoxyphenyl)-N-(4-(4-((4-(2-(2,6-dioxopiperidin-3-yl)-1,3-dioxoisoindolin-5-yl)piperazin-1-yl)methyl)piperidin-1-yl)-3-fluorophenyl)-2,5-dimethylpiperazine-1-carboxamide | 1-48 |
| 49 | (2R,5S)-4-(4-cyano-3-(trifluoromethyl)phenyl-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide | 1-49 |

TABLE 2-continued

Exemplary Compounds of the Present Disclosure

| # | Structure & Name | Reference Number |
|---|---|---|
| 50 | 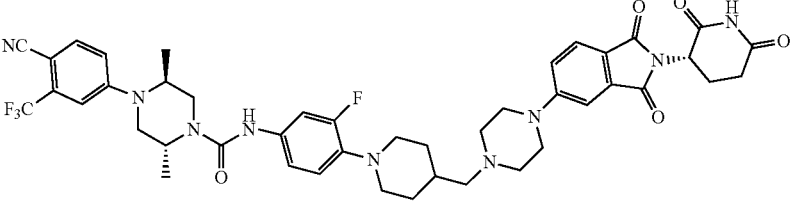<br>(2R,5S)-4-(4-cyano-3-(trifluoromethyl)phenyl)-N-(4-(4-((4-(2-((S)-2,6-dioxopiperidin-3-yl)-1-oxoisoindolin-5-yl)piperazin-1-yl)methyl)piperidin-1-yl)-3-fluorophenyl)-2,5-dimethyl-piperazine-1-carboxamide | 1-50 |
| 51 | 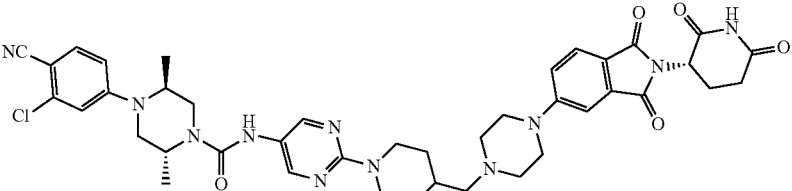<br>(2R,5S)-4-(3-chloro-4-cyanophenyl)-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide | 1-51 |
| 52 | 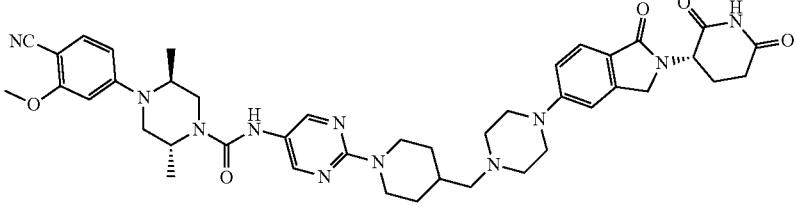<br>(2R,5S)-4-(4-cyano-3-methoxyphenyl)-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide | 1-52 |
| 53 | 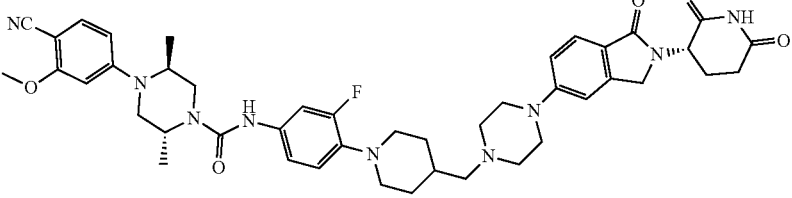<br>(2R,5S)-4-(4-cyano-3-methoxyphenyl)-N-(4-(4-((4-(2-((S)-2,6-dioxopiperidin-3-yl)-1-oxoisoindolin-5-yl)piperazin-1-yl)methyl)piperidin-1-yl)-3-fluorophenyl)-2,5-dimethylpiperazine-1-carboxamide | 1-53 |
| 54 | 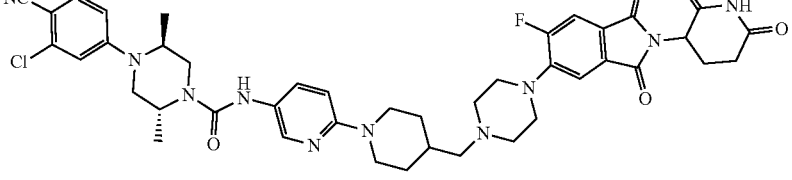<br>(2R,5S)-4-(3-chloro-4-cyanophenyl)-N-(6-(4-((4-(2-(2,6-dioxopiperidin-3-yl)-6-fluoro-1,3-dioxoisoindolin-5-yl)piperazin-1-yl)methyl)piperidin-1-yl)pyridin-3-yl)-2,5-dimethyl-piperazine-1-carboxamide | 1-54 |

TABLE 2-continued

Exemplary Compounds of the Present Disclosure

| # | Structure & Name | Reference Number |
|---|---|---|
| 55 | (2R,5S)-4-(4-cyano-3-methoxyphenyl)-N-(4-(4-((4-(2-((S)-2,6-dioxopiperidin-3-yl)-6-fluoro-1-oxoisoindolin-5-yl)piperazin-1-yl)methyl)piperidin-1-yl)-3-fluorophenyl)-2,5-dimethyl-piperazine-1-carboxamide | 1-55 |
| 56 | (2R,5S)-4-(3-chloro-4-cyanophenyl)-N-(4-(4-((4-(2-((S)-2,6-dioxopiperidin-3-yl)-6-fluoro-1-oxoisoindolin-5-yl)piperazin-1-yl)methyl)piperidin-1-yl)-3-fluorophenyl)-2,5-dimethyl-piperazine-1-carboxamide | 1-56 |

[0030] In some embodiments, provided herein is a compound chosen from the compounds listed in Table 3 or a tautomer, stereoisomer, or pharmaceutically acceptable salt thereof, or a deuterated derivative of any of the foregoing.

TABLE 3

Exemplary Compounds of the Present Disclosure

| # | Structure & Name | Reference Number |
|---|---|---|
| 57 | (2R,5S)-4-(8-cyanoquinolin-5-yl)-N-(6-((5-((2-2,6-dioxopiperidin-3-yl)-1,3-dioxoisoindolin-5-yl)oxy)-pentyl)oxy)pyridin-3-yl)-2,5-dimethylpiperazine-1-carboxamide | 2-1 |
| 58 | (2R,5S)-4-(8-cyanoquinolin-5-yl)-N-(6-(3-(3-((2-(2,6-dioxopiperidin-3-yl)-1,3-dioxoisoindolin-5-yl)oxy)-propoxy)propoxy)pyridin-3-yl)-2,5-dimethylpiperazine-1-carboxamide | 2-2 |
| 59 | (2R,5S)-4-(8-cyanoquinolin-5-yl)-N-(6-(2-(4-(2-(2,6-dioxopiperidin-3-yl)-1,3-dioxoisoindolin-5-yl)-piperazin-1-yl)ethoxy)pyridin-3-yl)-2,5-dimethylpiperazine-1-carboxamide | 2-3 |

TABLE 3-continued

Exemplary Compounds of the Present Disclosure

| # | Structure & Name | Reference Number |
|---|---|---|
| 60 | (2R,5S)-4-(8-cyanoquinolin-5-yl)-N-(6-(3-(4-(2-(2,6-dioxopiperidin-3-yl)-1,3-dioxoisoindolin-5-yl)-piperazin-1-yl)propoxy)pyridin-3-yl)-2,5-dimethylpiperazine-1-carboxamide | 2-4 |
| 61 | (2R,5S)-4-(8-cyanoquinolin-5-yl)-N-(6-(4-(4-(2-(2,6-dioxopiperidin-3-yl)-1,3-dioxoisoindolin-5-yl)-piperazin-1-yl)butoxy)pyridin-3-yl)-2,5-dimethylpiperazine-1-carboxamide | 2-5 |
| 62 | (2R,5S)-4-(8-cyanoquinolin-5-yl)-N-(6-((5-(4-(2-(2,6-dioxopiperidin-3-yl)-1,3-dioxoisoindolin-5-yl)-piperazin-1-yl)pentyl)oxy)pyridin-3-yl)-2,5-dimethylpiperazine-1-carboxamide | 2-6 |
| 63 | (2R,5S)-4-(8-cyanoquinolin-5-yl)-N-(6-(4-(2-(2,6-dioxopiperidin-3-yl)-1,3-dioxoisoindolin-5-yl)-piperazin-1-yl)pyridin-3-yl)-2,5-dimethylpiperazine-1-carboxamide | 2-7 |
| 64 | (2R,5S)-4-(8-cyanoquinolin)-5-yl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide | 2-8 |

TABLE 3-continued

Exemplary Compounds of the Present Disclosure

| # | Structure & Name | Reference Number |
|---|---|---|
| 65 | 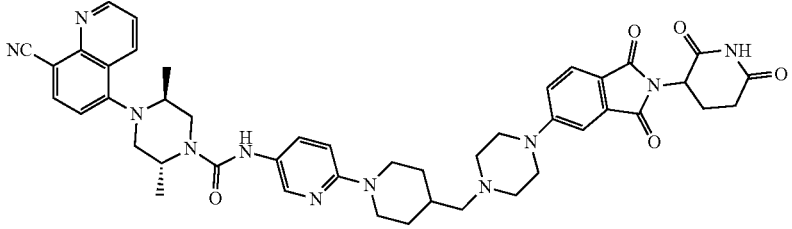 (2R,5S)-4-(8-cyanoquinolin-5-yl)-N-(6-(4-((4-2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide | 2-9 |
| 66 | 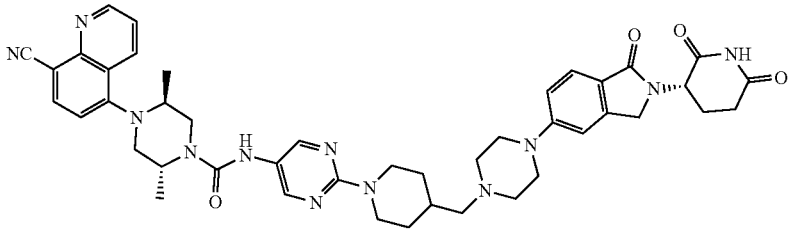 (2R,5S)-4-(8-cyanoquinolin-5-yl)-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide | 2-10 |
| 67 | 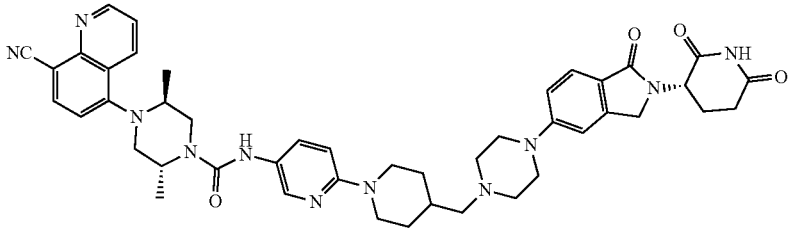 (2R,5S)-4-(8-cyanoquinolin-5-yl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide | 2-11 |
| 68 | 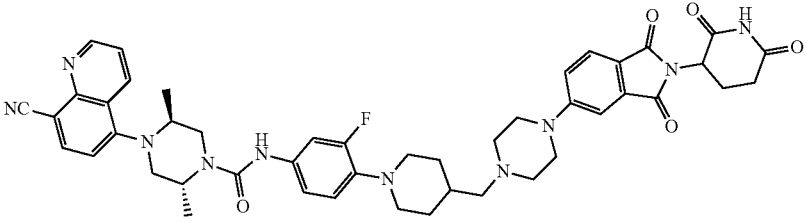 (2R,5S)-4-(8-cyanoquinolin-5-yl)-N-(4-(4-((4-(2-(2,6-dioxopiperidin-3-yl)-1,3-dioxoisoindolin-5-yl)-piperazin-1-yl)methyl)piperidin-1-yl)-3-fluorophenyl)-2,5-dimethylpiperazine-1-carboxamide | 2-12 |

TABLE 3-continued

Exemplary Compounds of the Present Disclosure

| # | Structure & Name | Reference Number |
|---|---|---|
| 69 | (2R,5S)-4-(8-cyanoquinolin-5-yl)-N-(6-(4-((((1r,3r)-3-((2-(2,6-dioxopiperidin-3-yl)-1,3-dioxoiso-indolin-5-yl)oxy)cyclobutyl)(isopropyl)amino)methyl)piperidin-1-yl)pyridin-3-yl)-2,5-dimethyl-piperazine-1-carboxamide | 2-13 |
| 70 | (2R,5S)-4-(8-cyanoquinolin-5-yl)-N-(2-(4-((((1r,3r)-3-((2-(2,6-dioxopiperidin-3-yl)-1,3-dioxoiso-indolin-5-yl)oxy)cyclobutyl)(isopropyl)amino)methyl)piperidin-1-yl)pyrimidin-5-yl)-2,5-dimethylpiperazine-1-carboxamide | 2-14 |
| 71 | (3S)-4-(8-cyanoquinolin-5-yl)-N-(6-(4-((4-(2-(2,6-dioxopiperidin-3-yl)-1,3-dioxoisoindolin-5-yl)-piperazin-1-yl)methyl)piperidin-1-yl)pyridin-3-yl)-3-methylpiperazine-1-carboxamide | 2-15 |
| 72 | (3S)-4-(8-cyanoquinolin-5-yl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-3-methylpiperazine-1-carboxamide | 2-16 |

TABLE 3-continued

Exemplary Compounds of the Present Disclosure

| # | Structure & Name | Reference Number |
|---|---|---|
| 73 | (2R,5S)-4-(8-cyanoquinolin-5-yl)-N-(4-(4-((4-(2-(2,6-dioxopiperidin-3-yl)-1,3-dioxoisoindolin-5-yl)-piperazin-1-yl)methyl)piperidin-1-yl)-2,5-difluorophenyl)-2,5-dimethylpiperazine-1-carboxamide | 2-17 |
| 74 | (2R,5S)-4-(8-cyanoquinolin-5-yl)-N-(4-(4-((4-(2-((S)-2,6-dioxopiperidin-3-yl)-1-oxoisoindolin-5-yl)-piperazin-1-yl)methyl)piperidin-1-yl)-2,5-difluorophenyl)-2,5-dimethylpiperazine-1-carboxamide | 2-18 |
| 75 | (2R,5S)-4-(8-cyanoquinolin-5-yl)-N-(6-(4-(2-(4-(2-(2,6-dioxopiperidin-3-yl)-1,3-dioxoisoindolin-5-yl)piperazin-1-yl)ethyl)piperidin-1-yl)pyridin-3-yl)-2,5-dimethylpiperazine-1-carboxamide | 2-19 |
| 76 | (2R,5S)-4-(8-cyanoquinolin-5-yl)-N-(2-(4-(2-(4-(2-(2,6-dioxopiperidin-3-yl)-1,3-dioxoisoindolin-5-yl)piperazin-1-yl)ethyl)piperidin-1-yl)pyrimidin-5-yl)-2,5-dimethylpiperazine-1-carboxamide | 2-20 |
| 77 | (2R,5S)-4-(8-cyanoquinolin-5-yl)-N-(4-(4-((4-(2-((S)-2,6-dioxopiperidin-3-yl)-1-oxoisoindolin-5-yl)piperazin-1-yl)methyl)piperidin-1-yl)-3-fluorophenyl)-2,5-dimethylpiperazine-1-carboxamide | 2-21 |

TABLE 3-continued

Exemplary Compounds of the Present Disclosure

| # | Structure & Name | Reference Number |
|---|---|---|
| 78 | 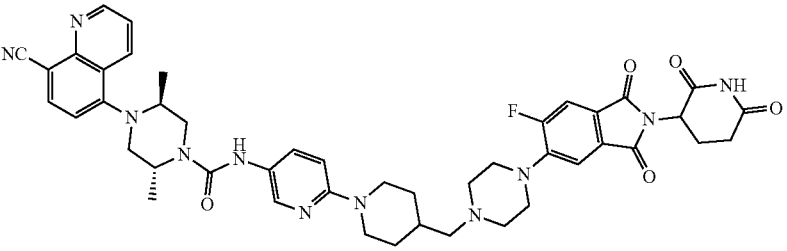<br>(2R,5S)-4-(8-cyanoquinolin-5-yl)-N-(6-(4-((4-(2-(2,6-dioxopiperidin-3-yl)-6-fluoro-1,3-dioxoisoindolin-5-yl)piperazin-1-yl)methyl)piperidin-1-yl)pyridin-3-yl)-2,5-dimethyl-piperazine-1-carboxamide | 2-22 |
| 79 | 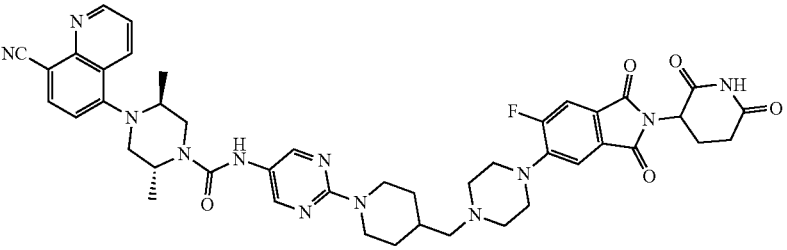<br>(2R,5S)-4-(8-cyanoquinolin-5-yl)-N-(2-(4-((4-(2-(2,6-dioxopiperidin-3-yl)-6-fluoro-1,3-dioxoisoindolin-5-yl)piperazin-1-yl)methyl)piperidin-1-yl)pyrimidin-5-yl)-2,5-dimethyl-piperazine-1-carboxamide | 2-23 |
| 80 | 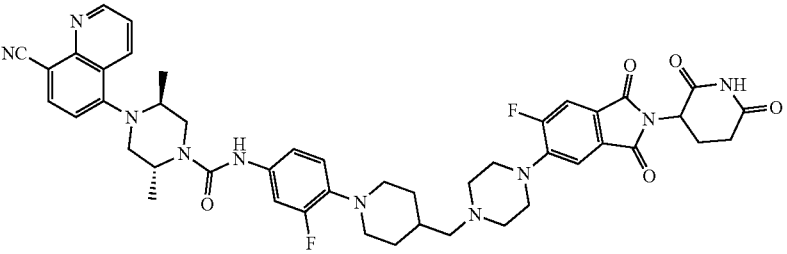<br>(2R,5S)-4-(8-cyanoquinolin-5-yl)-N-(4-(4-((4-(2-(2,6-dioxopiperidin-3-yl)-6-fluoro-1,3-dioxoisoindolin-5-yl)piperazin-1-yl)methyl)piperidin-1-yl)-3-fluorophenyl)-2,5-dimethylpiperazine-1-carboxamide | 2-24 |
| 81 | 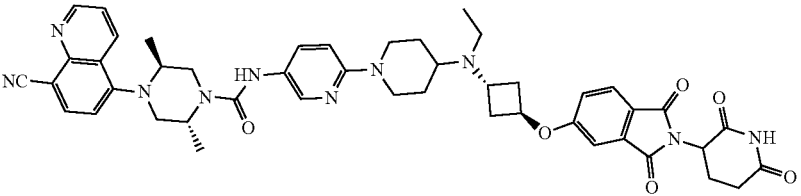<br>(2R,5S)-4-(8-cyanoquinolin-5-yl)-N-(6-(4-(((1r,3R)-3-((2-(2,6-dioxopiperidin-3-yl)-1,3-dioxoisoindolin-5-yl)oxy)cyclobutyl)(ethyl)amino)piperidin-1-yl)pyridin-3-yl)-2,5-dimethylpiperazine-1-carboxamide | 2-25 |

TABLE 3-continued

Exemplary Compounds of the Present Disclosure

| # | Structure & Name | Reference Number |
|---|---|---|
| 82 | (2R,5S)-4-(8-cyanoquinolin-5-yl)-N-(6-(4-(((1r,3R)-3-((2-(2,6-dioxopiperidin-3-yl)-1,3-dioxo-isoindolin-5-yl)oxy)cyclobutyl)(isopropyl)amino)piperidin-1-yl)pyridin-3-yl)-2,5-dimethyl-piperazine-1-carboxamide | 2-26 |
| 83 | (2R,5S)-4-(8-cyanoquinolin-5-yl)-N-(2-(4-(((1r,3R)-3-((2-(2,6-dioxopiperidin-3-yl)-1,3-dioxoiso-indolin-5-yl)oxy)cyclobutyl)(isopropyl)amino)piperidin-1-yl)pyrimidin-5-yl)-2,5-dimethyl-piperazine-1-carboxamide | 2-27 |
| 84 | (2R,5S)-4-(8-cyanoquinolin-5-yl)-N-(6-(4-((4-(2-((S)-2,6-dioxopiperidin-3-yl)-6-fluoro-1-oxoisoindolin-5-yl)piperazin-1-yl)methyl)piperidin-1-yl)pyridin-3-yl)-2,5-dimethyl-piperazine-1-carboxamide | 2-28 |
| 85 | (2R,5S)-4-(8-cyanoquinolin-5-yl)-N-(2-(4-((4-(2-((S)-2,6-dioxopiperidin-3-yl)-6-fluoro-1-oxoisoindolin-5-yl)piperazin-1-yl)methyl)piperidin-1-yl)pyrimidin-5-yl)-2,5-dimethyl-piperazine-1-carboxamide | 2-29 |

TABLE 3-continued

Exemplary Compounds of the Present Disclosure

| # | Structure & Name | Reference Number |
|---|---|---|
| 86 | 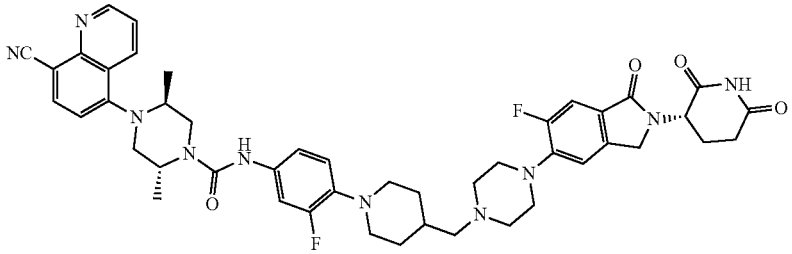<br>(2R,5S)-4-(8-cyanoquinolin-5-yl)-N-(4-(4-(4-(2-((S)-2,6-dioxopiperidin-3-yl)-6-fluoro-1-oxoisoindolin-5-yl)piperazin-1-yl)methyl)piperidin-1-yl)-3-fluorophenyl)-2,5-dimethyl-piperazine-1-carboxamide | 2-30 |

Pharmaceutical Compositions

Pharmaceutical compositions of the present disclosure comprise at least one compound of Formulae (1) (e.g. Formula (1A)) or (2) (e.g. Formula (2A)), or a tautomer, stereoisomer, or pharmaceutically acceptable salt thereof, or a deuterated derivative of any of the foregoing formulated together with a pharmaceutically acceptable carrier. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula (1) (e.g. Formula (1A)) or (2) (e.g. Formula (2A)), or a tautomer, stereoisomer, or pharmaceutically acceptable salt thereof, or a deuterated derivative of any of the foregoing, which are approximately isotonic with the blood of the intended recipient. These preparations are administered intravenously, although administration may also be affected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula (1) (e.g. Formula (1A)) or (2) (e.g. Formula (2A)), or a tautomer, stereoisomer, or pharmaceutically acceptable salt thereof, or a deuterated derivative of any of the foregoing) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following table (Table 4) for Equivalent Surface Area Dosage Factors).

TABLE 4

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Methods of Treatment

In some embodiments, a compound of Formula (1) (e.g. Formula (1A)) or (2) (e.g. Formula (2A)), or a tautomer, stereoisomer, or pharmaceutically acceptable salt thereof, or a deuterated derivative of any of the foregoing, is administered to treat cancer in a subject in need thereof. In some embodiments, the cancer is chosen from prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer. In some embodiments, the cancer is prostate cancer. In some embodiments, the cancer is head and neck cancer. In some embodiments, the cancer is skin cancer. In some embodiments, the cancer is sarcoma. In some embodiments, the cancer is renal cell carcinoma. In some embodiments, the cancer is adrenocortical carcinoma. In some embodiments, the cancer is bladder cancer. In some embodiments, the cancer is lung cancer. In some embodiments, the cancer is gastric carcinoma. In some embodiments, the cancer is esophageal carcinoma. In some embodiments, the cancer is pancreatic adenocarcinoma. In some embodiments, the cancer is colorectal cancer. In some embodiments, the cancer is connective tissue cancer. In some embodiments, the cancer is glioblastoma multiforme. In some embodiments, the cancer is cervical cancer. In some embodiments, the cancer is uterine cancer. In some embodiments, the cancer is ovarian cancer. In some embodiments, the cancer is breast cancer.

In some embodiments, the cancer is androgen receptor positive.

In some embodiments, a compound of Formulae (1) (e.g. Formula (1A)) or (2) (e.g. Formula (2A)), or a tautomer, stereoisomer, or pharmaceutically acceptable salt thereof, or a deuterated derivative of any of the foregoing, is administered as a pharmaceutical composition.

In some embodiments, the subject has been previously treated with an anti-cancer agent. In some embodiments, the anti-cancer agent is enzalutamide, apalutamide, bicalutamide, darolutamide, flutamide, abiraterone, or a combination of any of the foregoing. In some embodiments, the anti-cancer agent is enzalutamide.

In some embodiments, provided herein is a use of a compound of Formula (1) (e.g. Formula (1A)) or (2) (e.g. Formula (2A)), or a tautomer, stereoisomer, or pharmaceutically acceptable salt thereof, or a deuterated derivative of any of the foregoing, for treating cancer. In some embodiments, the cancer is selected from prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer. In some embodiments, the cancer is prostate cancer. In some embodiments, the cancer is head and neck cancer. In some embodiments, the cancer is skin cancer. In some embodiments, the cancer is sarcoma. In some embodiments, the cancer is renal cell carcinoma. In some embodiments, the cancer is adrenocortical carcinoma. In some embodiments, the cancer is bladder cancer. In some embodiments, the cancer is lung cancer. In some embodiments, the cancer is gastric carcinoma. In some embodiments, the cancer is esophageal carcinoma. In some embodiments, the cancer is pancreatic adenocarcinoma. In some embodiments, the cancer is colorectal cancer. In some embodiments, the cancer is connective tissue cancer. In some embodiments, the cancer is glioblastoma multiforme. In some embodiments, the cancer is cervical cancer. In some embodiments, the cancer is uterine cancer. In some embodiments, the cancer is ovarian cancer. In some embodiments, the cancer is breast cancer. In some embodiments, the cancer is androgen receptor positive.

In some embodiments, provided herein is a use of a compound of Formula (1) or (2), or a tautomer, stereoisomer, or pharmaceutically acceptable salt thereof, or a deuterated derivative of any of the foregoing, in the preparation of a medicament. In some embodiments, the medicament is for the treatment of cancer. In some embodiments, the cancer is selected from prostate cancer, head and neck cancer, skin cancer, sarcoma, renal cell carcinoma, adrenocortical carcinoma, bladder cancer, lung cancer, gastric carcinoma, esophageal carcinoma, pancreatic adenocarcinoma, colorectal cancer, connective tissue cancer, glioblastoma multiforme, cervical cancer, uterine cancer, ovarian cancer, and breast cancer. In some embodiments, the cancer is prostate cancer. In some embodiments, the cancer is head and neck cancer. In some embodiments, the cancer is skin cancer. In some embodiments, the cancer is sarcoma. In some embodiments, the cancer is renal cell carcinoma. In some embodiments, the cancer is adrenocortical carcinoma. In some embodiments, the cancer is bladder cancer. In some embodiments, the cancer is lung cancer. In some embodiments, the cancer is gastric carcinoma. In some embodiments, the cancer is esophageal carcinoma. In some embodiments, the cancer is pancreatic adenocarcinoma. In some embodiments, the cancer is colorectal cancer. In some embodiments, the cancer is connective tissue cancer. In some embodiments, the cancer is glioblastoma multiforme. In some embodiments, the cancer is cervical cancer. In some embodiments, the cancer is uterine cancer. In some embodiments, the cancer is ovarian cancer. In some embodiments, the cancer is breast cancer. In some embodiments, the cancer is androgen receptor positive.

In some embodiments, provided herein is a method of inhibiting cell growth comprising contacting a cell with a compound of Formula (1) (e.g. Formula (1A)) or (2) (e.g. Formula (2A)), or a tautomer, stereoisomer, or pharmaceutically acceptable salt thereof, or a deuterated derivative of any of the foregoing. In some embodiments, the cell is a cancer cell. In some embodiments, the cancer cell is a prostate cancer cell. In some embodiments, the cell is androgen receptor positive.

In one embodiment, a compound of Formula (1) (e.g. Formula (1A)) or (2) (e.g. Formula (2A)), or a tautomer, stereoisomer, pharmaceutically acceptable salt or hydrate thereof, may be administered in combination with another therapeutic agent. The other therapeutic agent can provide additive or synergistic value relative to the administration of a compound of the present disclosure alone. The therapeutic agent can be selected from, for example, hormones and hormonal analogues; signal transduction pathway inhibitors; topoisomerase I inhibitors; topoisomerase II inhibitors; antimetabolite neoplastic agents; antibiotic neoplastic agents; alkylating agents; anti-microtubule agents; platinum coordination complexes; aromatase inhibitors; and anti-mitotic agents.

In some embodiments, the therapeutic agent may be a hormone or hormonal analogue. In some embodiments, the therapeutic agent may be a signal transduction pathway inhibitor. In some embodiments, the therapeutic agent may be a topoisomerase I inhibitor. In some embodiments, the therapeutic agent may be a topoisomerase II inhibitor. In some embodiments, the therapeutic agent may be an antimetabolite neoplastic agent. In some embodiments, the therapeutic agent may be an antibiotic neoplastic agent. In some embodiments, the therapeutic agent may be an alkylating agent. In some embodiments, the therapeutic agent may be an anti-microtubule agent. In some embodiments, the therapeutic agent may be a platinum coordination complex. In some embodiments, the therapeutic agent may be an aromatase inhibitor. In some embodiments, the therapeutic agent may be an anti-mitotic agent.

In some embodiments, the aromatase inhibitor may be selected from anastrazole, letrozole, vorozole, fadrozole, exemestane, and formestane. In some embodiments, the aromatase inhibitor is anastrazole. In some embodiments, the aromatase inhibitor may be letrozole. In some embodiments, the aromatase inhibitor may be vorozole. In some embodiments, the aromatase inhibitor may be fadrozole. In some embodiments, the aromatase inhibitor may be exemestane. In some embodiments, the aromatase inhibitor may be formestane.

In some embodiments, the anti-mitotic agent may be selected from paclitaxel, docetaxel, and Abraxane. In some embodiments, the anti-mitotic agent may be paclitaxel. In some embodiments, the anti-mitotic agent may be docetaxel. In some embodiments, the anti-mitotic agent may be Abraxane.

In some embodiments, a compound of Formula (1) (e.g. Formula (1A)) or (2) (e.g. Formula (2A)), or a tautomer, stereoisomer, or pharmaceutically acceptable salt thereof, or a deuterated derivative of any of the foregoing, may be administered in combination with a hormone or hormonal analog. In some embodiments, a compound of Formula (1) or (2), or a tautomer, stereoisomer, or pharmaceutically acceptable salt thereof, or a deuterated derivative of any of the foregoing, may be administered in combination with a signal transduction pathway inhibitor. In some embodiments, a compound of Formula (1) or (2), or a tautomer, stereoisomer, or pharmaceutically acceptable salt thereof, or a deuterated derivative of any of the foregoing, may be administered in combination with an antimetabolite neoplastic agent. In some embodiments, a compound of Formulae (1) or (2), or a tautomer, stereoisomer, or pharmaceutically acceptable salt thereof, or a deuterated derivative of any of the foregoing, may be administered in combination with a topoisomerase I inhibitor. In some embodiments, a compound of Formula (1) or (2), or a tautomer, stereoisomer, or pharmaceutically acceptable salt thereof, or a deuterated derivative of any of the foregoing, may be administered in combination with a topoisomerase II inhibitor. In some embodiments, a compound of Formula (1) or (2), or a tautomer, stereoisomer, or pharmaceutically acceptable salt thereof, or a deuterated derivative of any of the foregoing, may be administered in combination with an aromatase inhibitor.

Examples

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from about −10° C. to about 200° C. Further, except as otherwise specified, reaction times and conditions are intended to be approximate, e.g., taking place at about atmospheric pressure within a temperature range of about −10° C. to about 200° C. over a period that can be, for example, about 1 to about 24 hours; reactions left to run overnight in some embodiments can average a period of about 16 hours.

Isolation and purification of the chemical entities and intermediates described herein can be affected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, $3^{rd}$ Ed., 1990 New York: Plenum Press; Mundy et al., Name Reaction and Reagents in Organic Synthesis, $2^{nd}$ Ed., 2005 Hoboken, N.J.: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) Protective Groups in Organic Synthesis, $3^{rd}$ Ed., John Wiley & Sons). These groups may be removed at a convenient stage of the compound synthesis using methods that are readily apparent to those skilled in the art.

When desired, the (R)- and (S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Millipore Sigma or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valencies apply to all compounds disclosed herein in genus or named compound for unless otherwise specified.

All final compounds of the examples described herein were checked for purity by HPLC on a Shimadzu LC-2010A and compounds were detected at the wavelength of 214 nM and 254 nM. Purities for all final compounds were over 95% based on HPLC peaks (214 nM and 254 nM wavelength). Liquid chromatography condition: Column, XBRIDGE C18, 3.6 micron, 2.1×50 mm: Mobile phase, water (0.05% TFA) and acetonitrile (0.05% TFA), linear gradient from 10% acetonitrile to 100% acetonitrile over 7 min; Oven temperature 45° C.; Flow rate, 0.8 mL/mL. H-NMR was obtained on Bruker 400 MHz NMR spectrometer.

General Synthetic Schemes

Compounds of Formula (1) ((e.g. Formula (1A)), see compounds in Table 2) can be prepared according to the following schemes. The following schemes represent the general methods used in preparing these compounds. However, the synthesis of these compounds is not limited to these representative methods, as they can also be prepared by various other methods those skilled in the art of synthetic chemistry, for example, in a stepwise or modular fashion.

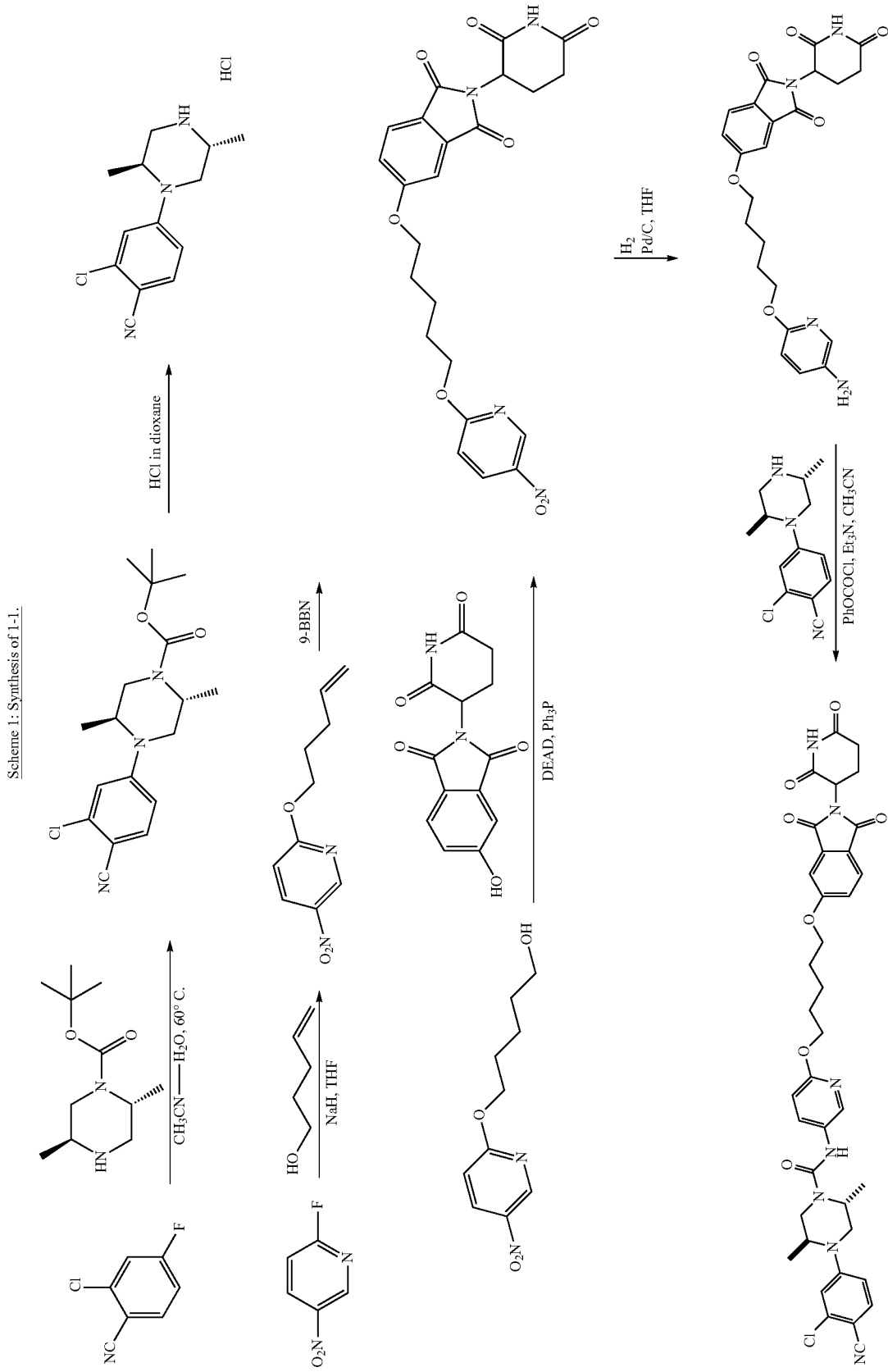

Compound 1-2 can be synthesized according to the method described in Scheme 1.

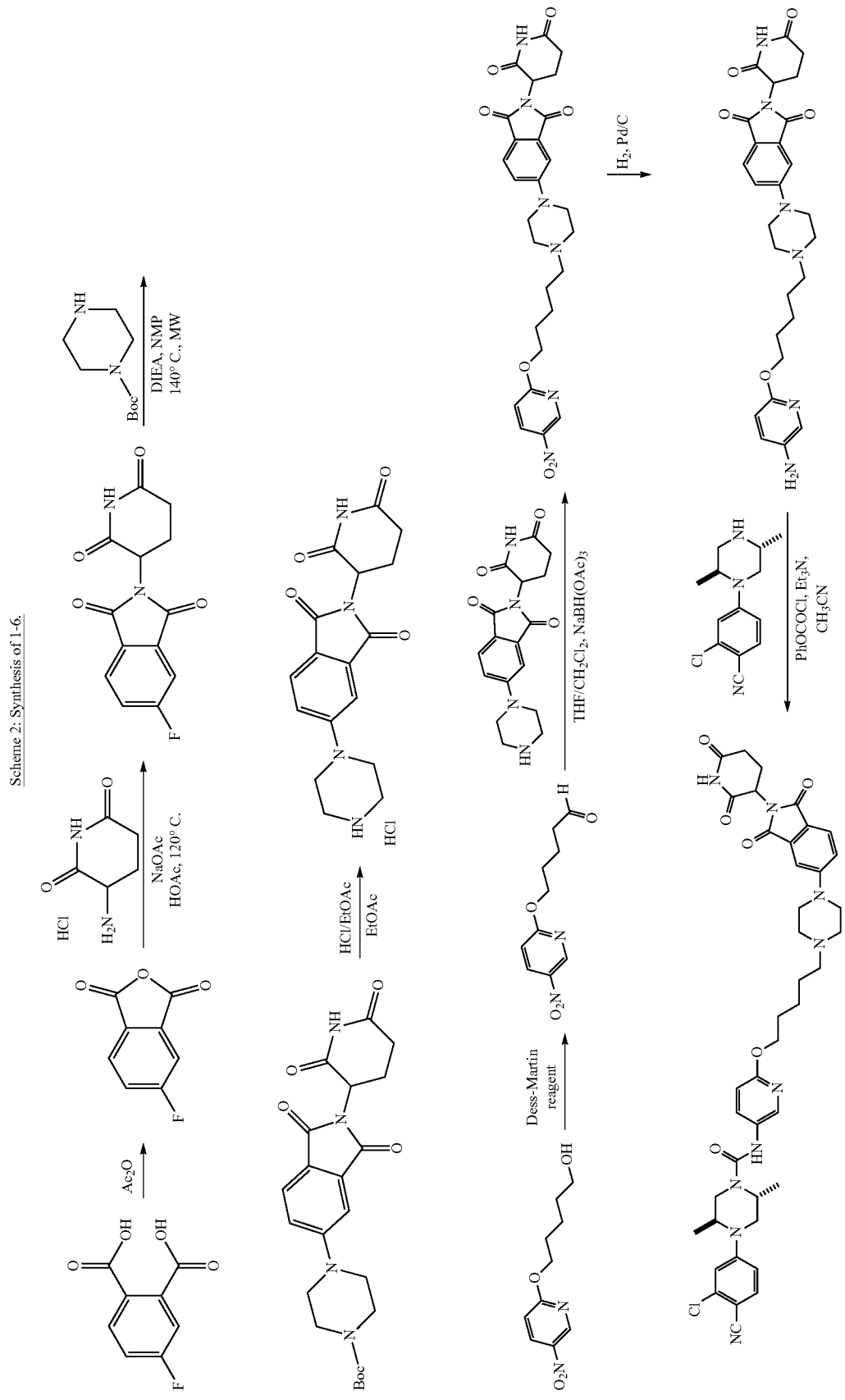

Compounds 1-3, 1-4, 1-5 can be prepared by a method similar to the one described in Scheme 2.
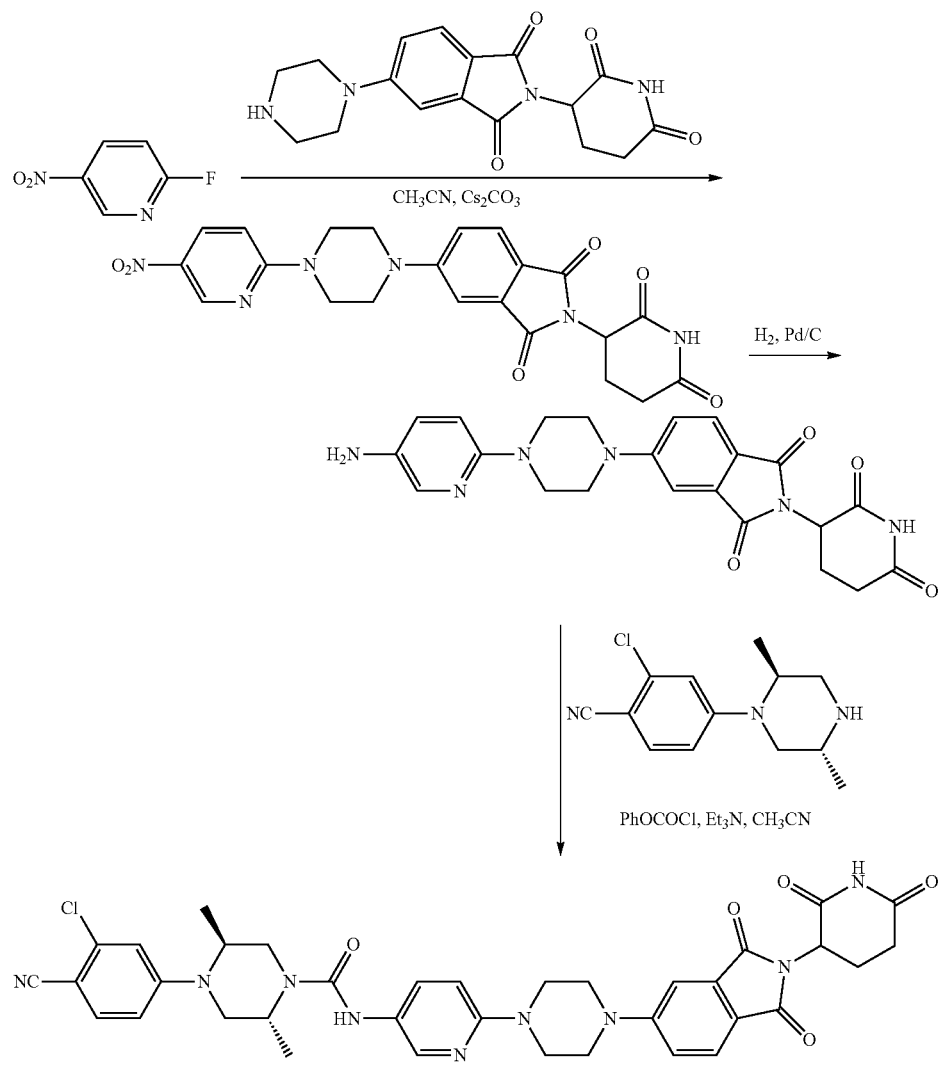
Scheme 3: Synthesis of 1-7.

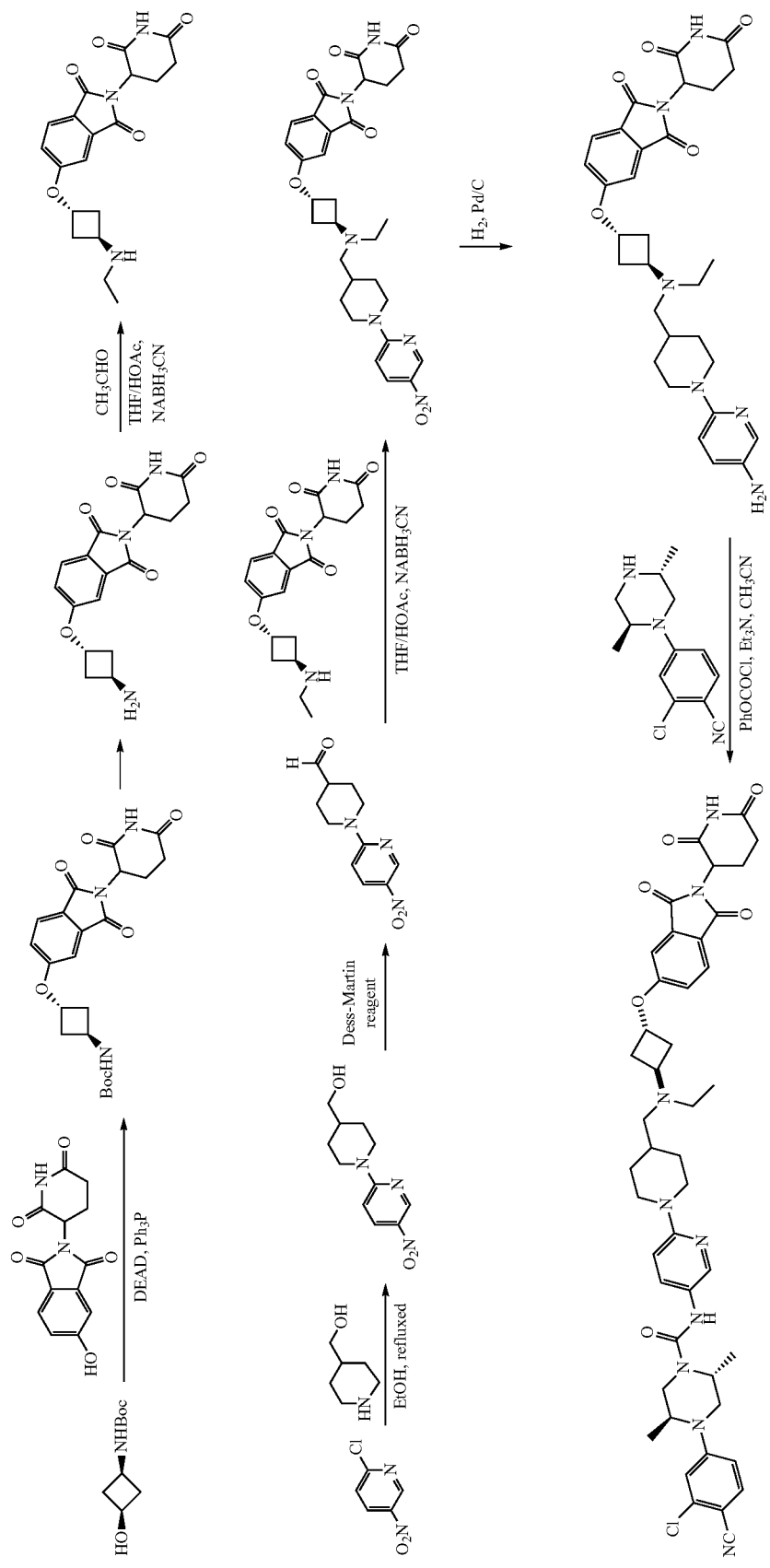
Scheme 4: Synthesis of 1-10.

Compounds 1-8, 1-9, 1-11 and 1-12 can be prepared by a method similar to the one described in Scheme 4.
Scheme 5: Synthesis of 1-14.
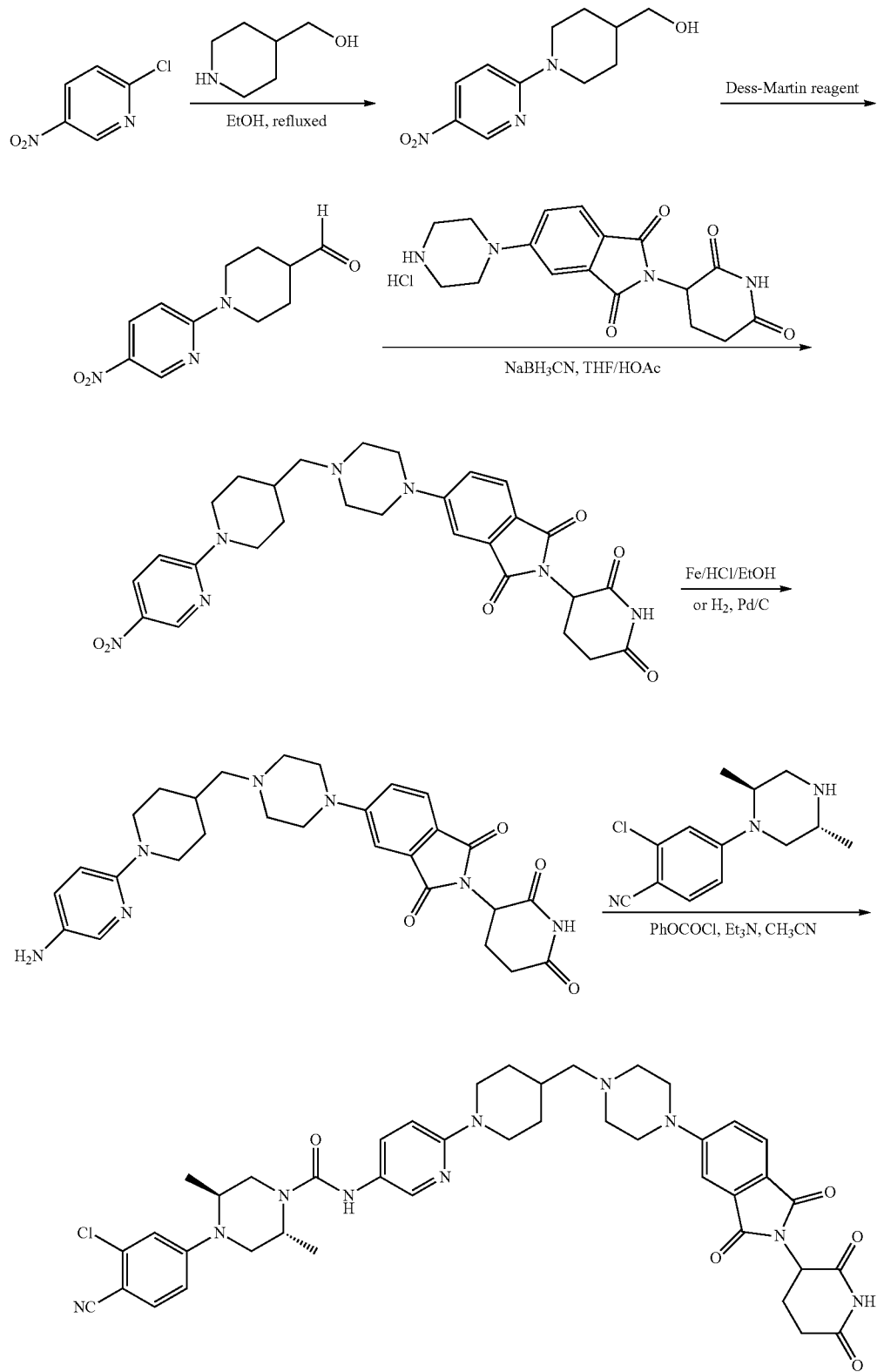

The following compounds can be prepared by a method similar to the one described in Scheme 5: 1-13, 1-15, 1-16, 1-17, 1-18, 1-20, 1-21, 1-22, 1-23, 1-24, 1-25, 1-26, 1-27, 1-30, 1-31, 1-36, 1-37, 1-45, 1-47, and 1-48.
Scheme 6: Synthesis of 1-28.
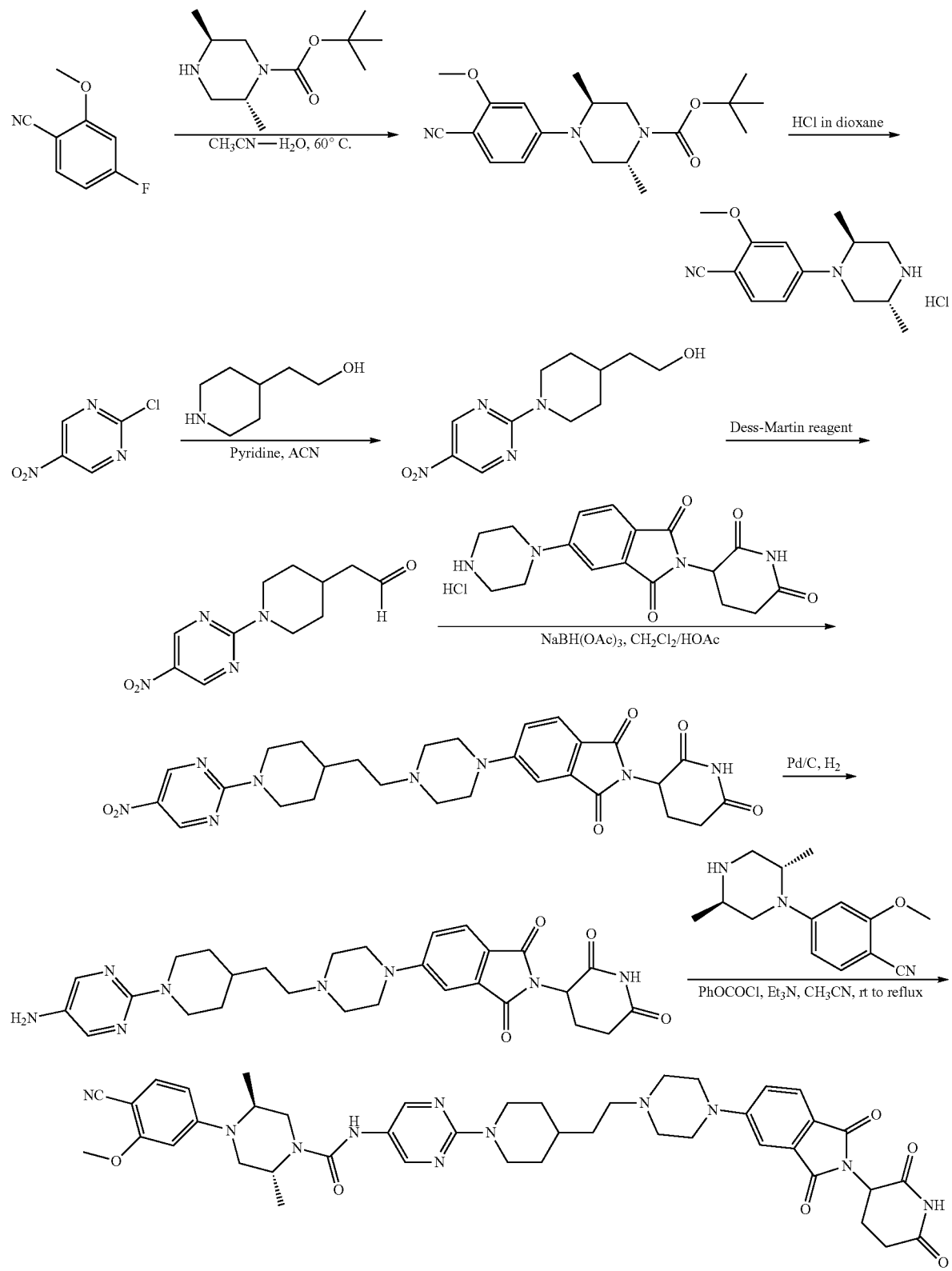

1-19 can be prepared by a method similar to the one described in Scheme 6.
Scheme 7: Synthesis of 1-29.
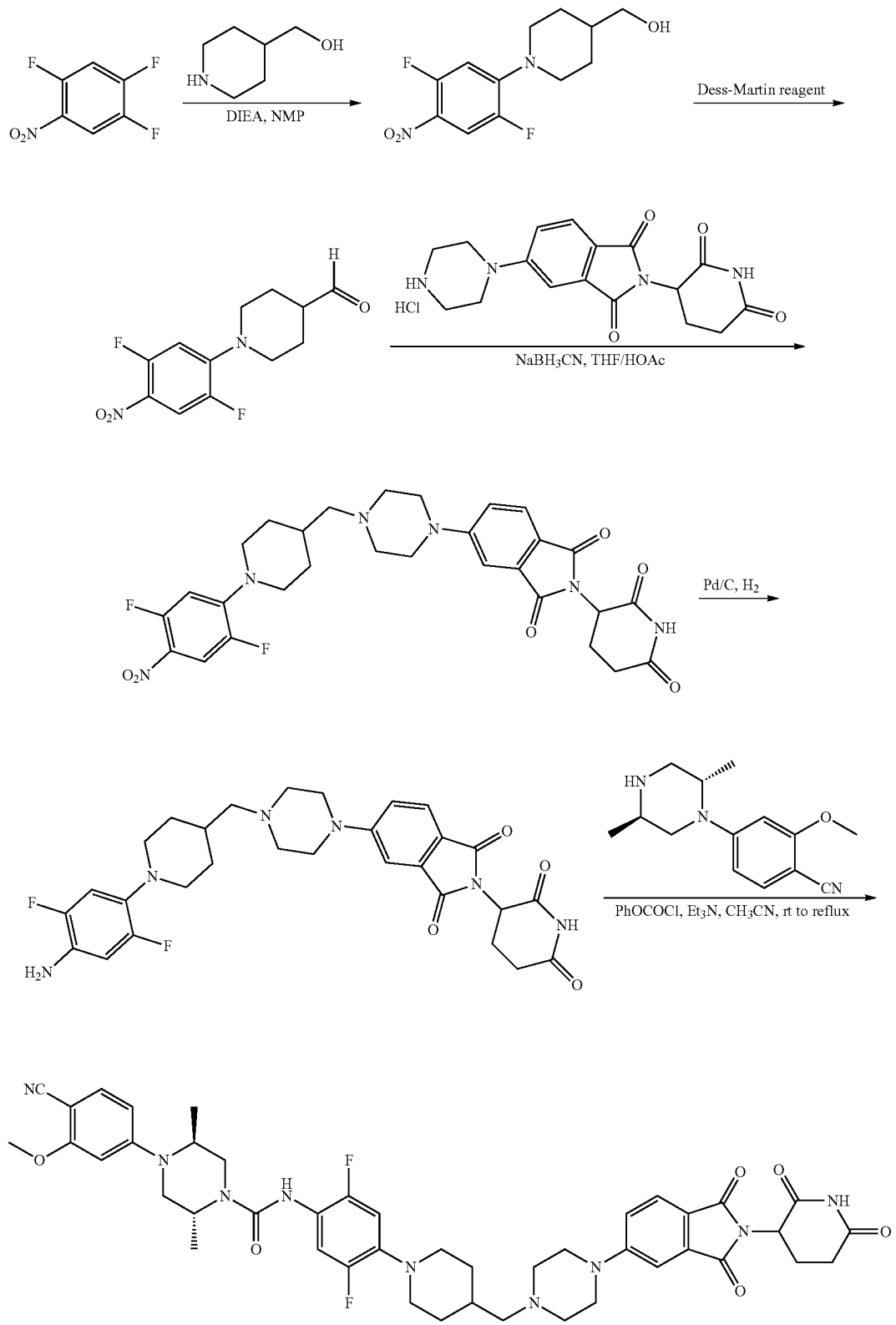

1-38 can be prepared by a method similar to the one described in Scheme 7.
Scheme 8: Synthesis of 1-54.
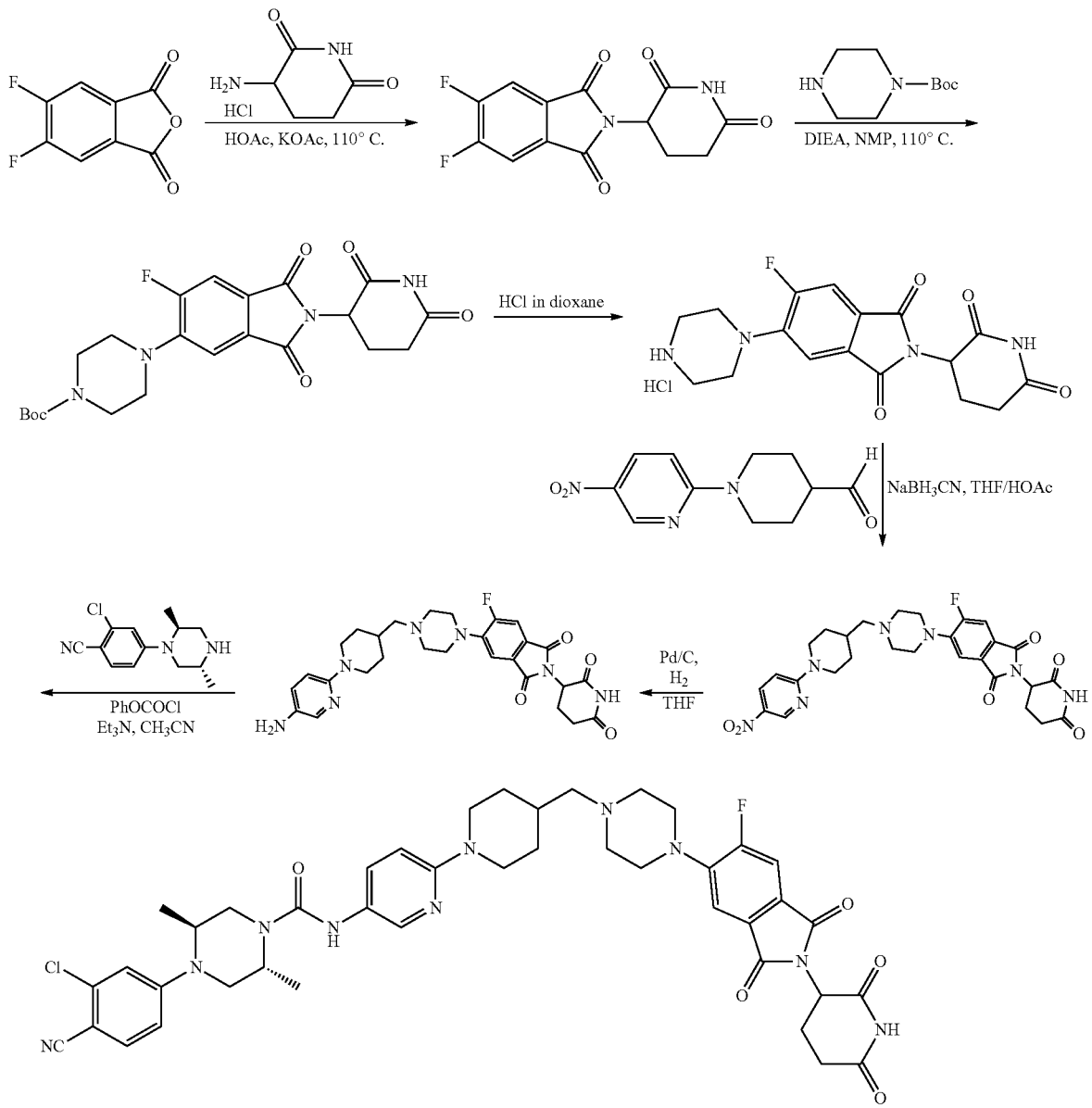
Compounds 1-39 and 1-41 can be prepared by a method similar to the one described in Scheme 8.
Scheme 9: Synthesis of 1-46.
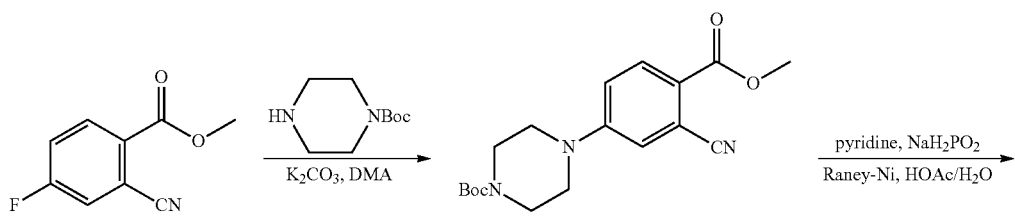

-continued
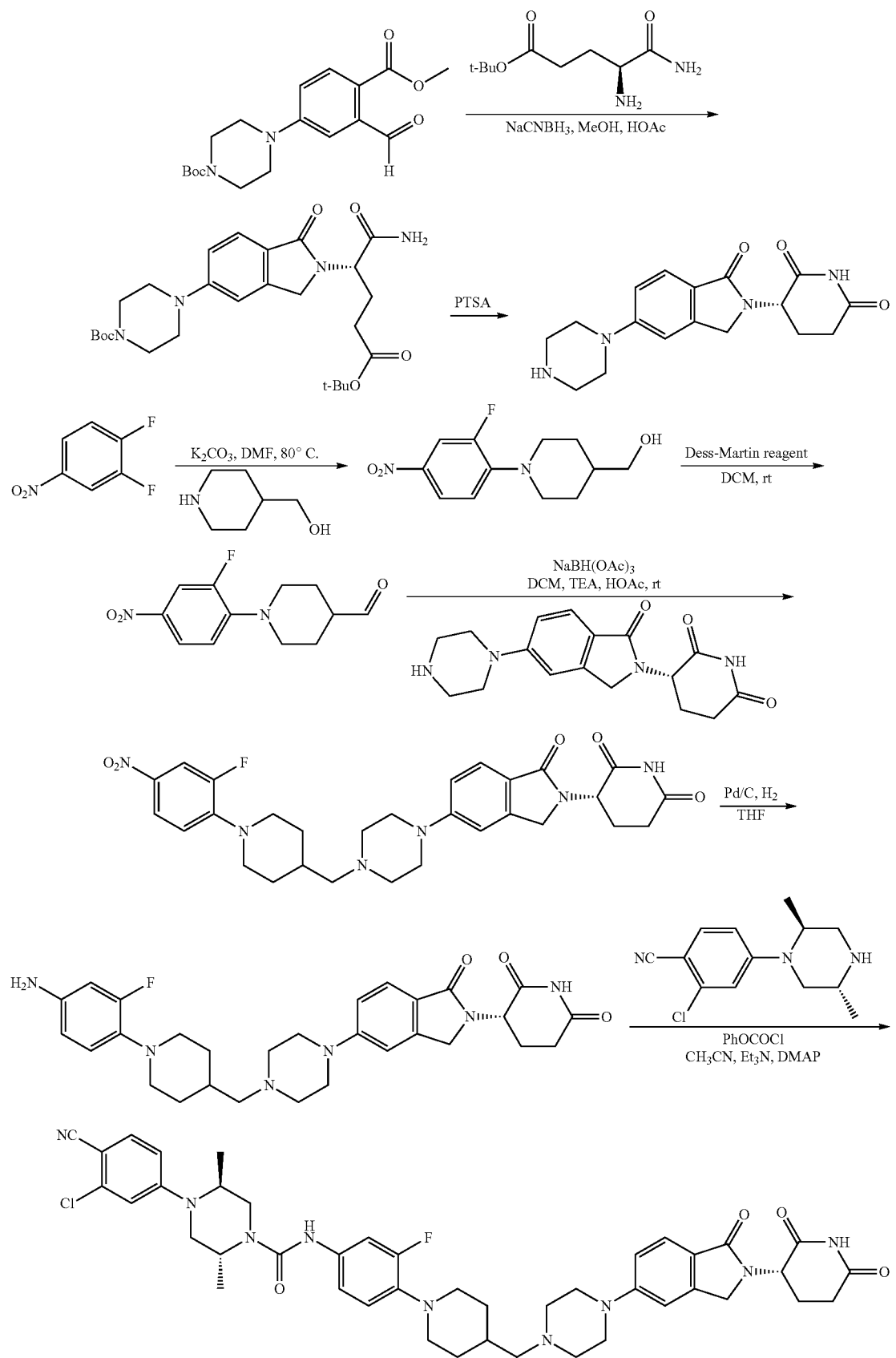

The following compounds can be synthesized according to the synthetic method described in Scheme 9: 1-32, 1-33, 1-34, 1-35, 1-40, 1-42, 1-43, 1-44, 1-49, 1-50, 1-51, 1-52, 1-53.

Compounds of Formula (2) ((e.g. Formula (2A)); see compounds described in Table 3) can be prepared according to the following schemes. The following schemes represent the general methods used in preparing these compounds. However, the synthesis of these compounds is not limited to these representative methods, as they can also be prepared by various other methods those skilled in the art of synthetic chemistry, for example, in a stepwise or modular fashion.

Scheme 10: Synthesis of 2-1.

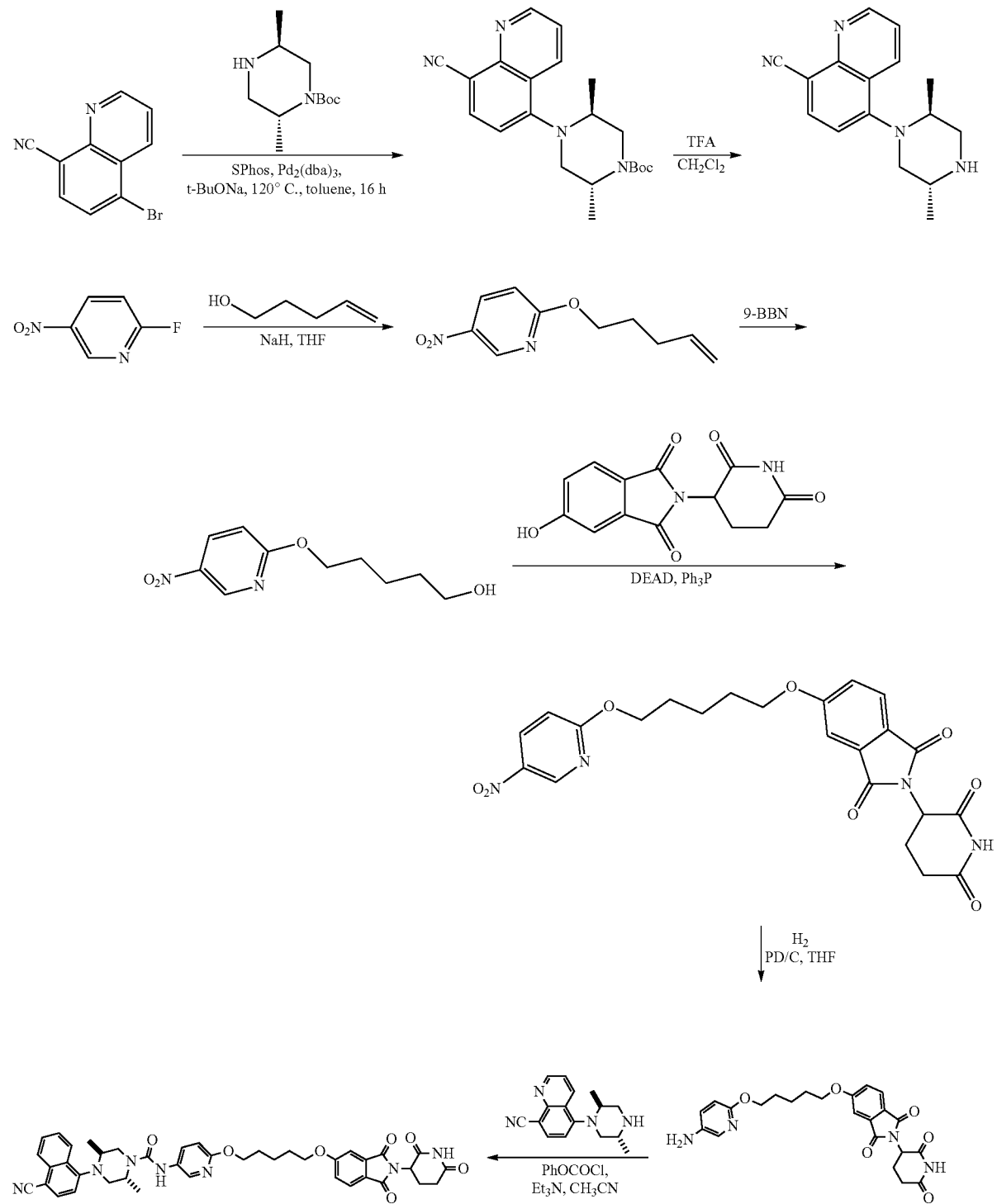

Compound 2-2 can be synthesized according to the synthetic method described in Scheme 10.
Scheme 11: Synthesis of 2-6.
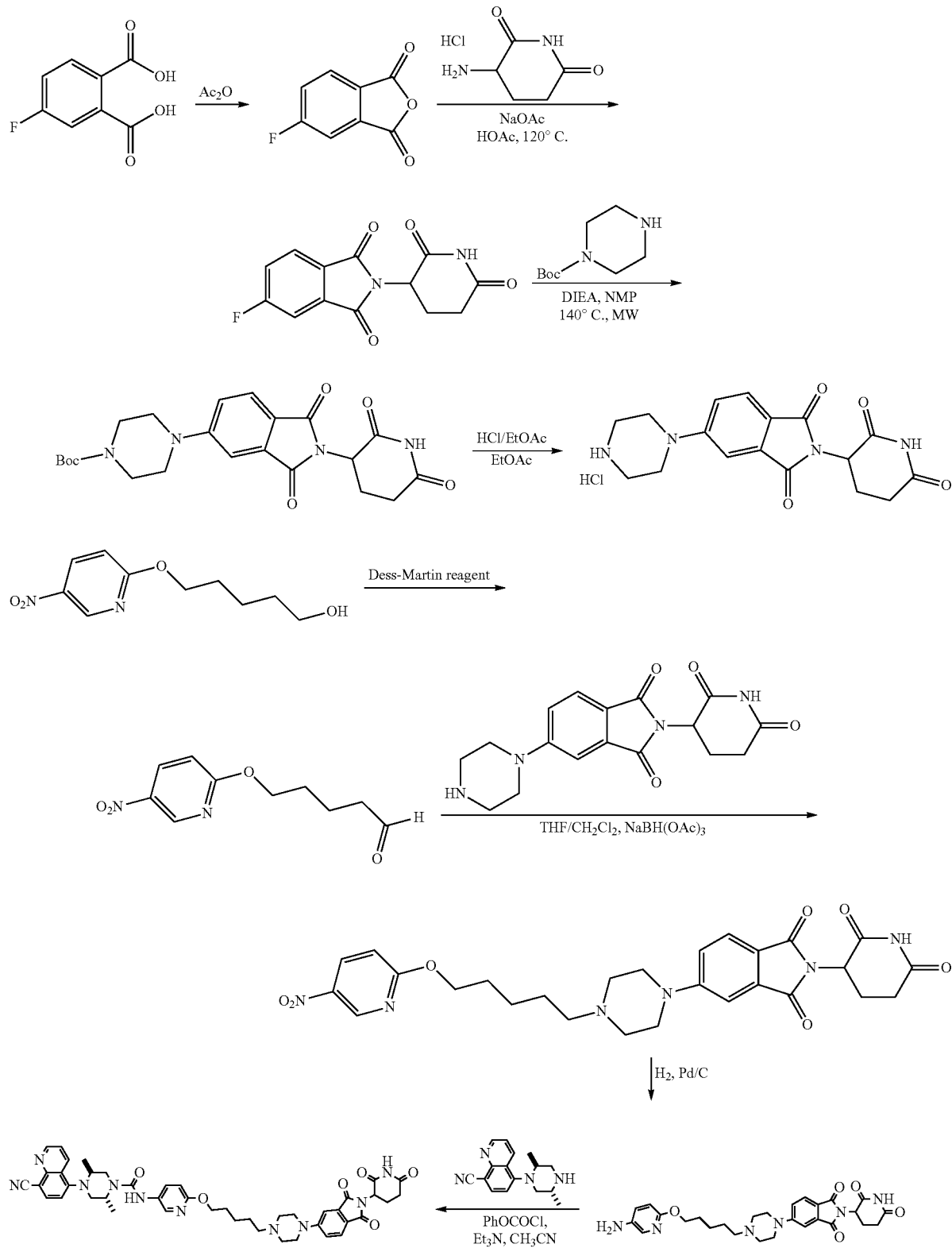

Compounds 2-3, 2-4, 2-5 were synthesized according to the synthetic method described in Scheme 11.
Scheme 12: Synthesis of 2-7.
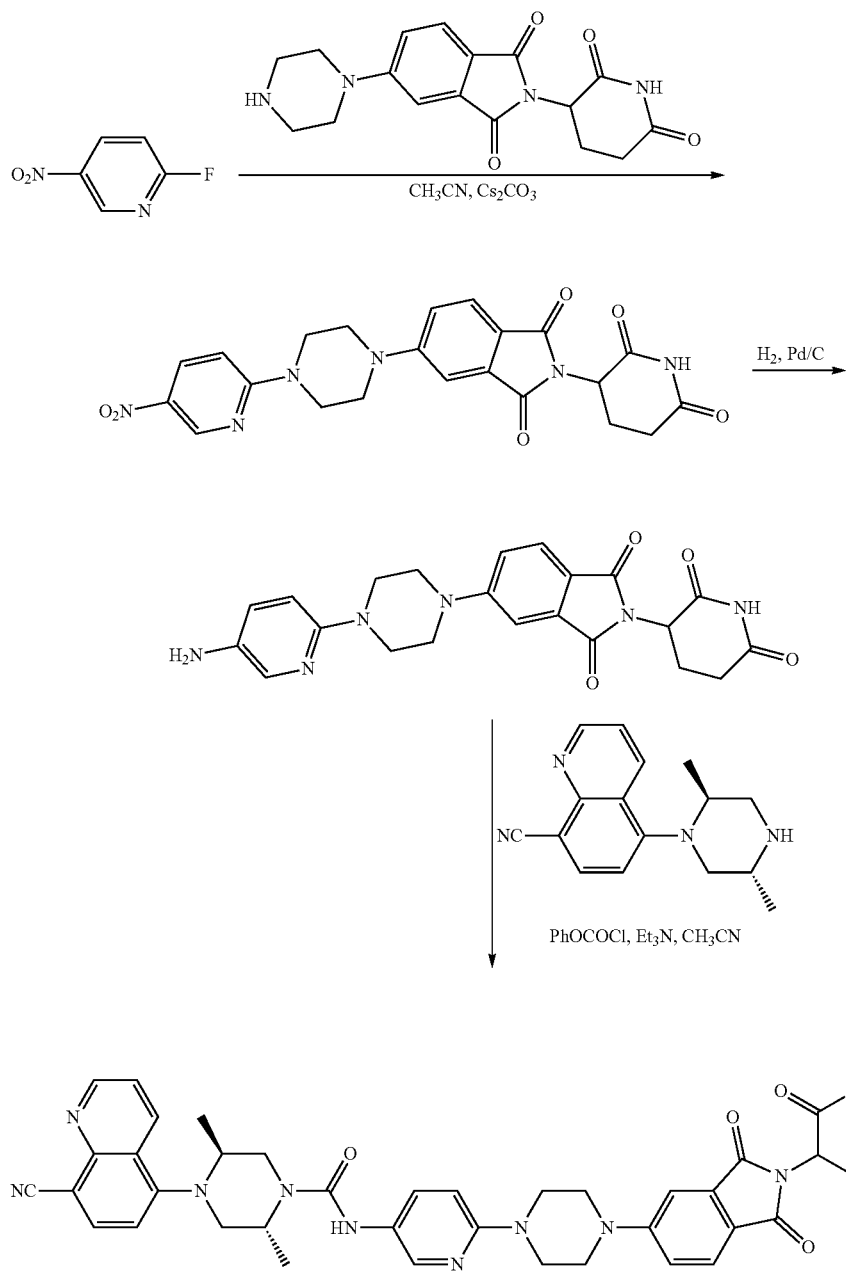
Scheme 13: Synthesis of 2-9.
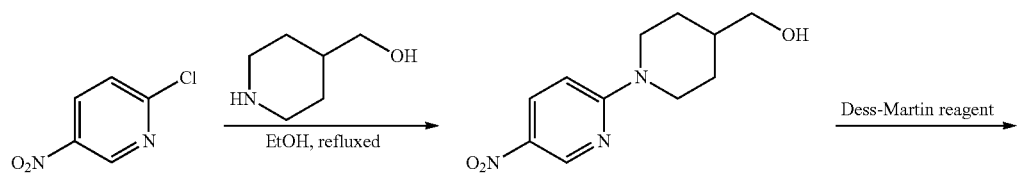

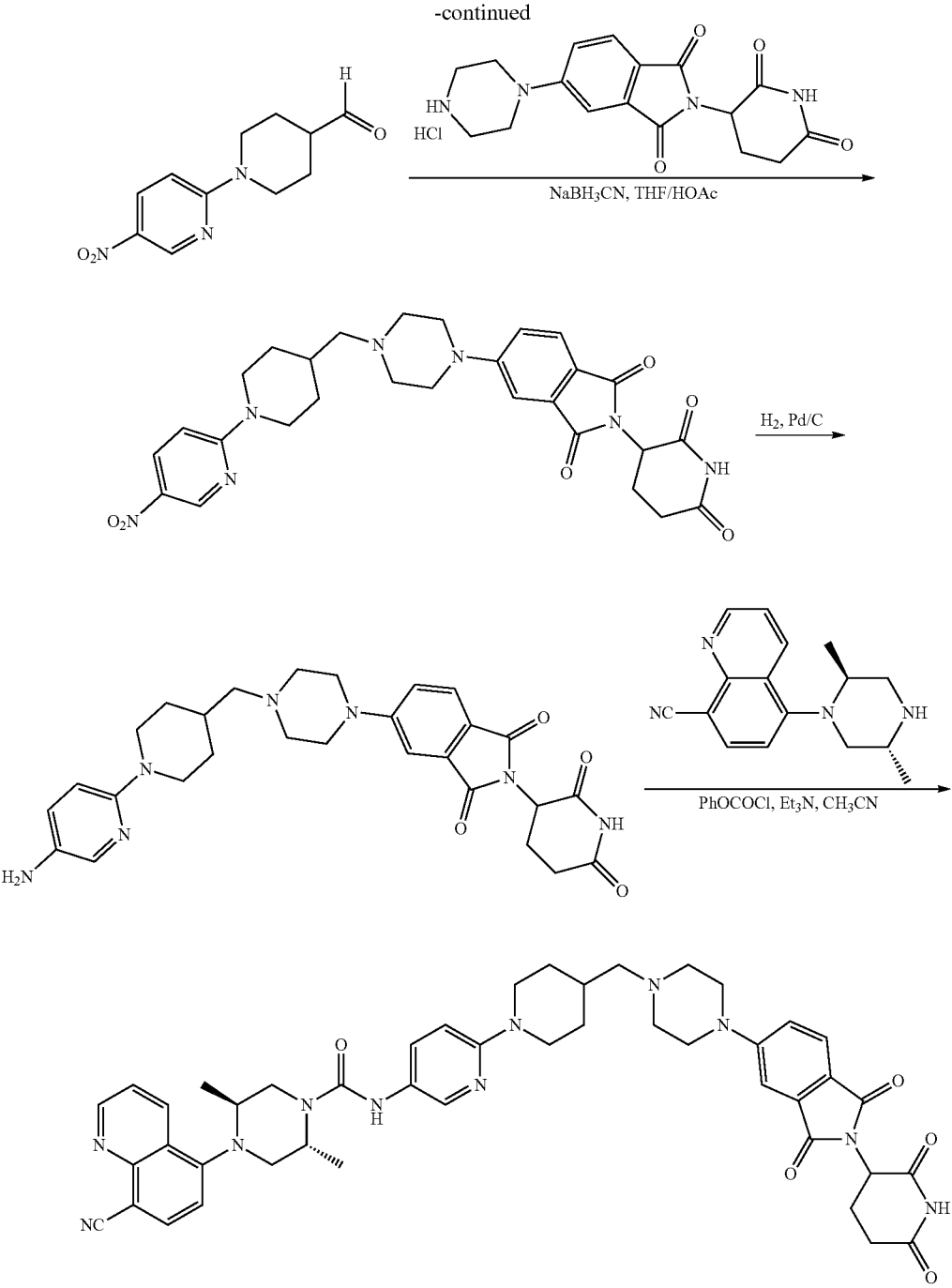
Compounds 2-8, 2-12, 2-15, and 2-16 can be synthesized according to the synthetic method described in Scheme 13.
Scheme 14: Synthesis of 2-17.
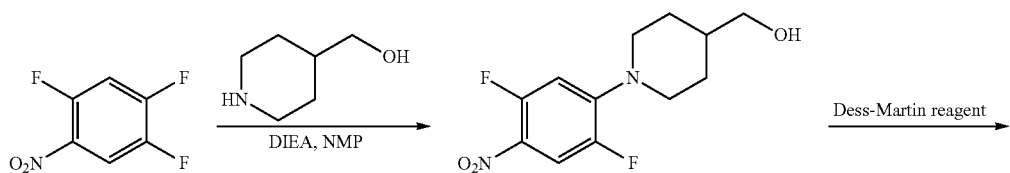

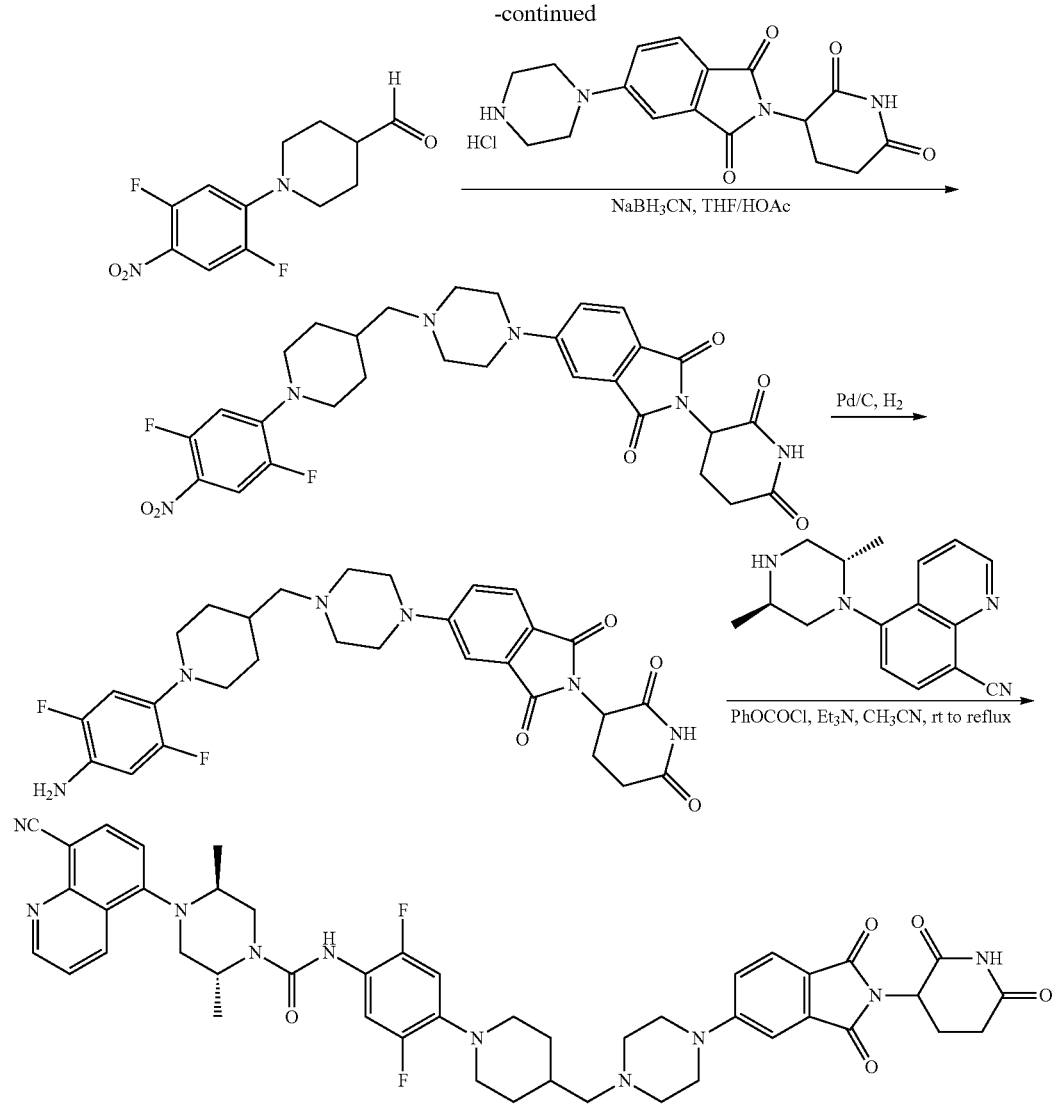
Scheme 15: Synthesis of 2-21.
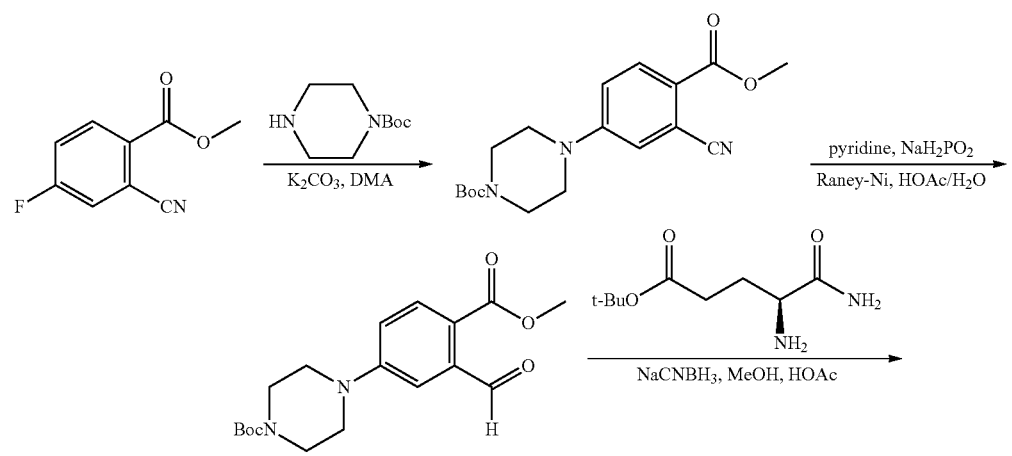

115
116
-continued
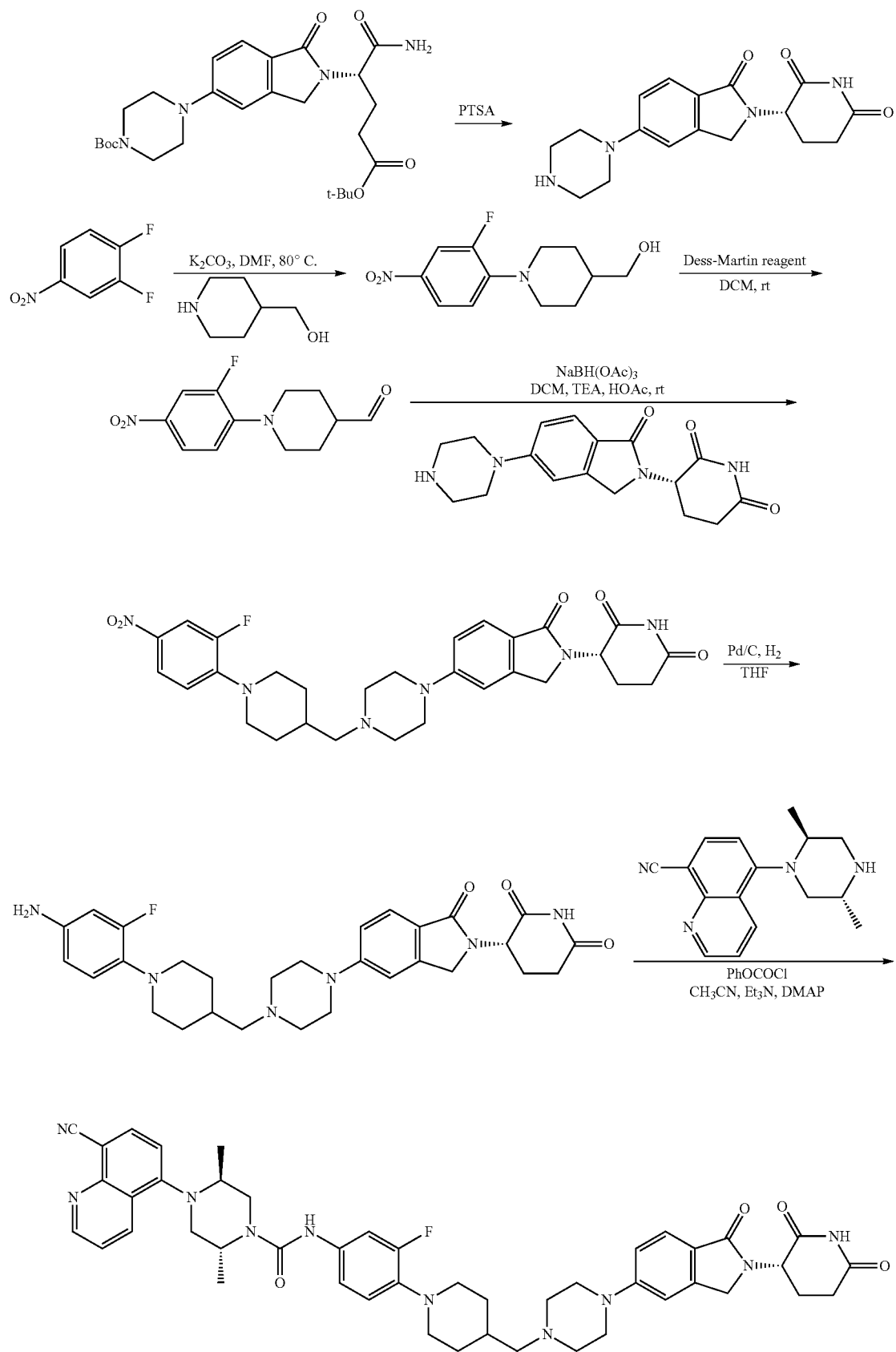

The following compounds can be synthesized according to the synthetic method described in Scheme 15: 2-10, 2-11, 2-18, 2-28, 2-29, and 2-30.
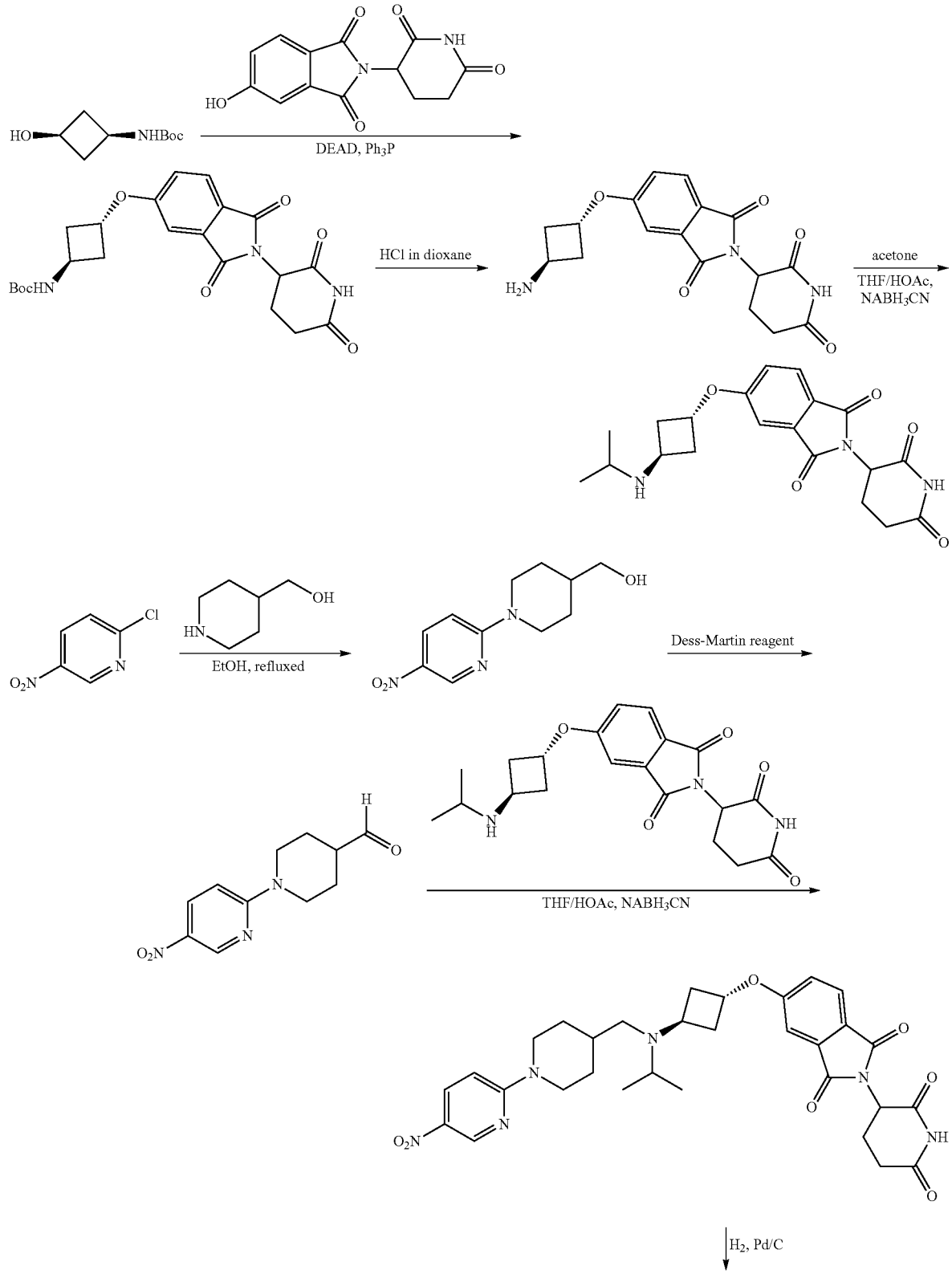
Scheme 16: Synthesis of 2-13.

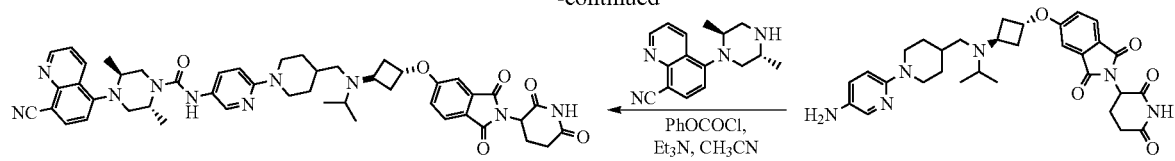
The following compounds can be synthesized according to the synthetic method described in Scheme 16: 2-14, 2-25, 2-26, and 2-27.
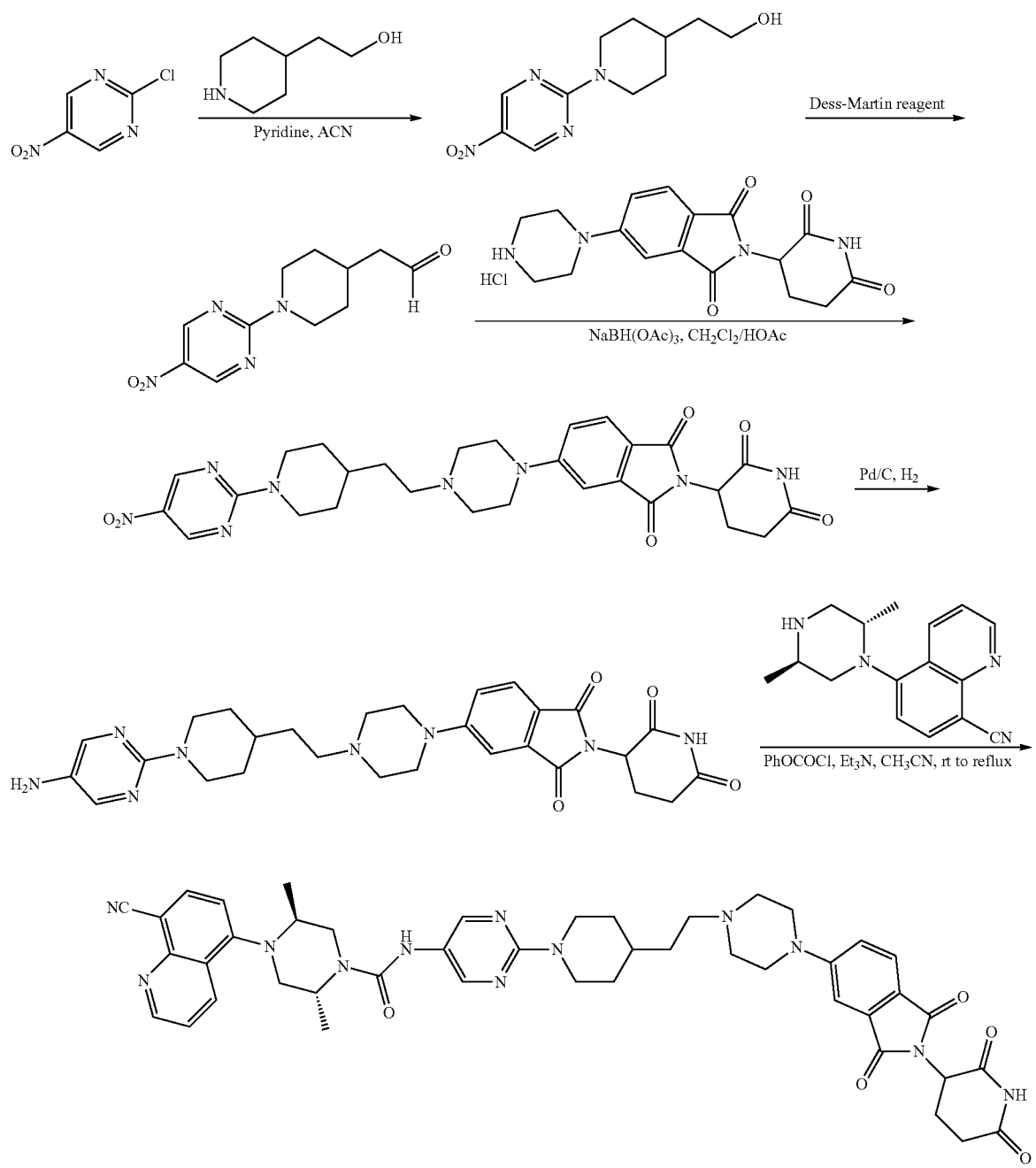

Compound 2-19 was synthesized using the same method as described in Scheme 17.

AcOH: acetic acid
AcONa: Sodium acetate

Scheme 18: Synthesis of 2-22.

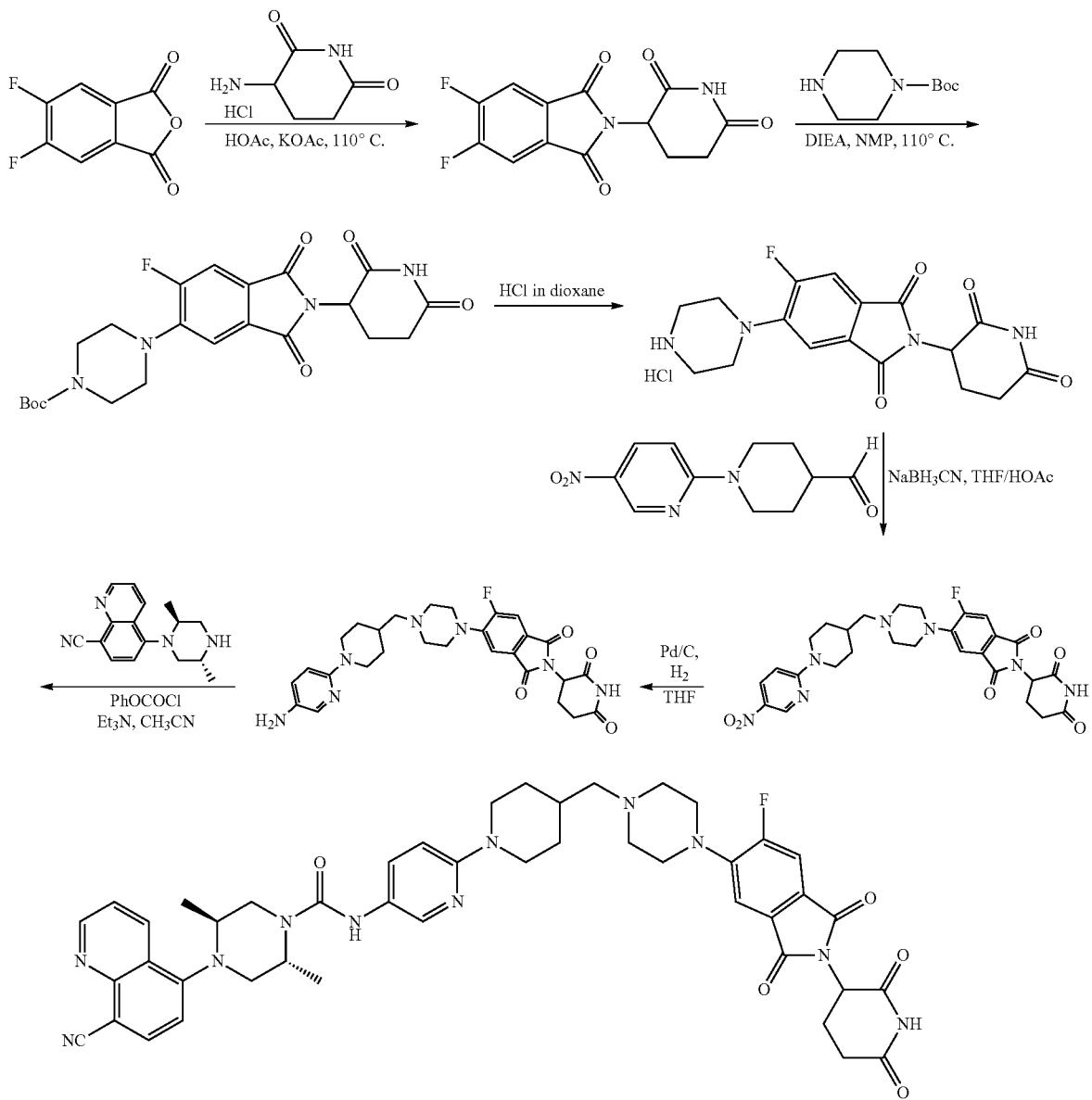

Compounds 2-23 and 2-24 were synthesized using the same method as described in Scheme 18.

Abbreviations

The following abbreviations have the meanings set forth below:
ACN: acetonitrile
EtOAc: ethyl acetate
PE: petroleum ether
TFA: trifluoroacetic acid
AcOH: acetic acid
NaCNBH3: sodium cyanoborohydride
DMAP: 4-dimethylaminopyridine
DMSO: dimethyl sulfoxide
DCM: dichloromethane
TEA: triethylamine
EtOH: ethanol Pd$_2$(dba)$_3$: tri(dibenzylideneacetone)dipalladium
EA: ethyl acetate
S-Phos: 2-dicyclohexylphosphino-2', 6'-dimethoxybiphenyl
Pd/C: palladium on activated carbon TLC: thin layer chromatography Compounds described herein were prepared from commercially available material. Purity of all final compounds were analyzed by HPLC with detection at 214 nM and 254 nM wavelength. All final compounds showed purity greater than 95%. All final compounds were characterized by LC/MS and H-NMR. The following are representative examples demonstrating how the claimed molecules can be made, however, a person of skill in the art would understand that the compounds could be prepared by other synthetic methods.

Preparation of Intermediates

Synthesis of 2-chloro-4-((2S,5R)-2,5-dimethylpiperazin-1-yl)benzonitrile (Intermediate 1-1)

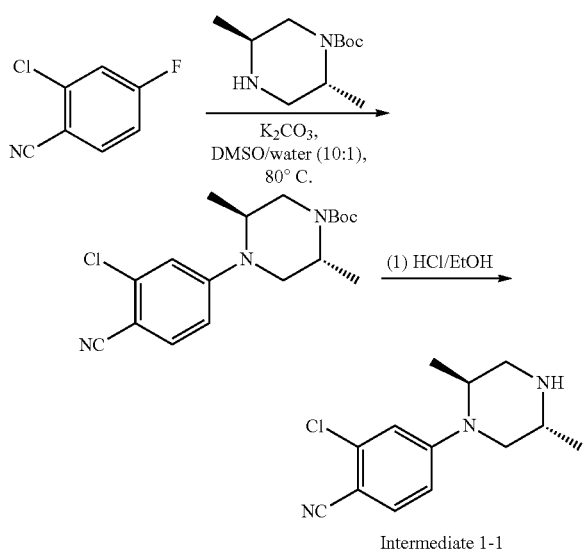

Intermediate 1-1

Step 1: Preparation of tert-butyl (2R,5S)-4-(3-chloro-4-cyanophenyl)-2,5-dimethylpiperazine-1-carboxylate To a solution of 2-chloro-4-fluorobenzonitrile (5 g, 32.14 mmol) in DMSO/Water (10:1, 55 mL) was added K$_2$CO$_3$ (8.9 g, 64.28 mmol) and tert-butyl (2R,5S)-2,5-dimethylpiperazine-1-carboxylate (6.9 g, 32.14 mmol). The reaction mixture was stirred at 80° C. for 12 hours. The mixture was cooled to room temperature, quenched by adding H$_2$O (50 mL), then extracted by EtOAc (100 mL×2). The combined organic layer was washed by brine, dried and concentrated under vacuum to get the crude product, which was purified by flash column chromatography (10% MeOH in DCM) to give the desired product (6.2 g, 55.1%) as a yellow oil. LC/MS: 349.9 [M+H]$^+$; $^1$H NMR (400 MHz, CDCl$_3$) δ 7.47 (d, J=1.2 Hz, 1H), 6.83 (d, J=2.4 Hz, 1H), 6.71 (dd, J=8.8, 2.4 Hz, 1H), 4.55-4.25 (m, 1H), 4.06-3.96 (m, 1H), 3.92-3.77 (m, 1H), 3.44-3.38 (m, 1H), 3.37-3.27 (m, 2H), 1.51 (s, 9H), 1.25 (d, J=6.4 Hz, 3H), 1.17 (d, J=6.4 Hz, 3H).

Step 2: Preparation of 2-chloro-4-((2S,5R)-2,5-dimethylpiperazin-1-yl)benzonitrile Tert-butyl (2R,5S)-4-(3-chloro-4-cyanophenyl)-2,5-dimethylpiperazine-1-carboxylate (6.2 g, 17.72 mmol) was stirred in HCl/EtOH (2 M, 50 mL) at room temperature for 2 hours. After the removal of EtOH, 100 mL of water was added, and the solution was adjusted to pH about 8 with aqueous Na$_2$CO$_3$. The mixture was extracted with EtOAc (100 mL×2). The combined organic layer was washed with brine, dried and concentrated under vacuum to get the crude product, which was purified by flash chromatography (10% MeOH in DCM) to give the desired product (3.8 g, 85.9%) as a yellow oil. LC/MS: 249.9 [M+H]$^+$; $^1$H NMR (400 MHz, CDCl$_3$) δ 7.46 (d, J=4.8 Hz, 1H), 6.87 (d, J=2.4 Hz, 1H), 6.75 (dd, J=8.8, 2.4 Hz, 1H), 3.73-3.67 (m, 1H), 3.35-3.27 (m, 3H), 3.09-3.04 (m, 1H), 2.71 (dd, J=12.8 4.4 Hz, 1H), 1.61 (s, 1H), 1.21 (d, J=4.8 Hz, 3H), 1.19 (d, J=4.8 Hz, 3H).

Synthesis of 2-chloro-4-(trans-2,5-dimethylpiperazin-1-yl)benzonitrile (intermediate 1-2)

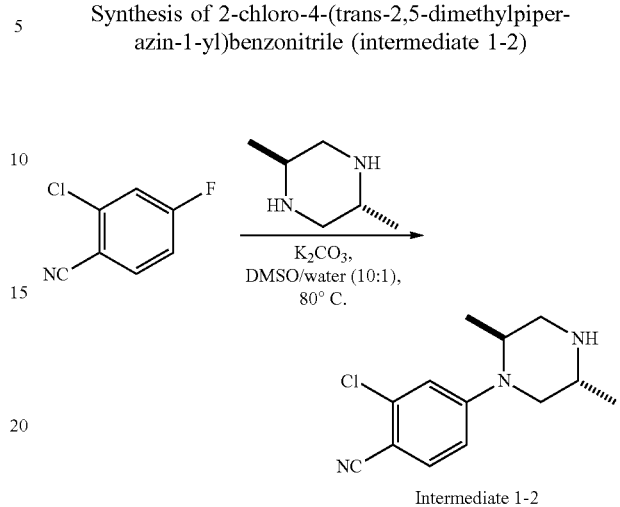

Intermediate 1-2

To a solution of 2-chloro-4-fluorobenzonitrile (1 g, 6.43 mmol) in DMSO/Water (10:1, 11 mL) was added K$_2$CO$_3$ (1.78 g, 12.86 mmol) and trans-2,5-dimethylpiperazine (771 mg, 6.75 mmol). The reaction mixture was stirred at 80° C. for 12 hours. The mixture was cooled to room temperature, quenched with H$_2$O (50 mL), then extracted by EtOAc (100 mL×2). The combined organic layer was washed with brine, dried and concentrated under vacuum to give a crude product, which was purified by silica gel flash column chromatography (10% MeOH in DCM) to give the desired product (540 mg, 31.88%) as a yellow oil. LC/MS: 250.2 [M+H]$^+$; $^1$H NMR (400 MHz, CDCl$_3$) δ 7.47 (d, J=8.8 Hz, 1H), 6.88 (d, J=2.4 Hz, 1H), 6.76 (dd, J=8.8, 2.4 Hz, 1H), 3.75-3.68 (m, 1H), 3.35-3.29 (m, 3H), 3.10-3.05 (m, 1H), 2.72 (dd, J=12.6, 4.4 Hz, 1H), 2.10 (s, 1H), 1.22 (d, J=6.8 Hz, 3H), 1.20 (d, J=6.8 Hz, 3H).

Synthesis of 4-((2S,5R)-2,5-dimethylpiperazin-1-yl)-2-methoxy benzonitrile (Intermediate 1-3)

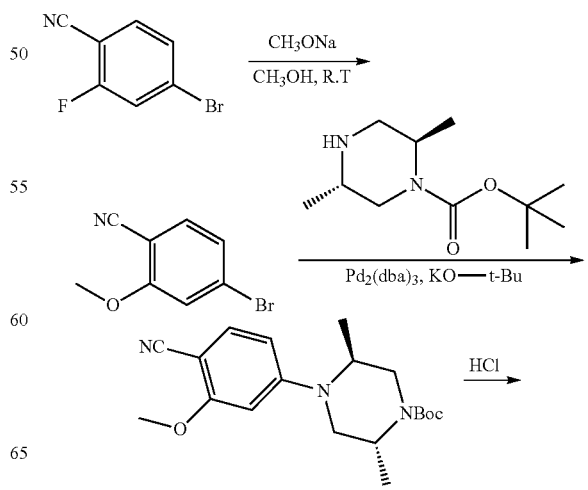

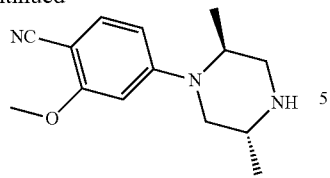

Intermediate 1-3

Step 1: Preparation of 4-bromo-2-methoxybenzonitrile

A mixture of 4-bromo-2-fluorobenzonitrile (5 g, 0.025 mol), CH$_3$ONa (2.7 g, 0.05 mol) and MeOH (100 mL) was stirred at room temperature overnight. The crude product was concentrated and purified via silica gel column chromatography (DCM/MeOH=20:1) to give the title compound (2.4 g, 90% purity, 40%). LC/MS: 211.9 [M+H]$^+$.

Step 2: Preparation of tert-butyl (2R,5S)-4-(4-cyano-3-methoxyphenyl)-2,5-dimethylpiperazine-1-carboxylate To a solution 4-bromo-2-methoxybenzonitrile (1400 mg, 6.6 mmol) in dioxane (50 mL) stirred under argon at room temperature was added tert-butyl (2R,5S)-2,5-dimethylpiperazine-1-carboxylate (1415 mg, 6.6 mmol), Pd$_2$(dba)$_3$ (181 mg, 0.20 mmol), potassium tert-butoxide (1481 mg, 13.2 mmol) and S-Phos (89 mg, 0.06 mmol). The reaction mixture was stirred at room temperature for 3 hours. The crude product was purified via silica gel column chromatography (DCM/MeOH=20:1) to give the title compound (550 mg, 24%). LC/MS: 346.21[M+H]t Step 3: Preparation of 4-((2S,5R)-2,5-dimethylpiperazin-1-yl)-2-methoxy benzonitrile (Intermediate 1-3)

To a solution of tert-butyl (2R,5S)-4-(4-cyano-3-methoxyphenyl)-2,5-dimethylpiperazine-1-carboxylate (90 mg, 0.26 mmol) in DCM (20 mL) stirred under argon at room temperature was added TFA (90 mg, 0.78 mmol). The reaction mixture was stirred at room temperature for 2 hours. The crude product was concentrated in vacuum to give the title compound as TFA salt (70 mg, 88%). LC/MS: 246.15 [M+H]$^+$.

Synthesis of 4-((2S,5R)-2,5-dimethylpiperazin-1-yl)-2-(trifluoromethyl)benzonitrile hydrochloride (Intermediate 1-4)

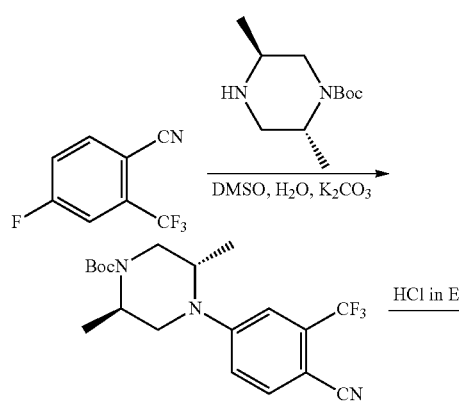

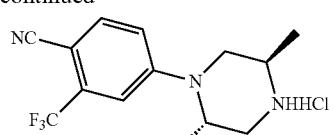

Intermediate 1-4

To a solution of 4-fluoro-2-(trifluoromethyl)benzonitrile (441 mg, 2.33 mmol), tert-butyl (2R,5S)-2,5-dimethylpiperazine-1-carboxylate (500 mg, 2.33 mmol)) in DMSO/H$_2$O (20 mL/10 mL) was added K$_2$CO$_3$ (644 mg, 4.66 mmol). The reaction mixture was stirred at 80° C. for overnight. The reaction mixture was cooled to room temperature and diluted with H$_2$O (20 mL), then extracted with EA (20 mL×3), dried over Na$_2$SO$_4$ and concentrated in vacuum to give a crude product. The crude product was purified by silica gel chromatography (PE:EA=5:1) to give tert-butyl (2R,5S)-4-(4-cyano-3-(trifluoromethyl)phenyl)-2,5-dimethylpiperazine-1-carboxylate (804 mg, 90%). LC/MS: 384.1 [M+H]$^+$. This product (804 mg, 2.09 mmol) in EtOH (20 mL) was bubbled with HCl (g) for 10 minutes. The reaction mixture was stirred at room temperature for 2 hours. The solvent was removed in vacuum to give a crude product. The crude product was washed with EA (5 mL×3) and dried in vacuum to give the title compound (287 mg, 43%) as a hydrochloride salt. LC/MS: 283.9 [M+H]$^+$; $^1$H NMR (400 MHz, MeOD) δ 7.84 (d, J=8.7 Hz, 1H), 7.40 (d, J=2.4 Hz, 1H), 7.34 (dd, J=8.7, 2.5 Hz, 1H), 4.38-4.28 (m, 1H), 3.83-3.80 (m, 1H), 3.67-3.57 (m, 3H), 3.23-3.19 (dd, J=13.3, 4.6 Hz, 1H), 1.45 (d, J=6.8 Hz, 3H), 1.31 (d, J=6.7 Hz, 3H).

Synthesis of 5-((2S,5R)-2,5-dimethylpiperazin-1-yl)quinoline-8-carbonitrile (Intermediate 1-5)

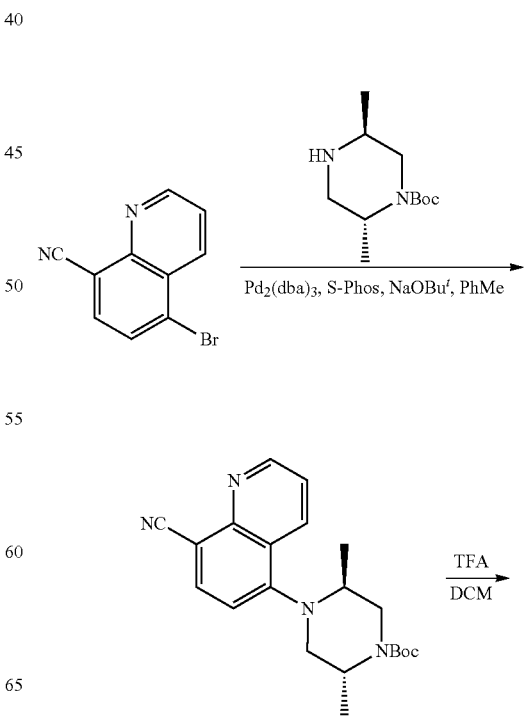

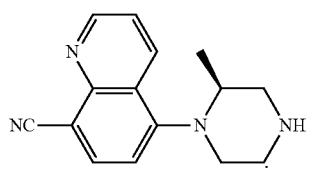

Intermediate 1-5

To a solution of 5-bromoquinoline-8-carbonitrile (1.3 g, 5.6 mmol) and tert-butyl (2R,5S)-2,5-dimethylpiperazine-1-carboxylate (1 g, 4.67 mmol) in toluene (25 mL) stirred under nitrogen at room temperature was added S-phos (192 mg, 0.467 mmol), Pd$_2$(dba)$_3$ (268 mg, 0.467 mmol) and t-BuONa (672 mg, 7 mmol). The reaction mixture was stirred at room temperature for 4 hours. The solvent was removed in vacuum to give a crude product which was purified by silica gel column chromatography (0-15% MeOH in DCM) to give tert-butyl (2R,5S)-4-(8-cyanoquinolin-5-yl)-2,5-dimethylpiperazine-1-carboxylate (1.2 g, 58%). LC/MS: 366.9 [M+H]$^+$. This product (1.2 g, 3.27 mmol) in DCM (21 mL) was treated with trifluoroacetic acid (7 mL) and the mixture was stirred at room temperature for 5 h. The solvent was removed in vacuum to give the title compound (860 mg, 100%). LC/MS: 266.9 [M+H]$^+$; $^1$H NMR (400 MHz, DMSO) δ 9.56 (d, J=9.1 Hz, 1H), 9.24 (d, J=10.0 Hz, 1H), 9.10 (dd, J=4.2, 1.7 Hz, 1H), 8.85 (dd, J=8.6, 1.7 Hz, 1H), 8.38 (dd, J=7.5, 4.3 Hz, 1H), 7.74 (dd, J=8.6, 4.2 Hz, 1H), 7.57 (d, J=8.0 Hz, 1H), 3.76-3.58 (m, 2H), 3.53 (d, J=10.7 Hz, 1H), 3.28-3.18 (m, 1H), 3.01 (q, J=10.6 Hz, 1H), 2.86-2.71 (m, 1H), 1.23 (d, J=6.5 Hz, 3H), 0.88 (d, J=6.1 Hz, 3H).

Synthesis of 2-(2,6-dioxopiperidin-3-yl)-5-(piperazin-1-yl)isoindoline-1,3-dione (Intermediate 2-1)

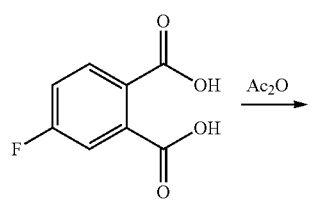

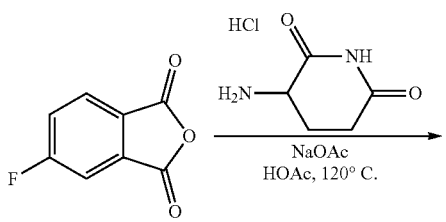

Intermediate 2-1

Intermediate 2-1 was prepared according to the above scheme as a hydrochloride salt using a similar method described in the literature. LC/MS 343.1 [M+H]$^+$; $^1$H-NMR (400 MHz, CD$_3$OD) δ ppm 7.76 (d, J=8.36 Hz, 1H), 7.47 (s, 1H), 7.35 (dd, J=8.36, 1.54 Hz, 1H), 5.09 (br dd, J=12.8, 5.40 Hz, 1H), 3.67-3.74 (m, 4H), 3.37-3.42 (m, 4H), 2.63-2.94 (m, 3H), 2.07-2.17 (m, 1H).

Synthesis of (S)-3-(1-oxo-5-(piperazin-1-yl)isoindolin-2-yl)piperidine-2,6-dione (Intermediate 2-2)

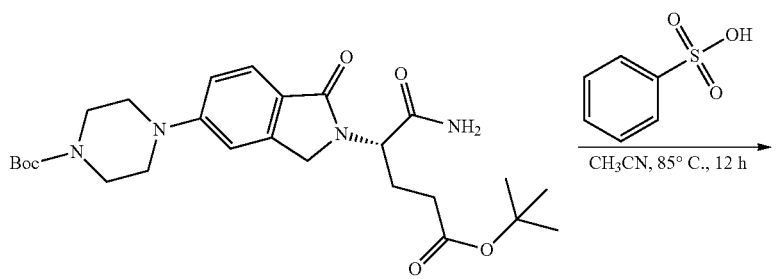

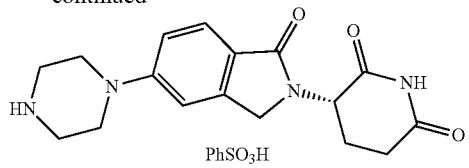

Intermediate 2-2

To a solution of (S)-tert-butyl 4-(2-(1-amino-5-tert-butoxy-1,5-dioxopentan-2-yl)-1-oxoisoindolin-5-yl)piperazine-1-carboxylate (5.8 g, 12 mol) in acetonitrile (90 mL) was added benzenesulfonic acid (3.64 g, 23 mol). The mixture was stirred at 85° C. for 12 h. LC/MS showed the reaction was complete. The mixture was concentrated in vacuum. The residue was triturated with ethyl acetate to afford (S)-3-(1-oxo-5-(piperazin-1-yl)isoindolin-2-yl)piperidine-2,6-dione benzenesulfonate (5.2 g, 93%) as off-white solid. LC/MS 329.1 [M+1]$^+$; $^1$H NMR (400 MHz, DMSO-d6) δ 1.95-1.99 (m, 1H), 2.36-2.41 (m, 1H), 2.58-2.62 (d, 1H), 2.88-2.91 (m, 1H), 3.26 (s, 4H), 3.49-3.52 (m, 4H), 4.21-4.38 (dd, 2H), 5.05-5.10 (dd, 1H), 7.12-7.16 (m, 2H), 7.30-7.358 (m, 3H), 7.58-7.62 (m, 3H), 8.72 (s, 2H).

Synthesis of 2-(2,6-dioxopiperidin-3-yl)-5-fluoro-6-(piperazin-1-yl)isoindoline-1,3-dione (Intermediate 2-3)

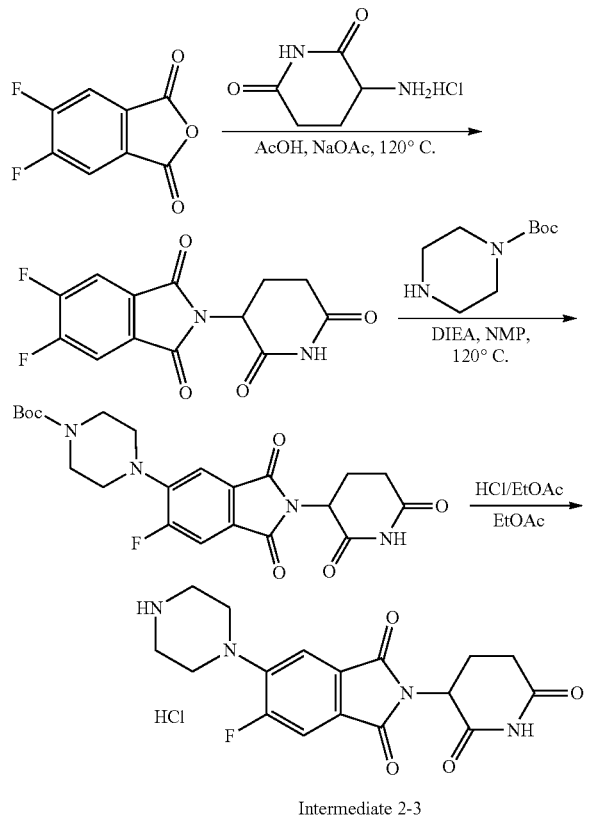

Intermediate 2-3

Intermediate 2-3 was prepared using the similar method as Intermediate 2-1 as a hydrochloride salt. LC/MS 361.1 [M+1]$^+$; $^1$H NMR (400 MHz, DMSO-d6) δ 11.1 (s, 1H), 9.49 (br s, 2H), 7.79 (d, J=11.2 Hz, 1H), 7.57 (br d, J=7.32 Hz, 1H), 5.12 (br dd, J=12.4, 5.32 Hz, 1H), 3.50 (br s, 4H), 3.24 (br s, 4H), 2.80-2.95 (m, 1H), 2.52-2.69 (m, 2H), 1.97-2.10 (m, 1H).

Synthesis of (S)-3-(6-fluoro-1-oxo-5-(piperazin-1-yl)isoindolin-2-yl)piperidine-2,6-dione (Intermediate 2-4)

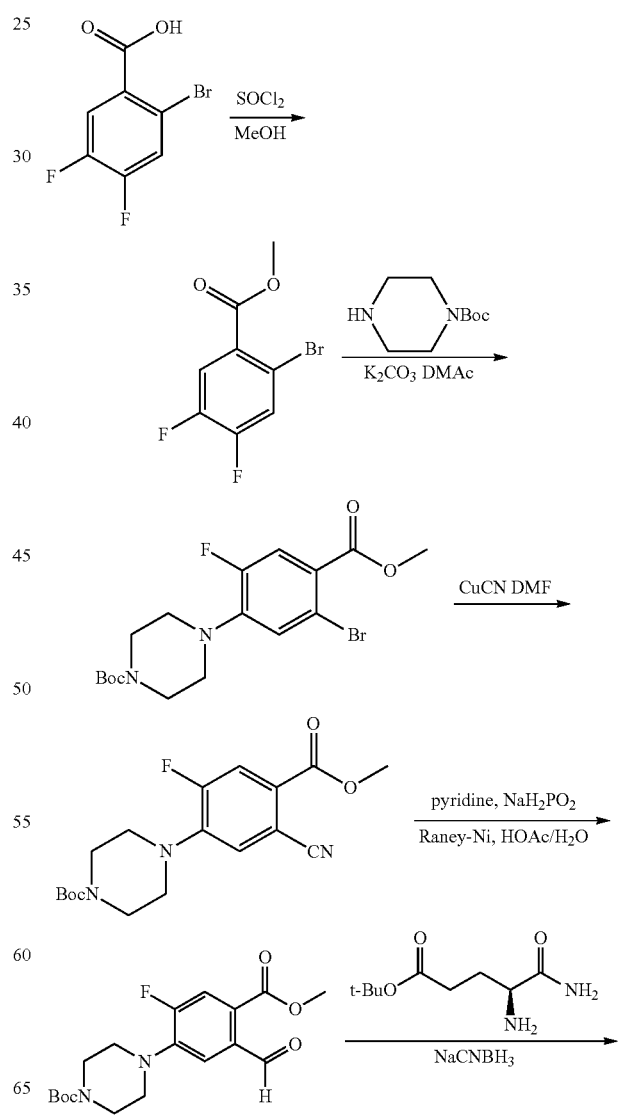

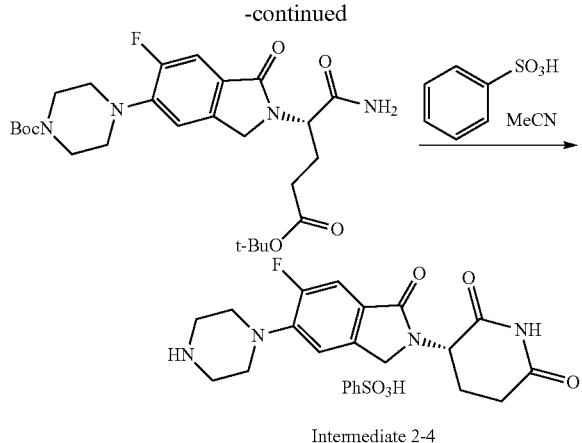

Intermediate 2-4

Step 1: Preparation of methyl 2-bromo-4,5-difluorobenzoate

Thionyl chloride (130 g, 1.09 mol) was added slowly to a mixture of 2-bromo-4,5-difluorobenzoic acid (200 g, 0.84 mol) in MeOH (600 mL) at 10° C., the mixture was stirred at 80° C. for 3 h. TLC showed the reaction was completed. The mixture was cooled to room temperature, concentrated, then partitioned between ethyl acetate and water. The organic layer was washed with saturated $Na_2CO_3$ and brine twice, dried over $Na_2SO_4$ and concentrated to afford a crude methyl 2-bromo-4,5-difluorobenzoate (210 g, yield: 100%) which was used for the next step without further purification.

Step 2: Preparation of tert-butyl 4-(5-bromo-2-fluoro-4-(methoxycarbonyl)phenyl) piperazine-1-carboxylate A mixture of methyl 2-bromo-4,5-difluorobenzoate (210 g, 0.84 mol), tert-butyl piperazine-1-carboxylate (234 g, 1.25 mol) and $K_2CO_3$ (173 g, 1.25 mol) in N,N-dimethylacetamide (600 mL) was stirred at 80° C. for 16 h. TLC showed the reaction was completed. The mixture was added to water (2 L) and stirred for 10 min followed by the addition of ethyl acetate. The mixture was partitioned between ethyl acetate and water. The organic layer was washed with water, brine, dried over $Na_2SO_4$ and concentrated to afford tert-butyl 4-(5-bromo-2-fluoro-4-(methoxycarbonyl)phenyl)piperazine-1-carboxylate (315.8 g, yield: 90%).

Step 3: Preparation of tert-butyl 4-(5-cyano-2-fluoro-4-(methoxycarbonyl)phenyl) piperazine-1-carboxylate A mixture of tert-butyl 4-(5-bromo-2-fluoro-4-(methoxycarbonyl)phenyl)piperazine-1-carboxylate (306 g, 0.73 mol) and CuCN (98 g, 1.09 mol) in DMF (1.2 L) was stirred at 100° C. for 16 h. TLC showed the reaction was completed. The mixture was cooled to room temperature. Ethyl acetate (2 L) and ammonium hydroxide (2 L) were added and the mixture was stirred for 30 min. The mixture was filtered. The organic layer was washed with water, dried over $Na_2SO_4$ and concentrated to afford a crude product (254 g). This crude product was taken into petroleum ether (1 L) at reflux. The mixture was filtered and dried in oven at 50° C. to afford tert-butyl 4-(5-cyano-2-fluoro-4-(methoxycarbonyl)phenyl)piperazine-1-carboxylate (215 g, yield: 81%).

Step 4: Preparation of tert-butyl 4-(2-fluoro-5-formyl-4-(methoxycarbonyl)phenyl) piperazine-1-carboxylate To a solution of pyridine (391 g, 4.95 mol), water (200 mL), acetic acid (264 g, 4.4 mol) was added tert-butyl 4-(5-cyano-2-fluoro-4-(methoxycarbonyl)phenyl)piperazine-1-carboxylate (200 g, 0.55 mol) and Raney-nickel (85% in water, 100 g) at room temperature. The resulting mixture was heated to 60° C. Sodium hypophosphite (292 g in 500 mL water) was added dropwise into the mixture. The mixture was stirred for 16 h at 60° C. TLC showed the reaction not completed. The mixture was further stirred for 10 h. The mixture was cooled to room temperature. Ethyl acetate and water were added. The mixture was filtered. The organic layer was washed with water, 1N HCl and brine, dried over $Na_2SO_4$ and concentrated under reduced pressure to afford a crude product (208 g, crude) which was further purified by silica-gel pad to provide 4-(2-fluoro-5-formyl-4-(methoxycarbonyl)phenyl)piperazine-1-carboxylate (86.5 g, yield: 43%).

Step 5: Preparation of tert-butyl (S)-4-(2-(1-amino-5-(tert-butoxy)-1,5-dioxopentan-2-yl)-6-fluoro-1-oxoisoindolin-5-yl)piperazine-1-carboxylate To a solution of tert-butyl 4-(2-fluoro-5-formyl-4-(methoxycarbonyl)phenyl)piperazine-1-carboxylate (81.5 g, 0.22 mol) in methanol (500 mL) was added tert-butyl (S)-4,5-diamino-5-oxopentanoate (54 g, 0.27 mol) at room temperature. Acetic acid (19.8 g, 0.33 mol) was added at 0° C. followed by the addition of sodium cyanoborohydride (27.6 g, 0.44 mol) slowly. The mixture was stirred at room temperature for 16 hours. TLC showed the reaction was completed. The mixture was concentrated and partitioned between ethyl acetate and water. The organic layer was washed with saturated citric acid, brine, dried over $Na_2SO_4$ and concentrated under reduced pressure to afford a crude product which was further purified by silica-gel pad to give tert-butyl (S)-4-(2-(1-amino-5-(tert-butoxy)-1,5-dioxopentan-2-yl)-6-fluoro-1-oxoisoindolin-5-yl)piperazine-1-carboxylate (80 g, yield: 69%).

Step 6: Preparation of (S)-3-(6-fluoro-1-oxo-5-(piperazin-1-yl)isoindolin-2-yl)piperidine-2,6-dione benzenesulfonic acid (Intermediate 2-4)

To a solution of (S)-4-(2-(1-amino-5-(tert-butoxy)-1,5-dioxopentan-2-yl)-6-fluoro-1-oxoisoindolin-5-yl)piperazine-1-carboxylate (67 g, 0.13 mol) in acetonitrile (670 mL) was added benzenesulfonic acid (43 g, 0.26 mol). The mixture was stirred at 80° C. for 16 h. LCMS showed the reaction was complete. The mixture was cooled to room temperature. The mixture was filtered and dried to afford (S)-3-(6-fluoro-1-oxo-5-(piperazin-1-yl)isoindolin-2-yl)piperidine-2,6-dione benzenesulfonic acid (56 g, 86%) as off-white solid. $^1$H NMR (400 MHz, DMSO-d6) δ 1.94-1.99 (m, 1H), 2.35-2.43 (m, 1H), 2.58-2.62 (m, 1H), 2.88-2.91 (m, 1H), 3.30 (br s, 8H), 4.38 (d, J=17.2 Hz, 1H), 4.26 (d, J=17.2 Hz, 1H), 5.08 (dd, J=13.2, 5.2 Hz, 1H), 7.29-7.35 (m, 4H), 7.49 (d, J=8.7 Hz, 1H), 7.60 (m, 2H), 8.72 (br s, 2H), 10.99 (s, 1H). LCMS m/z 347.3 [M+1]$^+$.

Preparation of Example Compounds
Synthesis of (2R,5S)-4-(3-chloro-4-cyanophenyl)-N-(6-(4-(((1r,3r)-3((2-(2,6-dioxopiperidin-3-yl)-1,3-dioxoisoindolin-5-yl)oxy)cyclobutyl)(methyl)amino)butoxy)pyridin-3-yl)-2,5-dimethylpiperazine-1-carboxamide (1-8)
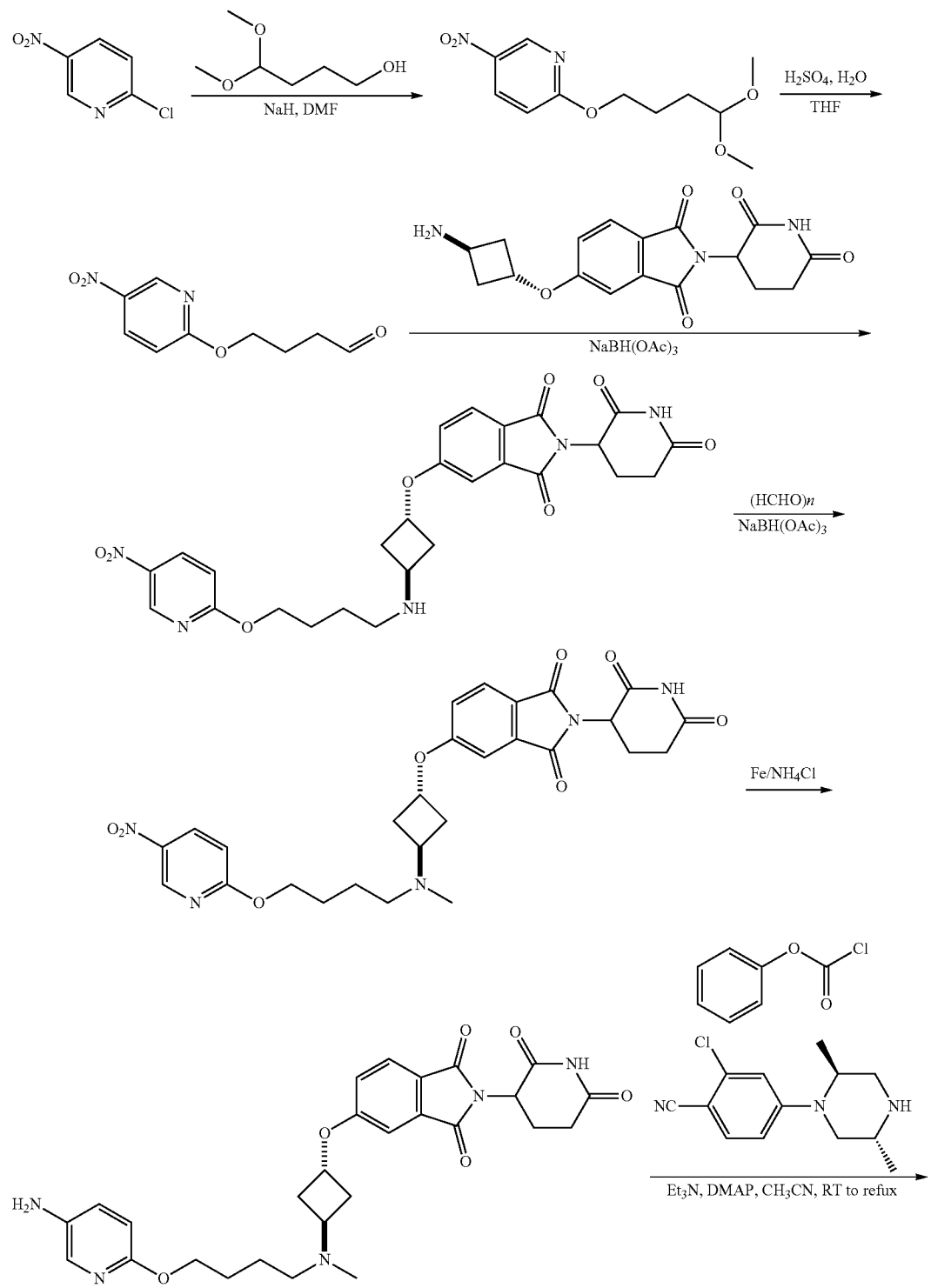

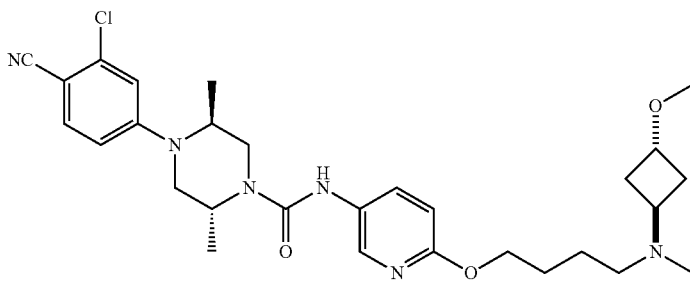
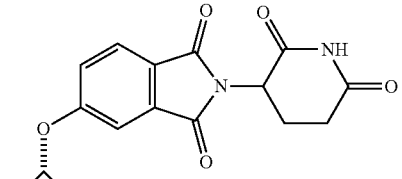

1-8

Step 1: Preparation of 2-(4,4-dimethoxybutoxy)-5-nitropyridine

The NaH (0.36 g, 15.19 mmol) was added in a mixture of THF (30 mL) and 4,4-dimethoxybutan-1-ol (1.7 g, 12.7 mmol) at 0° C. After 30 minutes, 2-chloro-5-nitropyridine (1 g, 6.33 mmol) was added. The reaction mixture was stirred at room temperature for 2 hours. The reaction mixture was quenched with water and the PH was adjusted to 6-7, and the mixture was concentrated under reduced pressure. The residue was purified with flash column chromatography using PE/EA=5/1 to afford the product 2-(4,4-dimethoxybutoxy)-5-nitropyridine (0.5 g, 1.95 mmol, 30.8%) as a white solid. LC/MS: 224.9 [M+H–31]+.

Step 2: Preparation of 4-((5-nitropyridin-2-yl)oxy)butanal

A mixture of 2-(4,4-dimethoxybutoxy)-5-nitropyridine (500 mg, 1.95 mmol) in 2M $H_2SO_4$ (10 mL) was stirred at 70° C. for 1 hour. The reaction was diluted with $NaHCO_3$ and extracted with EA. The organic part was concentrated to afford the desired product (400 mg, 1.90 mmol, 97.5%) as a white solid. This product was directly used in the next step without any further purification. LC/MS: 211.0 [M+H]+.

Step 3: Preparation of 2-(2,6-dioxopiperidin-3-yl)-5-((1r,3r)-3-((4-((5-nitropyridin-2-yl)oxy)butyl)amino)cyclobutoxy)isoindoline-1,3-dione To a solution of 4-((5-nitropyridin-2-yl)oxy)butanal (400 mg, 1.9 mmol) and 5-((1r,3r)-3-aminocyclobutoxy)-2-(2,6-dioxopiperidin-3-yl)isoindoline-1,3-dione(651.7 mg, 1.9 mmol) in dry THF (20 mL) was added NaBH(OAc)$_3$ (483.2 mg, 2.28 mmol). The mixture was stirred at 25° C. for 48 hours. The mixture was diluted with DCM and washed with water for 3 times. The organic layer was dried and concentrated. The residue was purified by flash column chromatography eluted with DCM/MeOH (20:1) to afford the desired (360 mg, 0.67 mmol, 35.3%) as a white solid. LC/MS: 538.3 [M+H]+.

Step 4: Preparation of 2-(2,6-dioxopiperidin-3-yl)-5-((1r,3r)-3-(methyl(4-((5-nitropyridin-2-yl)oxy)butyl)amino)cyclobutoxy)isoindoline-1,3-dione The above solid (360 mg, 0.67 mmol) and HCHO (1 mL) were dissolved in DCM (10 mL). Then NaBH(OAc)$_3$ (211.9 mg, 1.0 mmol) was added. The mixture was stirred at room temperature for 2 hours. The reaction mixture was washed with water and the organic phase was dried and concentrated. The residue was directly used without further purification. The product was obtained as a white solid (356 mg, 0.65 mmol, 97.0%). LC/MS: 551.7[M+H]+

Step 5: Preparation of 5-((1r,3r)-3-((4-((5-aminopyridin-2-yl)oxy)butyl)(methyl)amino)cyclobutoxy)-2-(2,6-dioxopiperidin-3-yl)isoindoline-1,3-dione The above white solid (356 mg, 0.65 mmol) was dissolved in EtOH (20 mL). Then Fe (181 mg, 3.25 mmol), NH$_4$Cl (173.84 mg, 3.25 mmol), and water (2 mL) were added. The mixture was stirred at 90° C. for 16 hours. The reaction mixture was filtered, and the filtrate was concentrated to afford the desired product as a white solid without further purification. (300 mg, 0.57 mmol, 88.5%). LC/MS: 522.1 [M+H]+.

Step 6: Preparation (2R,5S)-4-(3-chloro-4-cyanophenyl)-N-(6-(4-(((1r,3r)-3-((2-(2,6-dioxopiperidin-3-yl)-1,3-dioxoisoindolin-5-yl)oxy)cyclobutyl)(methyl)amino)butoxy)pyridin-3-yl)-2,5-dimethylpiperazine-1-carboxamide (1-8)

The above amine (60 mg, 0.12 mmol), phenyl carbonochloridate(18.87 mg, 0.12 mmol), DMAP (1.4 mg, 0.012) and triethylamine (14.5 mg, 0.14 mmol) was stirred in MeCN (10 mL) at 25° C. for 2 hours. The reaction solution was concentrated and washed with water. Then the intermediate was dissolved in MeCN and 2-chloro-4-((2S,5R)-2,5-dimethylpiperazin-1-yl)benzonitrile (29.9 mg, 0.12 mmol) was added. The mixture was stirred at 80° C. for 16 hours. The reaction was concentrated and purified by flash column chromatography eluted with DCM/MeOH(15:1) to afford the desired product (20 mg, 0.025 mmol, 20.8%) as a yellow solid. LC/MS: 797.3 [M+H]+; $^1$H NMR (400 MHz, DMSO) δ 11.12 (s, 1H), 8.56 (s, 1H), 8.18 (d, J=2.6 Hz, 1H), 7.85 (d, J=8.5 Hz, 1H), 7.77 (dd, J=8.9, 2.6 Hz, 1H), 7.67 (d, J=9.0 Hz, 1H), 7.34-7.14 (m, 3H), 7.00 (dd, J=9.1, 2.3 Hz, 1H), 6.73 (d, J=8.8 Hz, 1H), 5.17-4.95 (m, 2H), 4.50-4.41 (m, 1H), 4.37-4.15 (m, 3H), 3.85 (d, J=13.7 Hz, 1H), 3.66 (d, J=12.1 Hz, 1H), 3.41-3.35 (m, 1H), 3.33-3.28 (m, 2H), 2.96-2.78 (m, 2H), 2.73-2.53 (m, 3H), 2.46-2.16 (m, 4H), 2.15-1.88 (m, 3H), 1.72 (s, 5H), 1.16 (d, J=6.6 Hz, 3H), 1.09 (d, J=6.5 Hz, 3H).

Synthesis of (2R,5S)-4-(3-chloro-4-cyanophenyl)-N-(6-(4-((4-(2-(2,6-dioxopiperidin-3-yl)-1,3-dioxoi-soindolin-5-yl)piperazin-1-yl)methyl)piperidin-1-yl)pyridin-3-yl)-2,5-dimethylpiperazine-1-carboxamide (1-14)
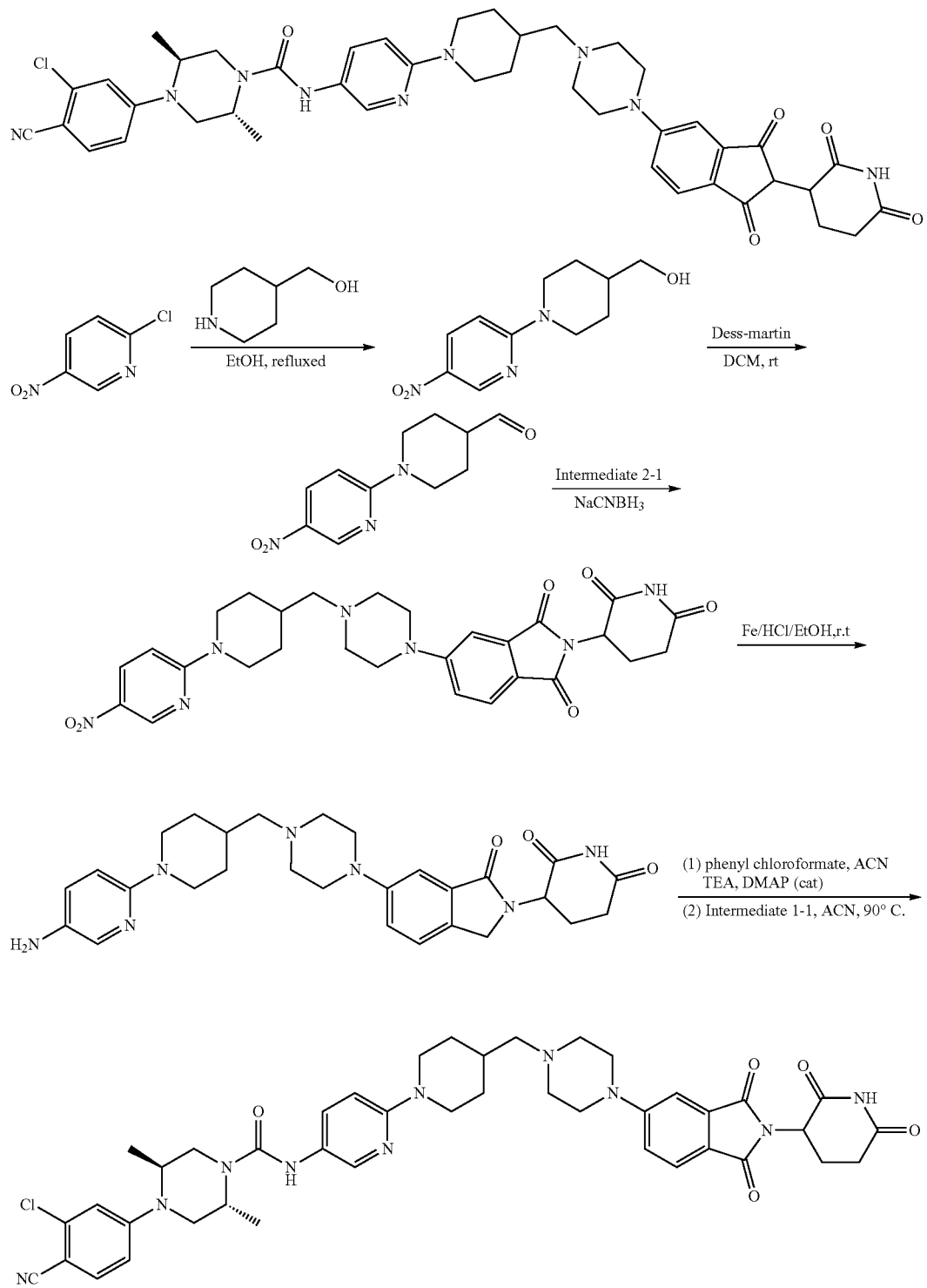
1-14

Step 1: Preparation of (1-(5-nitropyridin-2-yl)piperidin-4-yl)methanol

To a solution of 2-chloro-5-nitropyridine (5 g, 31.5 mmol) in EtOH (50 mL) stirred at room temperature was added piperidin-4-ylmethanol (3.63 g, 31.5 mmol). The reaction mixture was stirred at 80° C. for 2 hours. After the reaction completion, the mixture was cooled to room temperature and concentrated under vacuum. The residue was purified by flash column chromatography on silica gel (PE/EtOAc=3:1) to afford the desired product (3.77 g, 50.4%) as a yellow solid. LC/MS: 238.0 [M+H]$^+$; $^1$H NMR (400 MHz, CDCl$_3$) δ=9.05 (d, J=2.8 Hz, 1H), 8.20 (dd, J=9.6, 2.8 Hz, 1H), 6.60 (d, J=9.6 Hz, 1H), 4.59 (d, J=12.8 Hz, 2H), 3.57 (d, J=5.6 Hz, 2H), 3.05 (t, J=12.8 Hz, 2H), 1.97-1.90 (m, 2H), 1.90-1.84 (m, 1H), 1.37-1.24 (m, 2H).

Step 2: Preparation of 1-(5-nitropyridin-2-yl)piperidine-4-carbaldehyde

To a solution of (1-(5-nitropyridin-2-yl)piperidin-4-yl)methanol (3.77 g, 15.9 mmol) in DCM (40 mL) stirred at room temperature was added Dess-Martin reagent (1.35 g, 31.8 mmol). The mixture was stirred at room temperature for 2 hours. The reaction was quenched by the addition of saturated sodium sulfite solution, the solid was filtered out, the organic layer was washed with brine, dried over Na$_2$SO$_4$, filtered and concentrated under vacuum. The crude product was used in next step without further purification (3 g, 80.2%). LC/MS: 236.0 [M+H]$^+$.

Step 3: Preparation of 2-(2,6-dioxopiperidin-3-yl)-5-(4-((1-(5-nitropyridin-2-yl)piperidin-4-yl)methyl)piperazin-1-yl)isoindoline-1,3-dione To a solution of Intermediate 2-1 (1.61 g, 4.25 mmol) in DCM/MeOH (13 mL, 10:3) stirred at 15° C. was added AcONa (523 mg, 6.375 mmol). After 30 minutes of stirring, AcOH (510 mg, 8.5 mmol) was added, then 1-(5-nitropyridin-2-yl)piperidine-4-carbaldehyde (1 g, 4.25 mmol) was added. The mixture was stirred at 15° C. for 30 minutes, then NaCNBH$_3$ (400 mg, 6.375 mmol) was added. The reaction mixture was stirred at 15° C. for 1 hour. LC/MS showed the reaction completed. The mixture was quenched with 30 mL of water, extracted with DCM (30 mL×2). The combined organic layer was washed with brine, dried and concentrated under vacuum to give the crude product, which was purified by preparative TLC (DCM/MeOH=10:1) to afford the desired compound (500 mg, 20.9%) as a yellow solid. LC/MS: 561.9 [M+H]$^+$.

Step 4: Preparation of 5-(4-((1-(5-aminopyridin-2-yl)piperidin-4-yl)methyl)piperazin-1-yl)-2-(2,6-dioxopiperidin-3-yl)isoindoline-1,3-dione To a stirred solution of 2-(2,6-dioxopiperidin-3-yl)-5-(4-((1-(5-nitropyridin-2-yl)piperidin-4-yl)methyl)piperazin-1-yl)isoindoline-1,3-dione (500 mg, 0.89 mmol) in THF (5 mL) was added Pd/C (dry, 50 mg), and the mixture was stirred under H$_2$ (0.4 MPa) at 60° C. for 12 hours. After the reaction completed, the mixture was filtered, and the filtrate was concentrated under vacuum to give a crude product, which was purified by preparative TLC (DCM/MeOH=10:1) to afford the desired compound (160 mg, 33.9%) as a yellow solid. LC/MS: 531.9 [M+H]$^+$.

Step 5: Preparation of (2R,5S)-4-(3-chloro-4-cyanophenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide (1-14)

To a solution of 5-(4-((1-(5-aminopyridin-2-yl)piperidin-4-yl)methyl)piperazin-1-yl)-2-(2,6-dioxopiperidin-3-yl)isoindoline-1,3-dione (160 mg, 0.3 mmol) containing phenyl chloroformate (67 mg, 0.33 mmol), and TEA (33 mg, 0.33 mmol) in ACN (10 mL) was added DMAP (1.3 mg, 0.01 mmol). The reaction mixture was stirred at r.t for 2 h and then quenched by adding water (2 mL). Solvent was removed under vacuum and the residue was dissolved in ACN (10 mL). Then 2-chloro-4-((2S,5R)-2,5-dimethylpiperazin-1-yl)benzonitrile (75 mg, 0.3 mmol) was added. The reaction mixture was stirred at 90° C. overnight. The mixture was concentrated under vacuum to give a crude product, and the crude product was purified by preparative TLC (MeOH:DCM=1:10) to give the title compound (80 mg, 33%). LC/MS: 806.6 [M+H]$^+$; $^1$H NMR (400 MHz, DMSO) δ 11.10 (s, 1H), 8.38 (s, 1H), 8.13 (s, 1H), 7.75-7.65 (m, 2H), 7.58 (d, J=2.4 Hz, 1H), 7.37 (s, 1H), 7.28 (s, 1H), 7.17 (s, 1H), 7.0 (d, J=2.4 Hz, 1H), 6.78 (d, J=2.4 Hz, 1H), 5.08 (dd, J=12.0, 4.0 Hz, 1H), 4.44 (br, 1H), 4.27 (br, 1H), 4.18 (d, J=3.6 HZ, 2H), 4.11 (br, 1H), 3.84 (d, J=2.4 Hz, 1H), 3.62 (d, J=2.4 Hz, 1H), 3.4 (br s, 4H), 3.29 (br, 2H), 3.17 (br, 2H), 2.91-2.83 (m, 2H), 2.80-2.71 (m, 2H), 2.54-2.43 (m, 2H), 2.2 (br, 2H), 1.91 (br, 2H), 1.78 (d, J=2.4 Hz, 2H), 1.23 (s, 2H), 1.15 (d, J=1.2 Hz, 3H), 1.08 (d, J=1.2 Hz, 3H).

Synthesis of (2R,5S)-4-(3-chloro-4-cyanophenyl)-N-(6-(4-(2-(4-(2-(2,6-dioxopiperidin-3-yl)-1,3-dioxoisoindolin-5-yl)piperazin-1-yl)ethyl)piperidin-1-yl)pyridin-3-yl)-2,5-dimethylpiperazine-1-carboxamide (1-19)

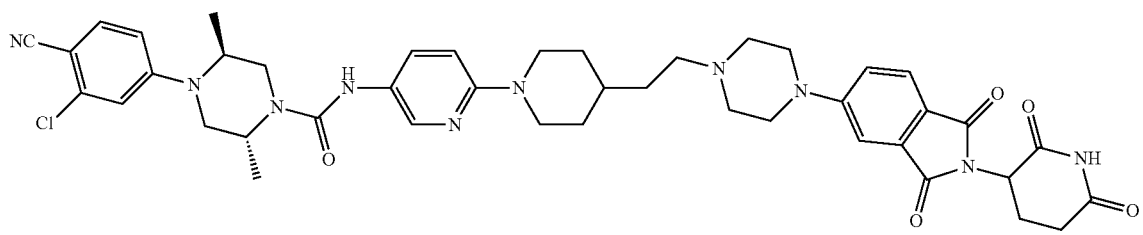 [SMILES: C[C@@H]1CN(c2ccc(C#N)c(Cl)c2)[C@@H](C)CN1C(=O)Nc1ccc(N2CCC(CCN3CCN(c4ccc5c(c4)C(=O)N(C4CCC(=O)NC4=O)C5=O)CC3)CC2)nc1]

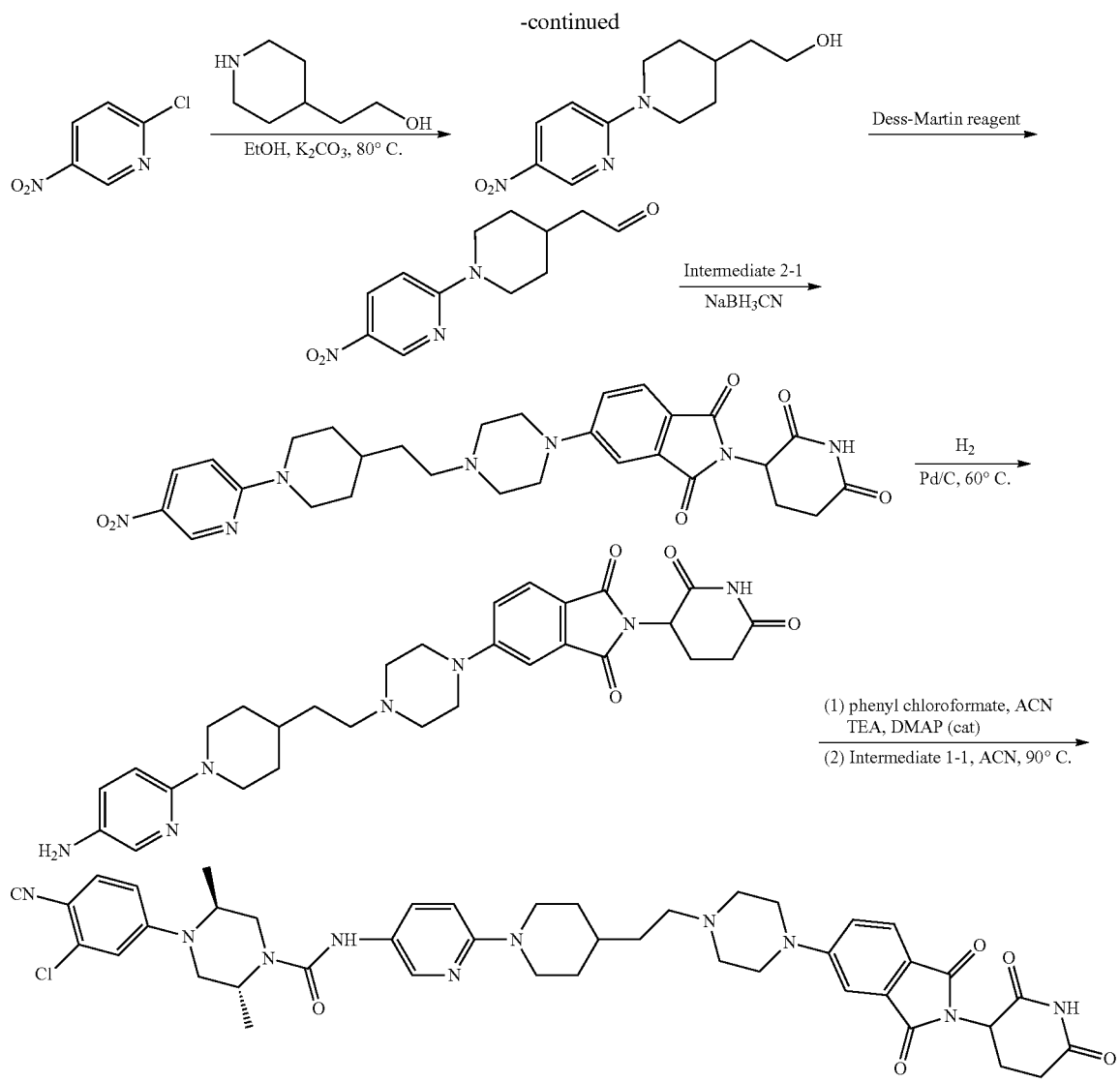

1-19

Step 1: Preparation of 2-(1-(5-nitropyridin-2-yl)piperidin-4-yl)ethan-1-ol

To a solution 2-chloro-5-nitropyridine (800 mg, 5.04 mmol) in EtOH (30 mL) stirred under argon at room temperature was added 2-(piperidin-4-yl) ethanol (652 mg, 5.04 mmol) and K$_2$CO$_3$ (2092 mg, 15.14 mmol). The reaction mixture was stirred at 80° C. for 12 hours. The crude product was purified via silica gel column chromatography (DCM/MeOH=20:1) to give the title compound (1100 mg, 86%). LC/MS: 252.2 [M+H]$^+$.

Step 2: Preparation of 2-(1-(5-nitropyridin-2-yl)piperidin-4-yl)acetaldehyde To a solution of 2-[1-(5-nitropyridin-2-yl) piperidin-4-yl] ethanol (1185 mg, 4.72 mmol) in DCM (10 mL) stirred under argon at room temperature was added Dess-Martin periodinane (4 g, 9.44 mmol). The reaction mixture was stirred at room temperature for 5 hours. The crude product was purified via silica gel column chromatography (DCM/MeOH=20:1) to give the title compound (450 mg, 38%). LC/MS: 250.2 [M+H]$^+$.

Step 3: Preparation of 2-(2,6-dioxopiperidin-3-yl)-5-(4-(2-(1-(5-nitropyridin-2-yl)piperidin-4-yl)ethyl)piperazin-1-yl)isoindoline-1,3-dione To a solution of Intermediate 2-1 (152 mg, 0.4 mmol) in DCM (10 mL) and MeOH (3 mL) stirred under argon at room temperature was added sodium acetate trihydrate (49 mg, 0.6 mmol). The reaction mixture was stirred at room temperature for 30 minutes. To the reaction mixture was added 2-(1-(5-nitropyridin-2-yl)piperidin-4-yl) acetaldehyde (100 mg, 0.4 mmol) and acetic acid (48 mg, 0.8 mmol). The reaction mixture was stirred at room temperature for 30 minutes. To the reaction mixture was added NaCNBH$_3$ (38 mg, 0.6 mmol). The reaction mixture was stirred at room temperature for 1 hour. The residue was quenched with water (10 mL) and extracted with DCM (10 mL×3). The combined organic layers were dried over anhydrous sodium sulfate, filtered and concentrated in vacuum. The crude product was purified via preparative TLC (DCM/MeOH=10:1) to give the title compound (220 mg, 95%). LC/MS: 576.25 [M+H]⁺.

Step 4: Preparation of 5-(4-(2-(1-(5-aminopyridin-2-yl)piperidin-4-yl)ethyl)piperazin-1-yl)-2-(2,6-dioxopiperidin-3-yl)isoindoline-1,3-dione A mixture of 2-(2,6-dioxopiperidin-3-yl)-5-(4-(2-(1-(5-nitropyridin-2-yl)piperidin-4-yl)ethyl)piperazin-1-yl)isoindoline-1,3-dione (100 mg, 0.17 mmol), Pd/C (50 mg, 2.2 mmol) and THF (10 mL) was stirred under hydrogen at room temperature for 2 hours. The crude product was purified via preparative TLC (DCM/MeOH=10:1) to give the title compound (50 mg, 54%). LC/MS: 546.25 [M+H]⁺.

Step 5: Preparation of (2R,5S)-4-(3-chloro-4-cyanophenyl)-N-(6-(4-(2-(4-(2-(2,6-dioxopiperidin-3-yl)-1,3-dioxoisoindolin-5-yl)piperazin-1-yl)ethyl)piperidin-1-yl)pyridin-3-yl)-2,5-dimethylpiperazine-1-carboxamide (1-19)

A mixture containing 5-(4-(2-(1-(5-aminopyridin-2-yl)piperidin-4-yl)ethyl)piperazin-1-yl)-2-(2,6-dioxopiperidin-3-yl)isoindoline-1,3-dione (50 mg, 0.09 mmol), TEA (22 mg, 0.22 mmol), DMAP (15 mg, 0.12 mmol), phenyl chloroformate (19 mg, 0.12 mmol) and acetonitrile (10 mL) was stirred under hydrogen at room temperature for 2 hours. The residue was quenched with water (10 mL) and concentrated under vacuum. To the reaction mixture was added Intermediate 1-1 (23 mg, 0.09 mmol), TEA (22 mg, 0.22 mmol) and acetonitrile (10 mL). The reaction mixture was stirred at 100° C. overnight. The crude product was first purified via preparative TLC (DCM/MeOH=10:1) and further purified by reverse phase preparative HPLC to give the title compound as a formic acid salt (10 mg, 10%). LC/MS: 820.4 [M+H]⁺; ¹H NMR (400 MHz, DMSO) δ 11.68 (s, 1H), 11.11 (s, 1H), 8.78-8.52 (m, 1H), 8.20 (s, 1H), 7.83-7.59 (m, 3H), 7.48 (s, 1H), 7.36 (d, J=8.1 Hz, 1H), 7.17 (s, 1H), 7.01 (d, J=8.6 Hz, 1H), 6.91-6.68 (m, 1H), 5.10 (dd, J=12.9, 5.1 Hz, 1H), 4.57-4.48 (m, 1H), 4.30-4.15 (m, 4H), 4.00-3.88 (m, 1H), 3.68-3.60 (m, 1H), 3.58-3.47 (m, 4H), 3.35-3.27 (m, 2H), 3.23-3.14 (m, 2H), 3.06-2.84 (m, 2H), 2.83-2.67 (m, 2H), 2.65-2.55 (m, 2H), 2.20-1.97 (m, 3H), 1.80-1.67 (m, 3H), 1.65-1.43 (m, 2H), 1.35-1.05 (m, 8H).

Synthesis of (2R,5S)-4-(3-chloro-4-cyanophenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide (1-21)

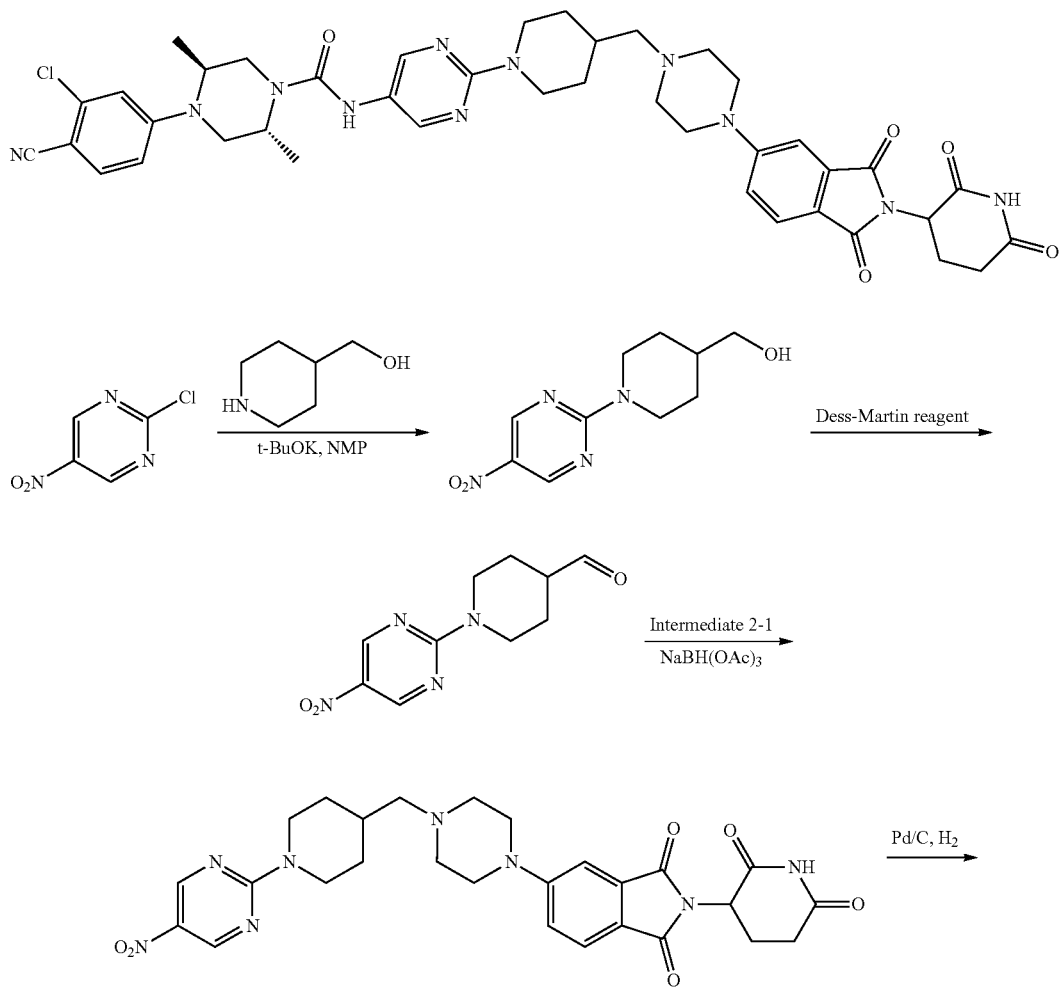

-continued

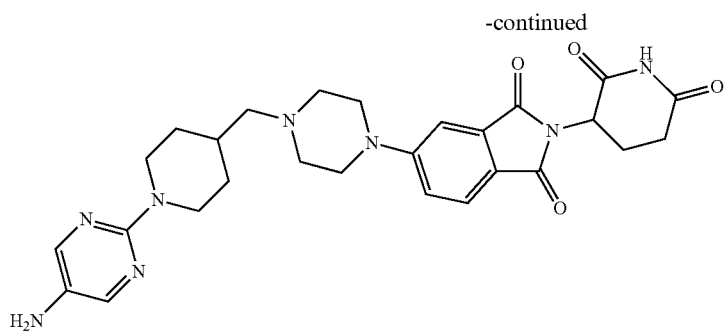

(1) phenyl chloroformate, TEA, ACN
(2) Intermediate 1-1, TEA
ACN, 90° C.

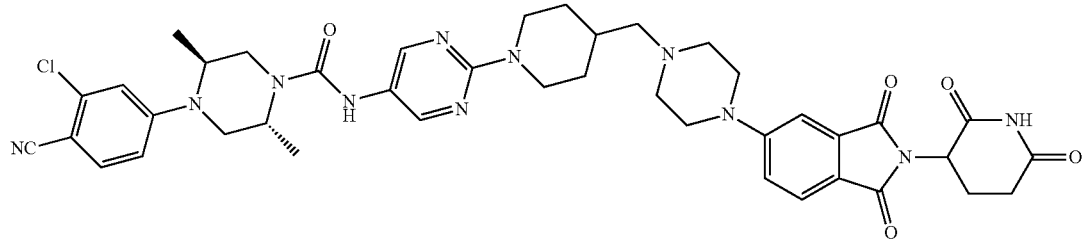

1-21

Step 1: Preparation of (1-(5-nitropyrimidin-2-yl)piperidin-4-yl)methanol

To a solution of 2-chloro-5-nitropyrimidine (3 g, 18.8 mmol) in NMP (80 mL) stirred in the air at room temperature was added piperidin-4-ylmethanol (2.16 g, 18.8 mmol), t-BuOK (6.3 g, 56.4 mmol). The reaction mixture was stirred at 90° C. for 16 hours. The mixture was treated with water (80 mL) and extracted by DCM (150 mL×3). The organic layers were combined and washed by brine, dried with MgSO$_4$. The solvent was removed under vacuum to give a crude product which was purified by silica gel column chromatography and eluted with 0-10% MeOH in DCM to give the title compound (1.8 g, 40%). LC/MS: 239.1 [M+H]$^+$; $^1$H NMR (400 MHz, CDCl$_3$) δ 9.07 (s, 2H), 5.09-4.93 (m, 2H), 3.58 (d, J=6.0 Hz, 2H), 3.05 (td, J=13.1, 2.4 Hz, 2H), 2.00-1.87 (m, 3H), 1.49 (s, 1H), 1.35-1.23 (m, 2H).

Step 2: Preparation of 1-(5-nitropyrimidin-2-yl)piperidine-4-carbaldehyde

To a solution of (1-(5-nitropyrimidin-2-yl)piperidin-4-yl)methanol (1 g, 4.2 mmol) in DCM (20 mL) stirred at room temperature was added Dess-Martin reagent (2.6 g, 6.3 mmol). The reaction mixture was stirred at room temperature for 1 hour. The solvent was removed under vacuum. The crude product was purified by silica gel column chromatography and eluted with 0-20% EA in PE to give the title compound (800 mg, 80%). LC/MS: 237.1 [M+H]$^+$; $^1$H NMR (400 MHz, CDCl$_3$) δ 9.75 (s, 1H), 9.08 (s, 2H), 4.68 (dt, J=13.6, 4.3 Hz, 2H), 3.45 (ddd, J=13.6, 10.5, 3.2 Hz, 2H), 2.65 (td, J=9.8, 4.8 Hz, 1H), 2.19-1.98 (m, 2H), 1.85-1.64 (m, 2H).

Step 3: Preparation of 2-(2,6-dioxopiperidin-3-yl)-5-(4-((1-(5-nitropyrimidin-2-yl)piperidin-4-yl)methyl)piperazin-1-yl)isoindoline-1,3-dione To a solution of 1-(5-nitropyrimidin-2-yl)piperidine-4-carbaldehyde (450 mg, 1.9 mmol) and Intermediate 2-1 (722 mg, 1.9 mmol) in DCM (10 mL) stirred under nitrogen at room temperature was added magnesium sulphate (4.56 g, 38 mmol) and triethylamine (384 mg, 3.8 mmol). The reaction mixture was stirred at room temperature for 1 hour. Then NaBH(OAc)$_3$ (1 g, 4.74 mmol) was added in portions. The reaction was stirred for 1 hour. The solvent was removed in vacuum to give a crude product. The crude product was purified by silica gel column chromatography eluted with 0-15% MeOH in DCM to give the title compound (900 mg, 84%). LC/MS: 563.2 [M+H]$^+$; $^1$H NMR (400 MHz, CDCl$_3$) δ 9.07 (s, 2H), 8.14 (s, 1H), 7.72 (d, J=8.5 Hz, 1H), 7.31 (d, J=2.2 Hz, 1H), 7.08 (dd, J=8.6, 2.2 Hz, 1H), 5.32 (s, 2H), 5.01-4.92 (m, 3H), 3.45 (s, 3H), 3.10-3.01 (m, 2H), 2.95-2.75 (m, 3H), 2.61 (s, 3H), 2.30 (d, J=6.8 Hz, 2H), 2.19-2.11 (m, 1H), 2.02-1.88 (m, 3H), 1.28-1.16 (m, 2H).

Step 4: Preparation of 5-(4-((1-(5-aminopyrimidin-2-yl)piperidin-4-yl)methyl)piperazin-1-yl)-2-(2,6-dioxopiperidin-3-yl)isoindoline-1,3-dione To a solution of 2-(2,6-dioxopiperidin-3-yl)-5-(4-((1-(5-nitropyrimidin-2-yl)piperidin-4-yl)methyl)piperazin-1-yl)isoindoline-1,3-dione (900 mg, 1.6 mmol) in THF (100 mL) was added Pd/C (169 mg, 0.16 mmol) and the mixture was stirred under H$_2$ at room temperature for 4 hours. The mixture was filtered, and the solvent was removed in vacuum to give the title compound (800 mg, 94%). LC/MS: 533.2 [M+H]$^+$.

Step 5: Preparation of (2R,5S)-4-(3-chloro-4-cyanophenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide (1-21)

To a solution containing 5-(4-((1-(5-aminopyrimidin-2-yl)piperidin-4-yl)methyl)piperazin-1-yl)-2-(2,6-dioxopiperidin-3-yl)isoindoline-1,3-dione (100 mg, 0.19 mmol), phenyl chloroformate (31.2 mg, 0.2 mmol), and TEA (20 mg, 0.2 mmol) in ACN (2 mL) was added DMAP (2.4 mg, 0.02 mmol). The reaction mixture was stirred at room temperature for 2 hours. The reaction mixture was quenched by adding H₂O (2 mL). Solvent was removed under vacuum and the residue was dissolved in ACN (10 mL). Then 2-chloro-4-((2S,5R)-2,5-dimethylpiperazin-1-yl)benzonitrile (48 mg, 0.19 mmol) was added. The reaction mixture was stirred at 90° C. overnight. Solvent was concentrated in vacuum to give a crude product. The crude product was purified by preparative TLC eluted with MeOH:DCM=1:10 to give the title compound (70 mg, 45%). LC/MS: 808.2 [M+H]⁺; ¹H NMR (400 MHz, DMSO) δ 11.10 (s, 1H), 8.42 (s, 1H), 8.36 (s, 2H), 7.68 (t, J=8.5 Hz, 2H), 7.35 (s, 1H), 7.27 (d, J=8.6 Hz, 1H), 7.18 (d, J=2.0 Hz, 1H), 7.01 (dd, J=9.1, 2.1 Hz, 1H), 5.08 (dd, J=12.9, 5.3 Hz, 1H), 4.59 (d, J=13.0 Hz, 2H), 4.49-4.23 (m, 2H), 3.83 (d, J=13.5 Hz, 1H), 3.67 (d, J=12.7 Hz, 1H), 3.45 (s, 4H), 3.40-3.35 (m, 1H), 3.33-3.28 (m, 2H), 2.93-2.81 (m, 3H), 2.68-2.52 (m, 5H), 2.20 (d, J=6.2 Hz, 2H), 2.07-1.97 (m, 1H), 1.87-1.73 (m, 3H), 1.27-1.00 (m, 8H).

Synthesis of (2S,5R)-4-(3-chloro-4-cyanophenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide (1-22)

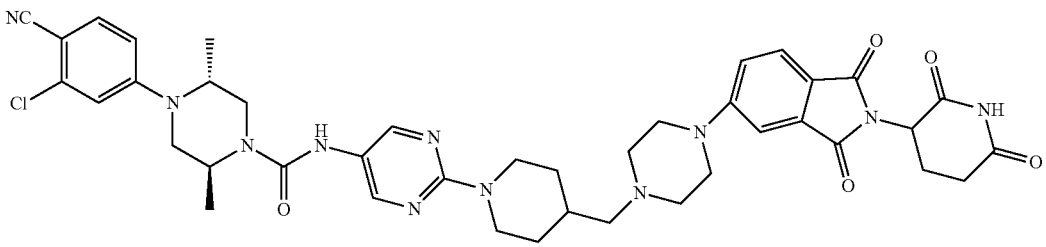 [SMILES: C[C@@H]1CN(C(=O)Nc2cnc(N3CCC(CN4CCN(c5ccc6c(c5)C(=O)N(C5CCC(=O)NC5=O)C6=O)CC4)CC3)nc2)[C@@H](C)CN1c1ccc(C#N)c(Cl)c1]

This compound was prepared using the same method as described for the preparation of 1-21. LC/MS: 808.2 [M+H]⁺; ¹H NMR (400 MHz, DMSO) δ 11.10 (s, 1H), 8.43 (s, 1H) 8.36 (s, 2H), 7.68 (t, J=8.7 Hz, 2H), 7.35 (s, 1H), 7.27 (d, J=8.6 Hz, 1H), 7.18 (d, J=2.1 Hz, 1H), 7.01 (dd, J=9.2, 2.1 Hz, 1H), 5.08 (dd, J=12.8, 5.3 Hz, 1H), 4.59 (d, J=12.9 Hz, 2H), 4.49-4.23 (m, 2H), 3.83 (d, J=13.2 Hz, 1H), 3.67 (d, J=12.6 Hz, 1H), 3.52-3.36 (m, 5H), 3.32-3.26 (m, 3H), 2.86 (t, J=12.9 Hz, 3H), 2.65-2.54 (m, 4H), 2.20 (s, 2H), 2.03-1.98 (m, 1H), 1.86-1.73 (m, 3H), 1.27-1.05 (m, 8H).

Synthesis of (2R,5S)-4-(4-cyano-3-methoxyphenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide (1-26)

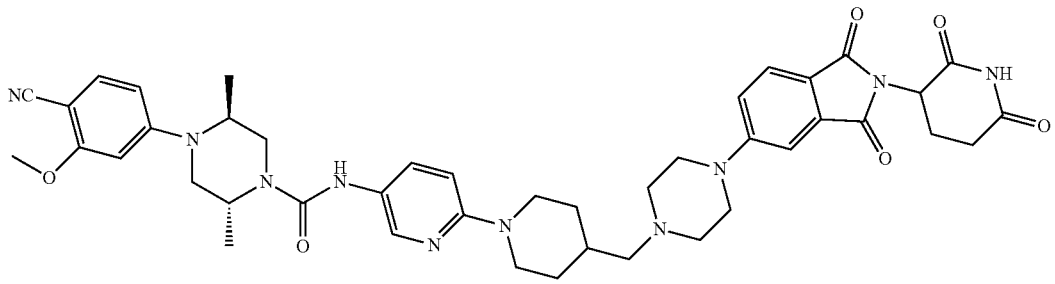 [SMILES: COc1cc(N2C[C@@H](C)N(C(=O)Nc3ccc(N4CCC(CN5CCN(c6ccc7c(c6)C(=O)N(C6CCC(=O)NC6=O)C7=O)CC5)CC4)nc3)C[C@@H]2C)ccc1C#N]

This compound was prepared using the same method as described for the preparation of 1-14 except that Intermediate 1-3 was used in the final step of urea formation. LC/MS: 803.3 [M+H]⁺; ¹H NMR (400 MHz, DMSO) δ 11.10 (s, 1H), 8.41 (s, 1H), 8.14 (s, 1H), 7.55-7.65 (m, 1H), 7.61-7.55 (m, 1H), 7.43 (d, J=8.8 Hz, 1H), 7.35 (s, 1H), 7.30-7.23 (m, 1H), 6.83-6.74 (m, 1H), 6.63-6.57 (m, 1H), 6.55-6.50 (m, 1H), 5.15-5.05 (m, 1H), 4.50-4.43 (m, 1H), 4.35-4.23 (m, 1H), 4.22-4.15 (m, 2H), 3.90 (s, 3H), 3.86 (m, 1H), 3.65-3.53 (m, 2H), 3.50-3.42 (m, 3H), 3.39-3.35 (m, 1H), 3.16-3.05 (m, 1H), 3.00-2.80 (m, 2H), 2.90-2.53 (m, 7H), 2.30-2.10 (m, 2H), 2.08-1.98 (m, 1H), 1.90-1.75 (m, 3H), 1.23 (br s, 2H), 1.17 (d, J=6.6 Hz, 3H), 1.08 (d, J=6.5 Hz, 3H).

Synthesis of (2R,5S)-4-(4-cyano-3-methoxyphenyl)-N-(4-(4-((4-(2-(2,6-dioxopiperidin-3-yl)-1,3-dioxoisoindolin-5-yl)piperazin-1-yl)methyl)piperidin-1-yl)-2,5-difluorophenyl)-2,5-dimethylpiperazine-1-carboxamide (1-29)

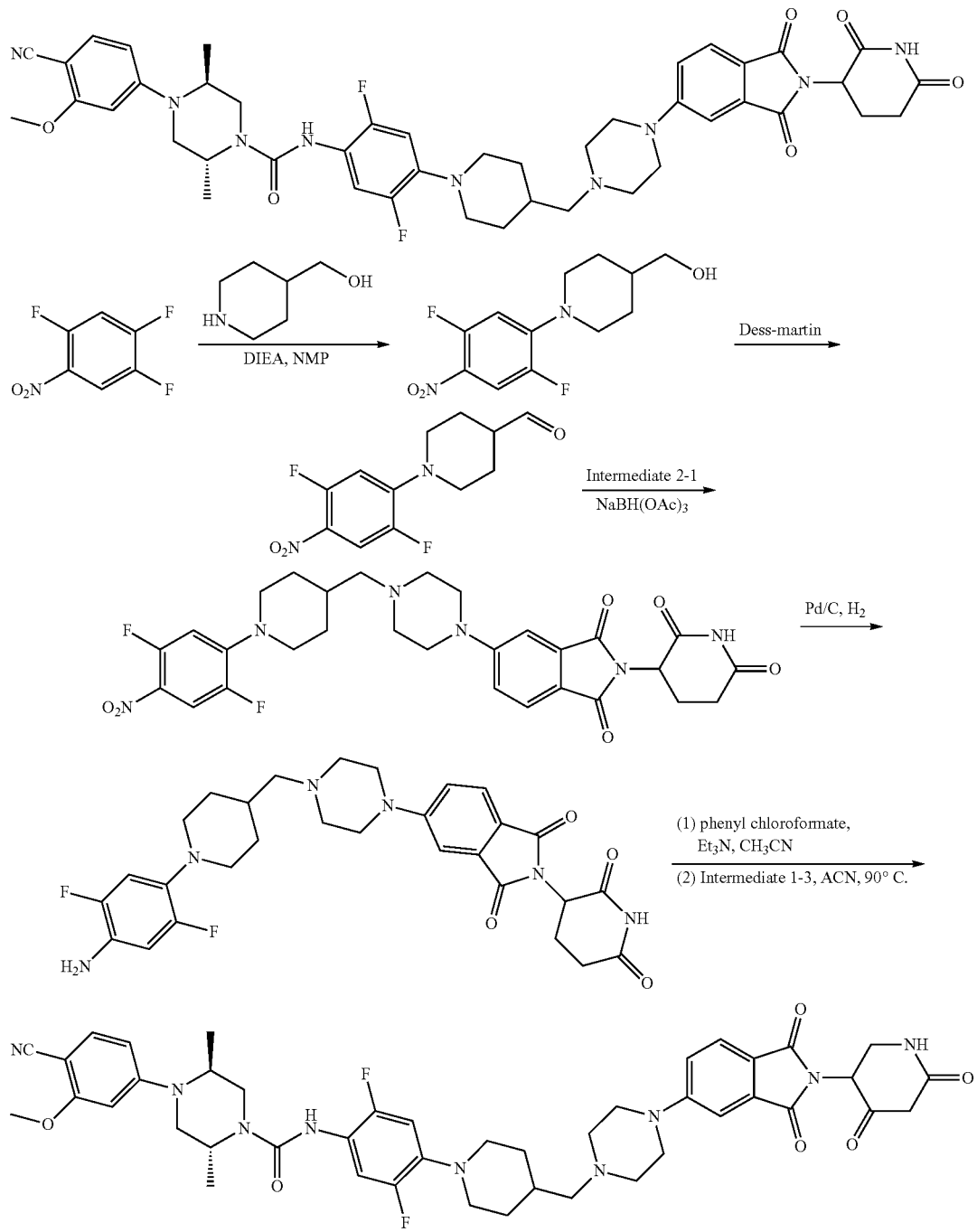

1-29

This compound was prepared using the same method as described for the preparation of 1-14. LC/MS: 838.2 [M+H]+; 1H NMR (400 MHz, DMSO) δ 11.10 (s, 1H), 8.31 (s, 1H), 7.69 (d, J=8.5 Hz, 1H), 7.44 (d, J=8.8 Hz, 1H), 7.36 (s, 1H), 7.27 (d, J=8.5 Hz, 1H), 7.20 (dd, J=13.6, 7.5 Hz, 1H), 6.89 (dd, J=12.1, 8.2 Hz, 1H), 6.59 (d, J=8.8 Hz, 1H), 6.53 (s, 1H), 5.09 (dd, J=12.9, 5.3 Hz, 1H), 4.43 (br, 1H), 4.27 (br, 1H), 3.90 (s, 3H), 3.82 (d, J=13.1 Hz, 1H), 3.60 (d, J=12.0 Hz, 1H), 3.46 (s, 4H), 3.37 (d, J=13.7 Hz, 2H), 3.30 (m, 3H), 2.88 (d, J=11.9 Hz, 1H), 2.71-2.52 (m, 7H), 2.25 (d, J=5.2 Hz, 2H), 2.07-1.97 (m, 1H), 1.83 (d, J=11.2 Hz, 2H), 1.69 (br s, 1H), 1.36-1.23 (m, 2H), 1.19 (d, J=6.6 Hz, 3H), 1.09 (d, J=6.4 Hz, 3H).

Synthesis of (2R,5S)-4-(4-cyano-3-(trifluoromethyl) phenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide (1-30)

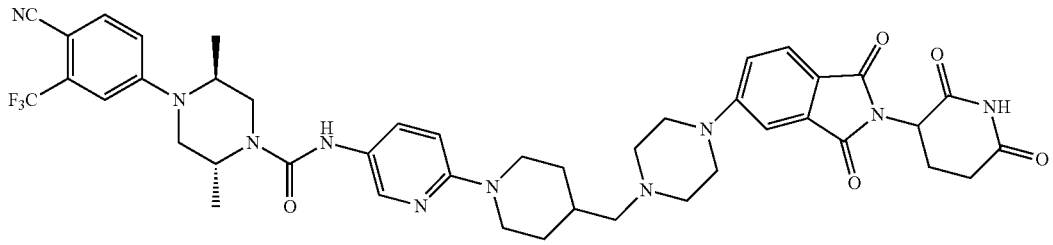 [SMILES: C[C@@H]1CN(c2ccc(C#N)c(C(F)(F)F)c2)[C@@H](C)CN1C(=O)Nc1ccc(N2CCC(CN3CCN(c4ccc5c(c4)C(=O)N(C4CCC(=O)NC4=O)C5=O)CC3)CC2)nc1]

This compound was prepared using the same method as described for the synthesis of 1-14. LC/MS: 841.3 [M+H]+; 1H NMR (400 MHz, DMSO) δ 11.10 (s, 1H), 8.46-8.39 (m, 1H), 8.14 (s, 1H), 7.85 (d, J=8.8 Hz, 1H), 7.69 (d, J=8.2 Hz, 1H), 7.63-7.57 (m, 2H), 7.36 (s, 1H), 7.31-7.26 (m, 2H), 6.82-6.76 (m, 1H), 5.12-5.06 (m, 1H), 4.52-4.30 (m, 3H), 4.19 (d, J=11.4 Hz, 3H), 3.87 (d, J=14.0 Hz, 1H), 3.73 (d, J=11.7 Hz, 1H), 3.46 (s, 2H), 3.42-3.36 (m, 2H), 3.20-3.02 (m, 3H), 2.96-2.83 (m, 2H), 2.77-2.73 (m, 1H), 2.70-2.54 (m, 2H), 2.36-2.32 (m, 1H), 2.21 (s, 2H), 2.08-1.98 (m, 2H), 1.83-1.76 (m, 2H), 1.25-1.10 (m, 8H).

Synthesis of (2R,5S)-4-(4-cyano-3-(trifluoromethyl) phenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide (1-31)

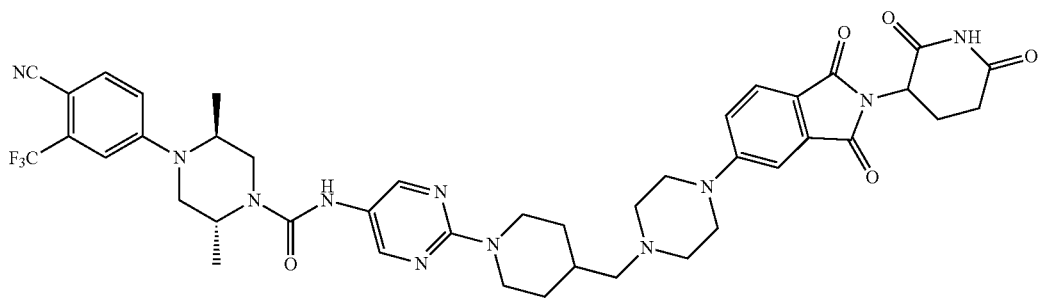 [SMILES: C[C@@H]1CN(c2ccc(C#N)c(C(F)(F)F)c2)[C@@H](C)CN1C(=O)Nc1cnc(N2CCC(CN3CCN(c4ccc5c(c4)C(=O)N(C4CCC(=O)NC4=O)C5=O)CC3)CC2)nc1]

This compound was prepared using the same method as described for the preparation of 1-14 except that Intermediate 1-4 was used in the final step of urea formation. LC/MS: 842.3 [M+H]+; 1H NMR (400 MHz, DMSO) δ 11.10 (s, 1H), 8.52 (s, 1H), 8.38 (s, 2H), 7.85 (d, J=8.7 Hz, 1H), 7.75-7.65 (m, 1H), 7.40-7.21 (m, 4H), 5.14-5.06 (m, 1H), 4.65-4.54 (m, 2H), 4.53-4.30 (m, 3H), 3.91-3.83 (m, 1H), 3.77-3.71 (m, 1H), 3.54-3.43 (m, 6H), 3.22-3.03 (m, 2H), 2.92-2.80 (m, 3H), 2.72-2.57 (m, 3H), 2.25-2.15 (m, 2H), 2.07-2.00 (m, 1H), 1.90-1.77 (m, 3H), 1.28-1.15 (m, 8H).

Synthesis of (2R,5S)-4-(4-cyano-3-(trifluoromethyl)phenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide (1-43)

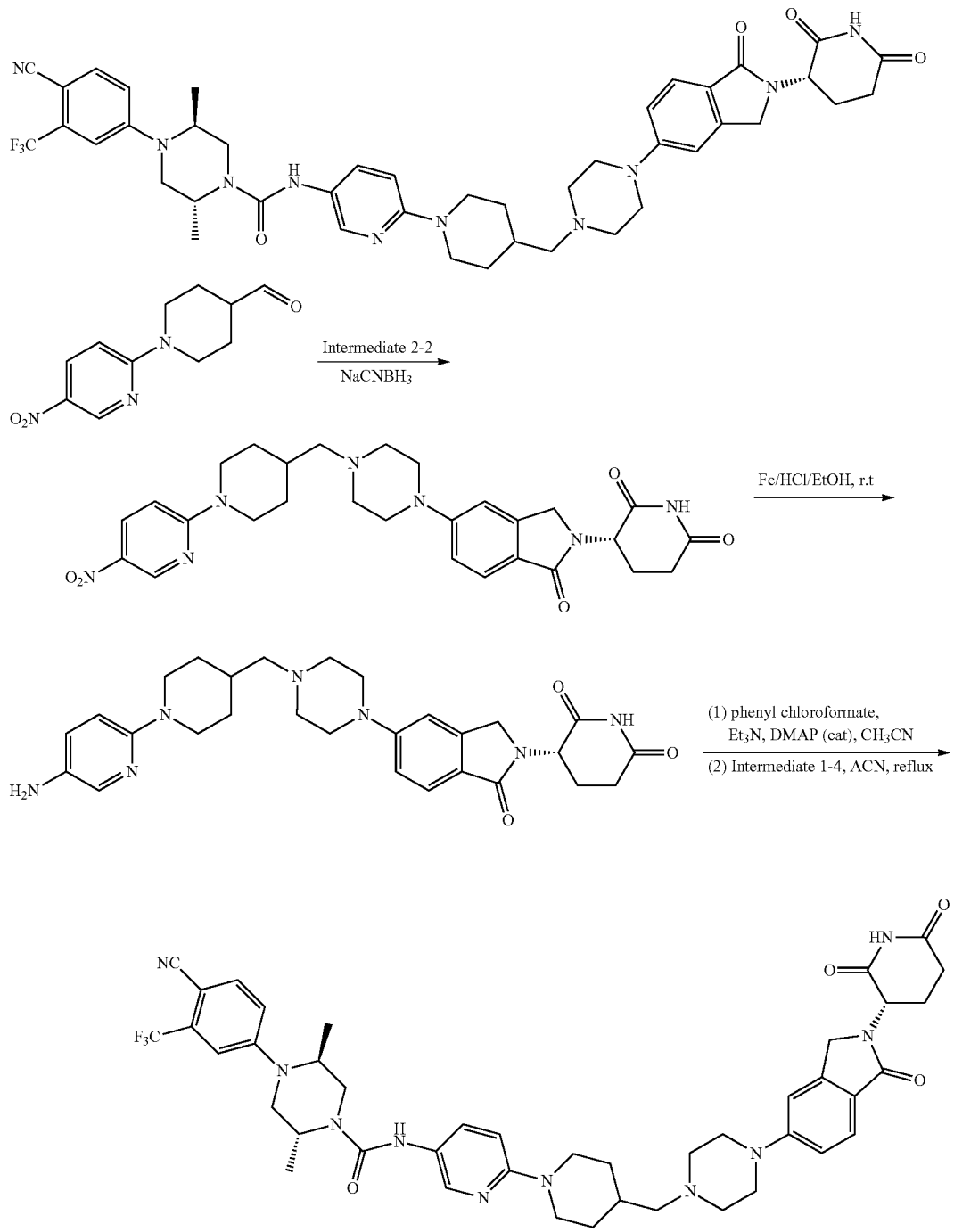

1-43

Step 1: Preparation of (S)-3-(5-(4-((1-(5-nitropyridin-2-yl)piperidin-4-yl)methyl)piperazin-1-yl)-1-oxoisoindolin-2-yl)piperidine-2,6-dione To a solution of Intermediate 2-2 (617 mg, 1.27 mmol) in DCM/MeOH (15 mL, 10:3) stirred at 15° C. was added AcONa (156 mg, 1.9 mmol). After 30 minutes, AcOH (152 mg, 2.54 mmol) was added, then 1-(5-nitropyridin-2-yl)piperidine-4-carbaldehyde (300 mg, 1.27 mmol) was added. The mixture was stirred at 15° C. for 30 minutes before NaCNBH₃ (119.7 mg, 1.9 mmol) was added. The reaction mixture was stirred at 15° C. for 1 hour. LC/MS showed the reaction completed. The mixture was quenched with the addition of 30 mL of water, extracted with DCM (30 mL×2), and the combined organic layer was washed with brine, dried and concentrated under vacuum to give a crude product, which was purified by silica gel column chromatography (DCM/MeOH=10:1) to afford the desired compound (150 mg, 21.5%) as a yellow solid. LC/MS: 548.6 [M+H].

Step 2: Preparation of (S)-3-(5-(4-((1-(5-aminopyridin-2-yl)piperidin-4-yl)methyl)piperazin-1-yl)-1-oxoisoindolin-2-yl)piperidine-2,6-dione To a stirred mixture of (S)-3-(5-(4-((1-(5-nitropyridin-2-yl)piperidin-4-yl)methyl)piperazin-1-yl)-1-oxoisoindolin-2-yl)piperidine-2,6-dione (260 mg, 0.47 mmol) in EtOH (10 mL) and H₂O (10 mL) was added Fe (183 mg, 3.32 mmol) and NH₄Cl (125 mg, 2.35 mmol), and the mixture was stirred at 70° C. for 2 hours. After the reaction completed, the solid was filtered, and the filtrate was concentrated under vacuum to give a crude product, which was purified by flash column chromatography (DCM/MeOH=10:1) to afford the desired compound (50 mg, 20.3%) as a brown solid. LC/MS: 518.4 [M+H]⁺.

Step 3: Preparation of (2R,5S)-4-(4-cyano-3-(trifluoromethyl)phenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide (1-43)

To a solution containing (S)-3-(5-(4-((1-(5-aminopyridin-2-yl)piperidin-4-yl)methyl)piperazin-1-yl)-1-oxoisoindolin-2-yl)piperidine-2,6-dione (40 mg, 0.08 mmol), phenyl chloroformate (14.9 mg, 0.09 mmol), and TEA (8.9 mg, 0.09 mmol) in ACN (10 mL) was added DMAP (1.3 mg, 0.01 mmol). The reaction mixture was stirred at room temperature for 2 hours. The reaction mixture was quenched by adding H₂O (2 mL). Solvents were removed under reduced pressure and the residue was dissolved in ACN (10 mL). Then 4-((2S,5R)-2,5-dimethylpiperazin-1-yl)-2-(trifluoromethyl)benzonitrile (Intermediate 1-4, 25.52 mg, 0.08 mmol) was added. The reaction mixture was stirred at 90° C. overnight. The mixture was concentrated in vacuum and the crude residue was purified by preparative TLC (MeOH/DCM=1:10) to give the title compound (9.2 mg, 13.6%). LC/MS: 827.6 [M+H]⁺; HRMS: 827.4022; ¹H NMR (400 MHz, DMSO) δ 10.98 (s, 1H), 8.52 (br s, 1H), 8.18 (s, 1H), 7.87 (d, J=8.8 Hz, 1H), 7.74 (br, 1H), 7.62 (d, J=8.5 Hz, 1H), 7.34-7.25 (m, 2H), 7.23-7.14 (m, 2H), 7.00 (br, 1H), 5.08 (dd, J=13.4, 4.9 Hz, 1H), 4.46 (s, 1H), 4.37 (d, J=16.8 Hz, 2H), 4.28-4.17 (m, 3H), 4.06-3.99 (m, 1H), 3.86 (d, J=13.4 Hz, 1H), 3.75 (d, J=13.6 Hz, 2H), 3.40-3.38 (m, 1H), 3.37-3.34 (m, 1H), 3.24-3.11 (m, 4H), 2.94-2.86 (m, 2H), 2.69-2.62 (m, 2H), 2.57 (d, J=14.5 Hz, 1H), 2.43-2.38 (m, 1H), 2.37-2.32 (m, 1H), 2.13 (br, 2H), 2.00-1.95 (m, 1H), 1.85 (br d, J=11.0 Hz, 3H), 1.33-1.04 (m, 8H).

Synthesis of (2R,5S)-4-(4-cyano-3-methoxyphenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide (1-33)

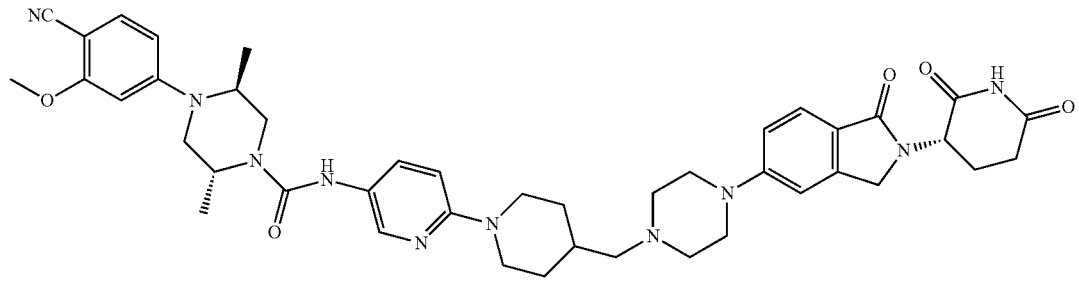 [SMILES: COc1cc(N2C[C@@H](C)N(C(=O)Nc3ccc(N4CCC(CN5CCN(c6ccc7c(c6)CN([C@H]6CCC(=O)NC6=O)C7=O)CC5)CC4)nc3)C[C@@H]2C)ccc1C#N]

This compound was prepared using the same method as described for the synthesis of 1-43. LC/MS: 789.5 [M+H]⁺; ¹H NMR (400 MHz, DMSO) δ 10.97 (s, 1H), 8.37 (s, 1H), 8.15-8.10 (m, 1H), 7.59 (d, J=9.1 Hz, 1H), 7.53 (d, J=8.5 Hz, 1H), 7.44 (d, J=8.8 Hz, 1H), 7.12-7.04 (m, 2H), 6.78 (d, J=9.1 Hz, 1H), 6.61 (d, J=8.6 Hz, 1H), 6.54 (s, 1H), 5.06 (dd, J=13.3, 5.0 Hz, 1H), 4.45 (brs, 1H), 4.37-4.16 (m, 5H), 3.92-3.80 (s and d, 4H), 3.61 (d, J=12.8 Hz, 1H), 3.33-3.22 (m, 8H), 2.93-2.86 (m, 2H), 2.74 (t, J=11.8 Hz, 2H), 2.60 (d, J=16.6 Hz, 1H), 2.44-2.31 (m, 2H), 2.21 (d, J=6.4 Hz, 2H), 2.00-1.94 (m, 1H), 1.79 (d, J=10.7 Hz, 3H), 1.27-1.01 (m, 8H).

Synthesis of (2R,5S)-4-(3-chloro-4-cyanophenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide (1-44)

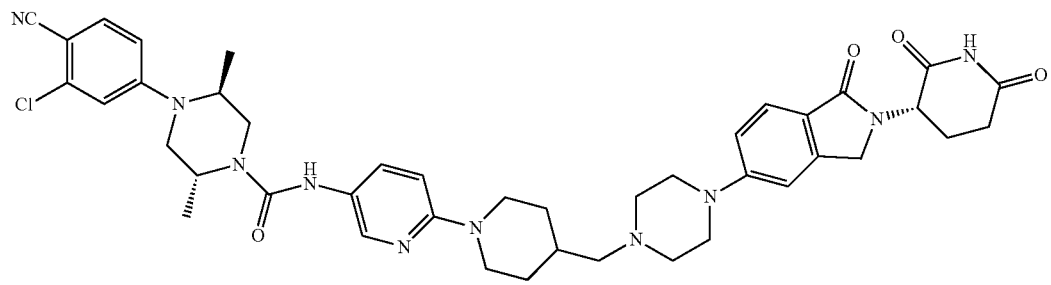 [SMILES: C[C@@H]1CN(c2ccc(C#N)c(Cl)c2)[C@@H](C)CN1C(=O)Nc1ccc(N2CCC(CN3CCN(c4ccc5c(c4)CN([C@H]4CCC(=O)NC4=O)C5=O)CC3)CC2)nc1]

This compound was prepared using the same method as described for the synthesis of 1-43. LC/MS: 792.5 [M+H]$^+$; $^1$H NMR (400 MHz, DMSO) δ 10.97 (s, 1H), 8.38 (s, 1H), 8.13 (d, J=2.6 Hz, 1H), 7.67 (d, J=8.9 Hz, 1H), 7.59 (dd, J=9.0, 2.6 Hz, 1H), 7.53 (d, J=8.6 Hz, 1H), 7.18 (d, J=1.9 Hz, 1H), 7.14-7.04 (m, 2H), 7.04-6.96 (m, 1H), 6.77 (d, J=9.2 Hz, 1H), 5.06 (dd, J=13.4, 5.1 Hz, 1H), 4.45 (brs, 1H), 4.39-4.12 (m, 5H), 3.85 (d, J=14.0 Hz, 1H), 3.66 (d, J=12.7 Hz, 1H), 3.34-3.22 (m, 8H), 2.96-2.85 (m, 2H), 2.73 (t, J=11.7 Hz, 2H), 2.67-2.54 (m, 1H), 2.43-2.30 (m, 2H), 2.21 (d, J=6.5 Hz, 2H), 2.01-1.94 (m, 1H), 1.79 (d, J=10.3 Hz, 3H), 1.29-1.10 (m, 8H).

Synthesis of (2R,5S)-4-(4-cyano-3-methoxyphenyl)-N-(4-(4-((4-(2-(2,6-dioxopiperidin-3-yl)-1,3-dioxoisoindolin-5-yl)piperazin-1-yl)methyl)piperidin-1-yl)-3-fluorophenyl)-2,5-dimethylpiperazine-1-carboxamide (1-48)

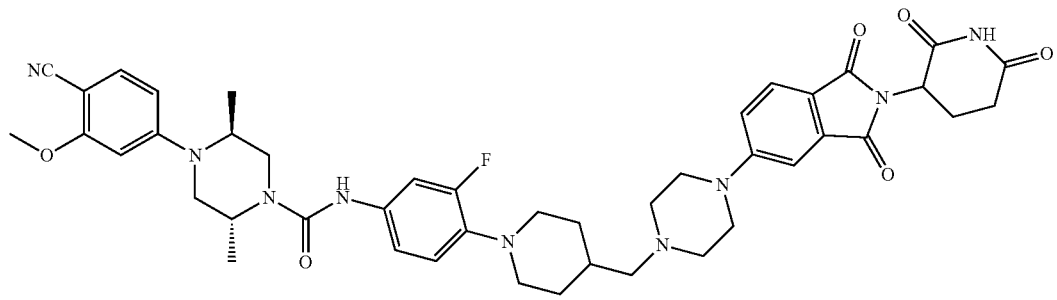 [SMILES: COc1cc(N2C[C@@H](C)N(C(=O)Nc3ccc(N4CCC(CN5CCN(c6ccc7c(c6)C(=O)N(C6CCC(=O)NC6=O)C7=O)CC5)CC4)c(F)c3)C[C@@H]2C)ccc1C#N]

This compound was prepared using the same method as described in the synthesis of 1-14. LC/MS: 819.5 [M+H]+; 1H NMR (400 MHz, DMSO) δ 11.09 (s, 1H), 8.57 (s, 1H), 7.68 (d, J=8.5 Hz, 1H), 7.49-7.32 (m, 3H), 7.31-7.22 (d, J=7.9 Hz, 1H), 7.16 (d, J=7.9 Hz, 1H), 6.94 (t, J=9.4 Hz, 1H), 6.59 (d, J=8.0 Hz, 1H), 6.53 (s, 1H), 5.07 (dd, J=12.8, 5.2 Hz, 1H), 4.46 (br m, 1H), 4.28 (br, 1H), 3.89 (s, 3H), 3.85 (d, J=12.5 Hz, 1H), 3.59 (d, J=12.5 Hz, 1H), 3.49-3.37 (m, 6H), 3.31-3.20 (m, 4H), 2.93-2.83 (m, 1H), 2.67-2.54 (m, 6H), 2.28-2.18 (m, 2H), 2.07-1.95 (m, 1H), 1.86-1.75 (m, 2H), 1.70-1.61 (m, 1H), 1.41-1.21 (m, 2H), 1.17 (d, J=6.5 Hz, 3H), 1.06 (d, J=6.4 Hz, 3H).

Synthesis of (2R,5S)-4-(4-cyano-3-(trifluoromethyl)phenyl)-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide (1-49)

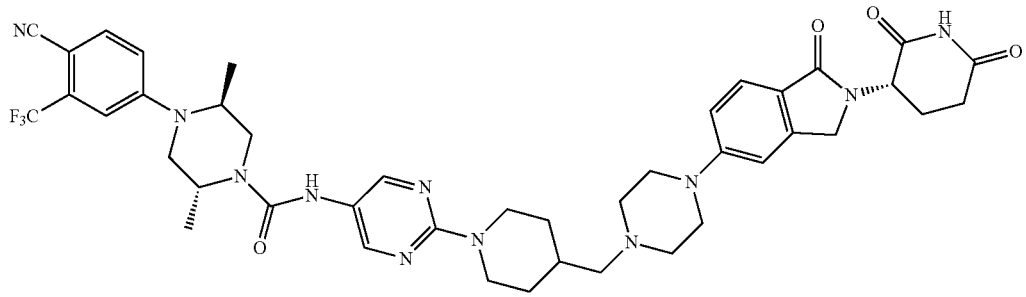 [SMILES: C[C@@H]1CN(c2ccc(C#N)c(C(F)(F)F)c2)[C@@H](C)CN1C(=O)Nc1cnc(N2CCC(CN3CCN(c4ccc5c(c4)CN([C@H]4CCC(=O)NC4=O)C5=O)CC3)CC2)nc1]

This compound was prepared using the same method as described in the synthesis of 1-43. LC/MS: 827.5 [M+H]+; 1H NMR (400 MHz, DMSO) δ 10.96 (s, 1H), 8.47 (brs, 1H), 8.37 (d, J=3.2 Hz, 2H), 7.85 (d, J=8.9 Hz, 1H), 7.54 (d, J=8.3 Hz, 1H), 7.32-7.26 (m, 2H), 7.09 (s, 2H), 5.06 (dd, J=13.3, 5.0 Hz, 1H), 4.59 (d, J=12.8 Hz, 2H), 4.46 (brs, 1H), 4.35 (d, J=17.1 Hz, 2H), 4.26-4.19 (m, 1H), 3.96-3.81 (m, 1H), 3.74 (d, J=12.1 Hz, 1H), 3.44-3.36 (m, 2H), 3.32-3.27 (m, 6H), 2.97-2.80 (m, 3H), 2.59 (d, J=16.0 Hz, 1H), 2.46-2.30 (m, 3H), 2.21 (brs, 2H), 2.00-1.94 (m, 1H), 1.90-1.74 (m, 3H), 1.33-1.23 (m, 2H), 1.18 (d, J=6.6 Hz, 3H), 1.11 (d, J=6.5 Hz, 3H).

Synthesis of (2R,5S)-4-(3-chloro-4-cyanophenyl)-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide (1-51)

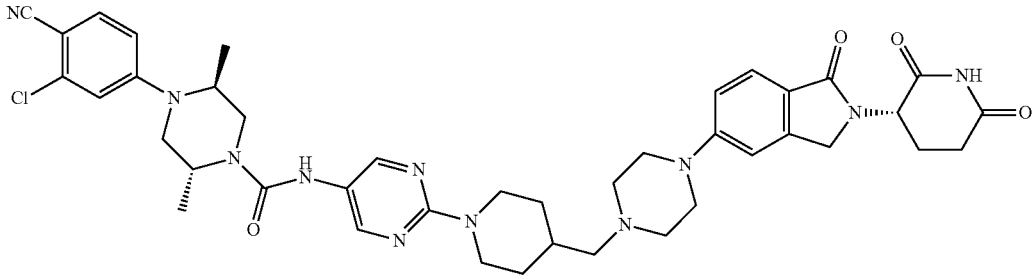 [SMILES: C[C@@H]1CN(c2ccc(C#N)c(Cl)c2)[C@@H](C)CN1C(=O)Nc1cnc(N2CCC(CN3CCN(c4ccc5c(c4)CN([C@H]4CCC(=O)NC4=O)C5=O)CC3)CC2)nc1]

This compound was prepared using the same method as described for the preparation of 1-43. LC/MS: 793.5 [M+H]+; 1H NMR (400 MHz, DMSO) δ=10.97 (s, 1H), 8.44 (s, 1H), 8.36 (s, 2H), 7.67 (d, J=8.8 Hz, 1H), 7.54 (d, J=7.6 Hz, 1H), 7.18 (d, J=2.0 Hz, 1H), 7.1 (s, 2H), 7.01 (dd, J=8.8, 2.0 Hz, 1H), 5.06 (dd, J=9.2, 4.8 Hz, 1H), 4.59 (d, J=11.2 Hz, 2H), 4.43 (br s, 1H), 4.37-4.19 (m, 3H), 3.83 (d, J=13.2 Hz, 1H), 3.67 (d, J=12.4 Hz, 1H), 3.35-3.25 (m, 7H), 3.13-3.06 (m, 1H), 2.96-2.83 (m, 3H), 2.65-2.53 (m, 2H), 2.44-2.31 (m, 2H), 2.23-2.17 (m, 2H), 2.03-1.93 (m, 1H), 1.8 (d, J=11.6 Hz, 2H), 1.48 (m, 1H), 1.35-1.24 (m, 2H), 1.17 (d, J=6.4 Hz, 3H), 1.09 (d, J=6.4 Hz, 3H).

Synthesis of (2R,5S)-4-(4-cyano-3-methoxyphenyl)-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide (1-52)

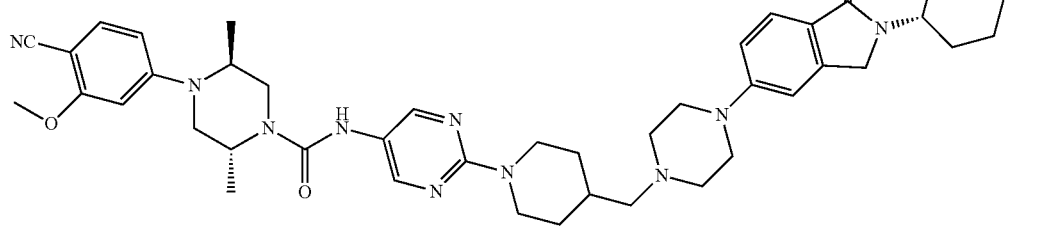

This compound was prepared using the same method as described for the synthesis of 1-43. LC/MS: 789.7 [M+H]+; 1H NMR (400 MHz, DMSO) δ=10.97 (s, 1H), 8.46 (s, 1H), 8.36 (s, 2H), 7.55 (d, J=7.6 Hz, 1H), 7.44 (d, J=8.4 Hz, 1H), 7.10 (s, 2H), 6.61 (d, J=8.4 Hz, 1H), 6.54 (s, 1H), 5.06 (d, J=13.2 Hz, 1H), 4.59 (d, J=12.4 Hz, 2H), 4.44 (s, 1H), 4.36-4.18 (m, 3H), 3.90 (s, 3H), 3.85 (d, J=13.6 Hz, 1H), 3.62 (d, J=12.4 Hz, 1H), 3.50-3.20 (m, 8H), 2.92-2.80 (m, 3H), 2.60 (m, 4H), 2.44-2.31 (m, 2H), 1.97 (m, 2H), 1.81 (d, J=11.2 Hz, 2H), 1.29-1.09 (m, 8H).

Synthesis of (2R,5S)-4-(4-cyano-3-methoxyphenyl)-N-(4-(4-((4-(2-((S)-2,6-dioxopiperidin-3-yl)-1-oxoisoindolin-5-yl)piperazin-1-yl)methyl)piperidin-1-yl)-3-fluorophenyl)-2,5-dimethylpiperazine-1-carboxamide (1-53)

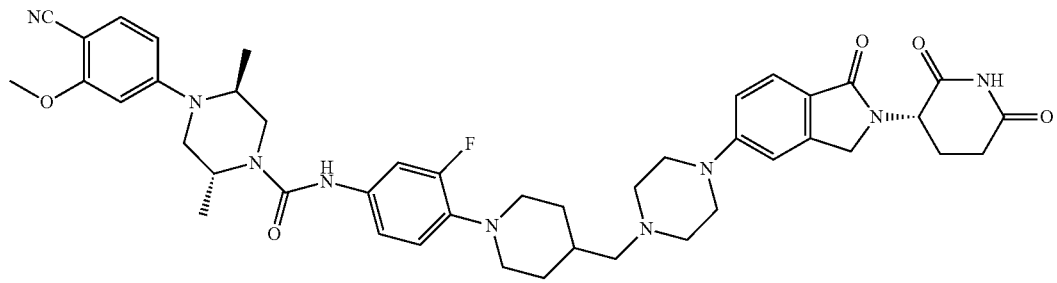 [SMILES: COc1cc(N2C[C@@H](C)N(C(=O)Nc3ccc(N4CCC(CN5CCN(c6ccc7c(c6)CN([C@H]6CCC(=O)NC6=O)C7=O)CC5)CC4)c(F)c3)C[C@@H]2C)ccc1C#N]

This compound was prepared using the same method as described for the synthesis of 1-43. LC/MS: 805.4[M+1]+; $^1$H NMR (400 MHz, DMSO) δ=10.96 (s, 1H), 8.56 (s, 1H), 7.53 (d, J=8.7, 1H), 7.43 (d, J=8.8, 1H), 7.38 (d, J=15.3, 1H), 7.16 (d, J=8.2, 1H), 7.12-7.06 (s, 2H), 6.98-6.90 (m, 1H), 6.59 (d, J=8.9, 1H), 6.52 (s, 1H), 5.08-5.03 (m, 1H), 4.49-4.43 (m, 1H), 4.37-4.31 (m, 2H), 4.24-4.18 (m, 1H), 3.94-3.81 (m, 4H), 3.60 (d, J=12.2, 1H), 3.50-3.00 (m, 10H)), 2.93-2.87 (m, 2H), 2.69-2.55 (m, 3H), 2.43-2.20 (m, 4H), 1.96-1.66 (m, 4H), 1.40-1.22 (m, 2H), 1.17 (d, J=6.6, 3H), 1.06 (d, J=6.5, 3H).
Synthesis of (2R,5S)-4-(8-cyanoquinolin-5-yl)-N-(4-(4-((4-(2-((S)-2,6-dioxopiperidin-3-yl)-1-oxoisoindolin-5-yl)piperazin-1-yl)methyl)piperidin-1-yl)-2,5-difluorophenyl)-2,5-dimethylpiperazine-1-carboxamide (2-18)
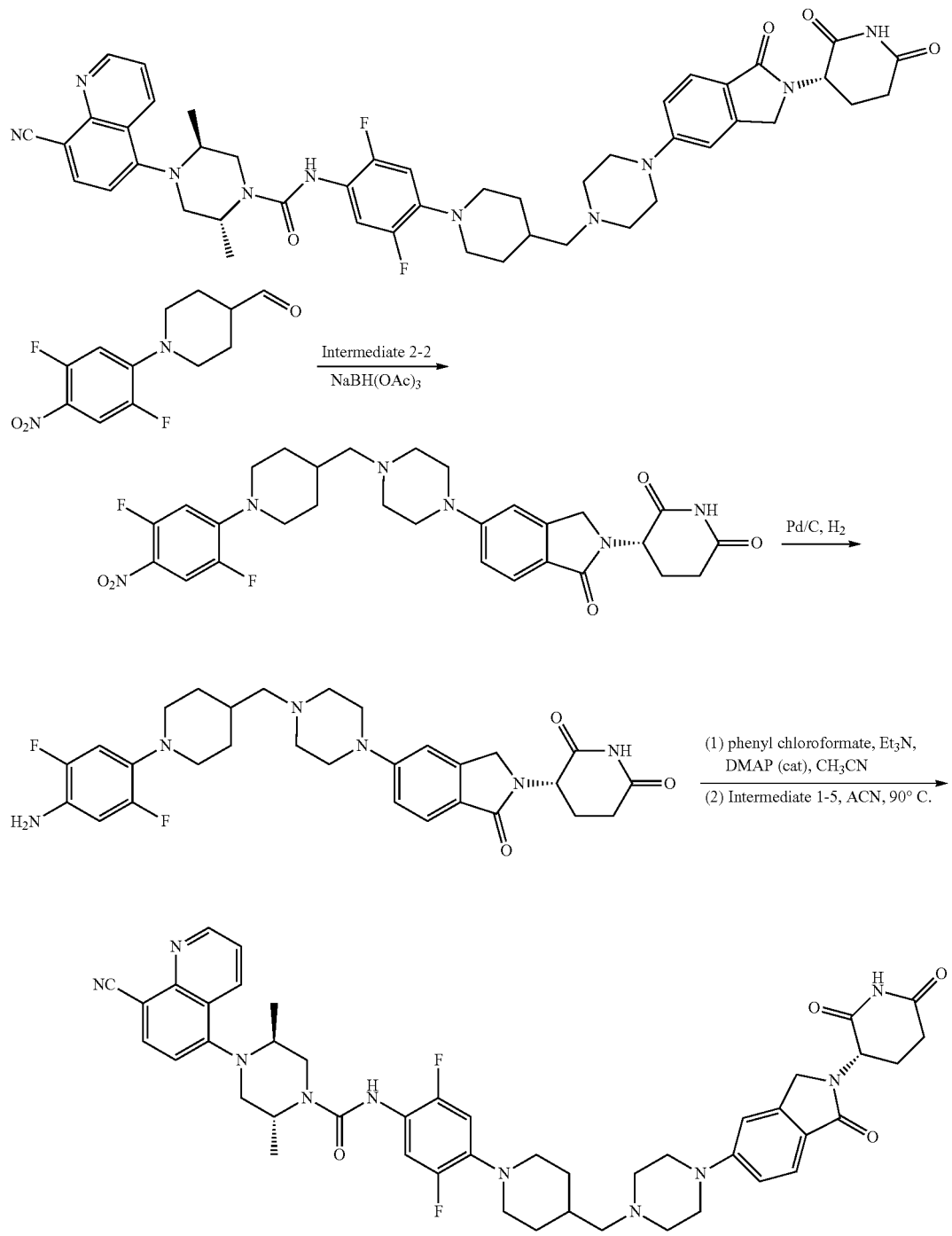
2-18

Step 1: Preparation of (S)-3-(5-(4-((1-(2,5-difluoro-4-nitrophenyl)piperidin-4-yl)methyl)piperazin-1-yl)-1-oxoisoindolin-2-yl)piperidine-2,6-dione To a solution containing 1-(2,5-difluoro-4-nitrophenyl)piperidine-4-carbaldehyde (90 mg, 0.33 mmol) and Intermediate 2-2 (162 mg, 0.33 mmol) in DCM (5 mL) stirred under nitrogen at room temperature was added magnesium sulphate (800 mg, 6.67 mmol) and triethylamine (67 mg, 0.67 mmol). The reaction mixture was stirred at room temperature for 1 hour. Then NaBH(OAc)$_3$ (177 mg, 0.83 mmol) was added in portions. The reaction was stirred for 1 hour. The solvent was removed in vacuum to give a crude product which was purified by silica gel column chromatography (0-15% MeOH in DCM) to give the title compound (200 mg, 100%). LC/MS: 582.6 [M+H]$^+$; $^1$H NMR (400 MHz, DMSO) δ 10.96 (s, 1H), 7.97 (dd, J=13.8, 7.4 Hz, 1H), 7.53 (d, J=8.7 Hz, 1H), 7.14-6.99 (m, 3H), 5.06 (dd, J=13.2, 5.1 Hz, 1H), 4.39-4.19 (m, 2H), 3.78 (d, J=12.6 Hz, 2H), 3.31-3.25 (m, 6H), 3.05-2.94 (m, 2H), 2.93-2.85 (m, 1H), 2.65-2.54 (m, 2H), 2.42-2.30 (m, 2H), 2.23 (d, J=6.5 Hz, 2H), 1.95 (dd, J=15.1, 9.9 Hz, 1H), 1.84 (d, J=10.2 Hz, 3H), 1.31-1.14 (m, 2H).

Step 2: Preparation of (S)-3-(5-(4-((1-(4-amino-2,5-difluorophenyl)piperidin-4-yl)methyl)piperazin-1-yl)-1-oxoisoindolin-2-yl)piperidine-2,6-dione To a solution of (S)-3-(5-(4-((1-(2,5-difluoro-4-nitrophenyl)piperidin-4-yl)methyl)piperazin-1-yl)-1-oxoisoindolin-2-yl)piperidine-2,6-dione (200 mg, 0.34 mmol) in THF (20 mL) was added Pd/C (35 mg) and stirred under H$_2$ at room temperature for 4 hours. The mixture was filtered, and the solvent was removed in vacuum to give the title compound (140 mg, 74%). LC/MS: 552.7 [M+H]$^+$.

Step 3: Preparation of (2R,5S)-4-(8-cyanoquinolin-5-yl)-N-(4-(4-((4-(2-((S)-2,6-dioxopiperidin-3-yl)-1-oxoisoindolin-5-yl)piperazin-1-yl)methyl)piperidin-1-yl)-2,5-difluorophenyl)-2,5-dimethylpiperazine-1-carboxamide (2-18)

To a solution containing (S)-3-(5-(4-((1-(4-amino-2,5-difluorophenyl)piperidin-4-yl)methyl)piperazin-1-yl)-1-oxoisoindolin-2-yl)piperidine-2,6-dione (140 mg, 0.25 mmol), phenyl chloroformate (58 mg, 0.37 mmol), and TEA (37 mg, 0.37 mmol) in ACN (2 mL) was added DMAP (3.6 mg, 0.03 mmol). The reaction mixture was stirred at room temperature for 2 hours. The reaction mixture was quenched by adding H$_2$O (2 mL). Solvent was removed under vacuum and the residue was dissolved in ACN (10 mL). Then 5-((2S,5R)-2,5-dimethylpiperazin-1-yl)quinoline-8-carbonitrile (Intermediate 1-5, 67 mg, 0.25 mmol) was added. The reaction mixture was stirred at 90° C. overnight. The mixture was concentrated in vacuum and the residue was purified by preparative TLC (MeOH:DCM=1:10) to give the title compound (31 mg, 15%). LC/MS: 844.5 [M+H]$^+$; $^1$H NMR (400 MHz, DMSO) δ 10.95 (s, 1H), 9.06 (dd, J=4.1, 1.3 Hz, 1H), 8.69 (d, J=8.6 Hz, 1H), 8.37-8.17 (m, 2H), 7.70 (dd, J=8.5, 4.2 Hz, 1H), 7.54 (d, J=8.4 Hz, 1H), 7.28-7.15 (m, 2H), 7.12-7.03 (m, 2H), 6.89 (dd, J=12.2, 8.2 Hz, 1H), 5.06 (dd, J=13.2, 5.0 Hz, 1H), 4.55 (br, 1H), 4.36 (d, J=16.5 Hz, 1H), 4.22 (d, J=16.5 Hz, 1H), 3.91 (m, 1H), 3.85 (br s, 2H), 3.75 (dd, J=12.1, 3.5 Hz, 1H), 3.36 (m, 3H), 3.31-3.22 (m, 3H), 2.97-2.85 (m, 2H), 2.74-2.60 (m, 3H), 2.58 (s, 3H), 2.43-2.32 (m, 2H), 2.25 (d, J=5.9 Hz, 2H), 2.02-1.93 (m, 1H), 1.83 (d, J=11.6 Hz, 2H), 1.70 (br, 1H), 1.35 (d, J=6.6 Hz, 3H), 1.30 (d, J=10.2 Hz, 2H), 0.90 (d, J=6.4 Hz, 3H).

Synthesis of (2R,5S)-4-(8-cyanoquinolin-5-yl)-N-(4-(4-((4-(2-(2,6-dioxopiperidin-3-yl)-1,3-dioxoisoindolin-5-yl)piperazin-1-yl)methyl)piperidin-1-yl)-2,5-difluorophenyl)-2,5-dimethylpiperazine-1-carboxamide (2-17)

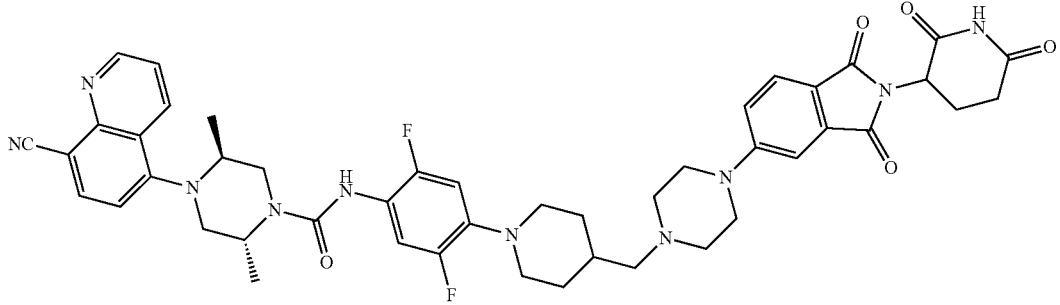 [SMILES: C[C@@H]1CN(c2ccc(C#N)c3ncccc23)[C@@H](C)CN1C(=O)Nc1cc(F)c(N2CCC(CN3CCN(c4ccc5c(c4)C(=O)N(C4CCC(=O)NC4=O)C5=O)CC3)CC2)cc1F]

This compound was prepared using the same method as for the preparation of 1-29 except Intermediate 1-5 was used in the final step of urea formation. LC/MS: 858.5 [M+H]$^+$; $^1$H NMR (400 MHz, DMSO) δ 11.08 (s, 1H), 9.06 (d, J=3.2 Hz, 1H), 8.69 (d, J=8.3 Hz, 1H), 8.37-8.18 (m, 2H), 7.70 (dd, J=8.4, 3.3 Hz, 2H), 7.35 (s, 1H), 7.30-7.16 (m, 3H), 6.89 (dd, J=12.1, 8.2 Hz, 1H), 5.13-5.03 (m, 1H), 4.56 (m, 1H), 3.95-3.80 (m, 3H), 3.75 (d, J=8.5 Hz, 1H), 3.46 (br s, 4H), 3.34 (m, 3H), 2.96-2.85 (dd, J=18.1, 8.5 Hz, 2H), 2.75-2.61 (m, 3H), 2.60-2.53 (m, 4H), 2.30-2.19 (m, 2H), 2.06-1.99 (m, 1H), 1.83 (d, J=11.8 Hz, 2H), 1.70 (brs, 1H), 1.35 (d, J=6.6 Hz, 3H), 1.30 (d, J=11.1 Hz, 2H), 0.94-0.86 (m, 3H).

Synthesis of (2R,5S)-4-(8-cyanoquinolin-5-yl)-N-(4-(4-((4-(2-(2,6-dioxopiperidin-3-yl)-1,3-dioxoisoindolin-5-yl)piperazin-1-yl)methyl)piperidin-1-yl)-3-fluorophenyl)-2,5-dimethylpiperazine-1-carboxamide (2-12)

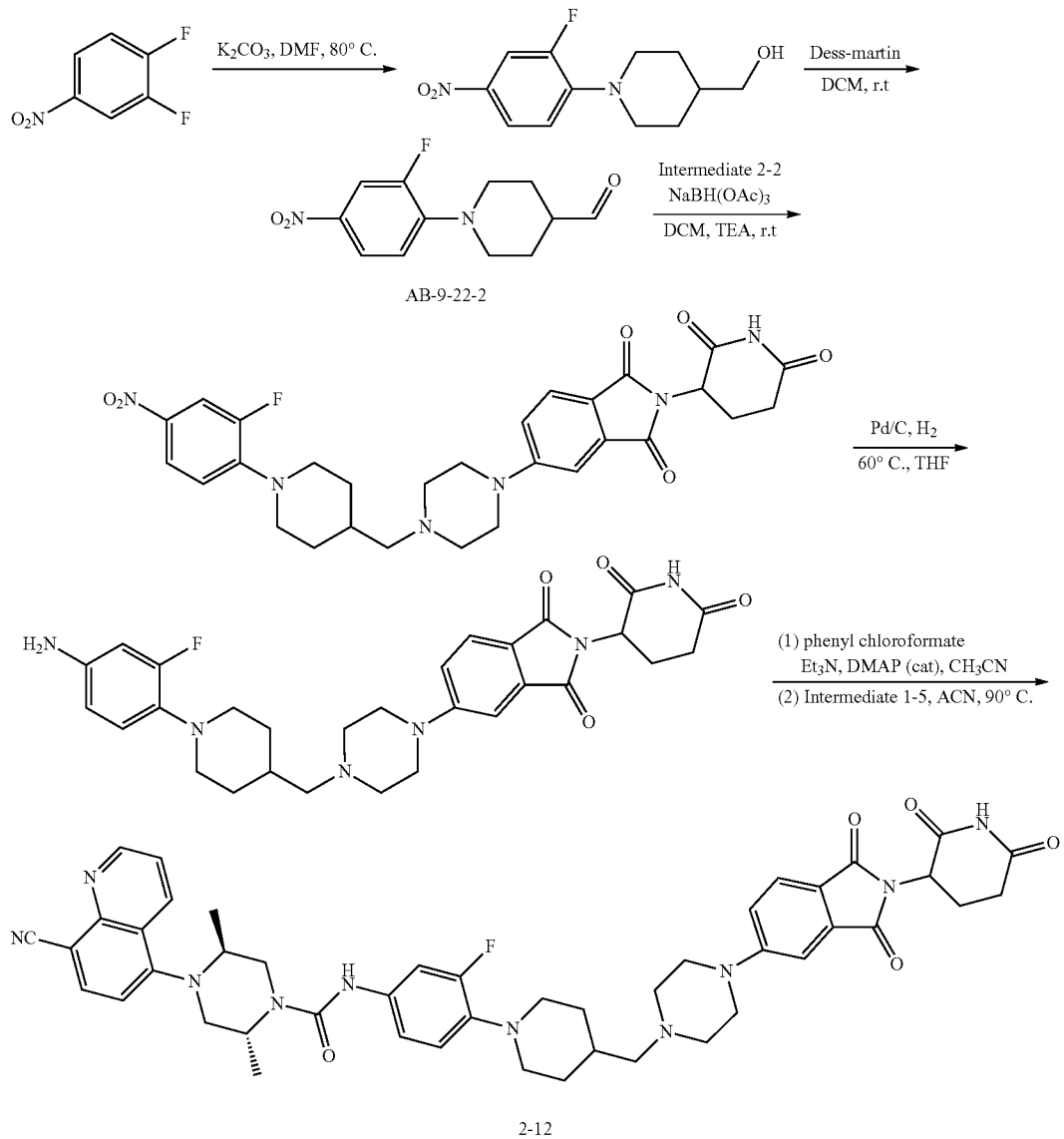

This compound was prepared using the same method in the preparation of 1-29. LC/MS: 840.4 [M+H]+; 1H NMR (400 MHz, DMSO) δ 11.10 (s, 1H), 9.06 (dd, J=4.2, 1.5 Hz, 1H), 8.69 (d, J=8.6 Hz, 1H), 8.59 (s, 1H), 8.28-8.23 (m, 1H), 7.70 (dd, J=8.6, 4.2 Hz, 2H), 7.48-7.15 (m, 5H), 6.99-6.92 (m, 1H), 5.11-5.06 (m, 1H), 4.58 (br, 1H), 3.95-3.71 (m, 5H), 3.46 (br s, 4H), 3.33-3.21 (m, 4H), 2.95-2.87 (m, 2H), 2.69-2.56 (m, 5H), 2.35-2.24 (m, 2H), 2.13-1.93 (m, 1H), 1.92-1.76 (m, 2H), 1.74-1.58 (m, 1H), 1.36-1.23 (m, 5H), 0.88 (d, J=6.5 Hz, 3H).

Testing of Compounds for AR Degradation Activity

LNCAP, VCAP and 22Rv1 cells were plated in 24-well plates at 1.5×10E5 cells/well in the RPMI growth medium containing 10% FBS and 1% Penicillin Streptomycin, and then incubated at 37° C. overnight. The following day, the test compound was administered to the cells by using 1000× compound stock solution prepared in DMSO at various concentrations. After administration of the compound, the cells were then incubated at 37° C. for 24 hours. Upon completion, the cells were washed with PBS and protein was collected in Laemmli sample buffer (1×; VWR International). Proteins in cell lysate were separated by SDS-PAGE and transferred to Odyssey nitrocellulose membranes (Licor) with iblot® dry blotting transfer system (ThermoFisher). Nonspecific binding was blocked by incubating membranes with Intercept Blocking Buffer (Licor) for 1 hour at room temperature with gentle shaking. The membranes were then incubated overnight at 4° C. with Primary antibodies rabbit anti-AR (1:1,000, Cell Signaling, 5153) and mouse anti-GAPDH (1:5,000, Santa Cruz Biotechnology, sc-47724) diluted in Intercept Blocking Buffer containing 0.1% Tween 20. After washing 3 times with TBS-T, the membranes were incubated with IRDye® 800CW goat anti-mouse IgG (1:20,000, Licor) or IRDye® 800CW goat anti-rabbit IgG (1:20,000, Licor) for 1 hour. After TBS-T washes, membranes were rinsed in TBS and scanned on Odyssey® CLx Imaging System (Licor). The bands were quantified using Image Studio™ Software (Licor).

Tables 5 and 6 summarize the androgen receptor (AR) degradative activity of exemplary compounds in LNCAP, VCAP and 22Rv1 cell lines 24 hours after administration. DC50: compound concentration needed for 50% target protein degradation.

TABLE 5

AR degradative activity of compounds from cellular assays (A: ≤10 nM; B: >100 nM, C: >10 nM and ≤100 nM)

| Compound | LNCAP (DC50, nM) | VCAP (DC50, nM) | 22RV1 (DC50, nM) |
|---|---|---|---|
| 1-20 | A | A | A |
| 1-13 | A | A | N/A |
| 1-21 | A | A | N/A |
| 1-31 | A | A | N/A |
| 1-14 | A | A | N/A |
| 1-26 | A | A | N/A |
| 1-22 | B | B | N/A |
| 1-30 | A | A | N/A |
| 1-29 | A | A | N/A |
| 1-27 | A | A | N/A |
| 1-28 | A | A | N/A |
| 1-43 | A | A | A |
| 1-19 | A | N/A | N/A |
| 1-44 | A | N/A | N/A |
| 1-33 | A | N/A | N/A |
| 1-45 | A | N/A | N/A |
| 1-46 | A | N/A | N/A |
| 1-47 | A | N/A | N/A |
| 1-48 | A | A | A |
| 1-53 | A | A | A |
| 1-49 | A | N/A | N/A |
| 1-50 | A | N/A | N/A |
| 1-52 | A | N/A | N/A |
| 1-41 | A | N/A | N/A |
| 1-39 | A | N/A | N/A |
| 1-54 | A | N/A | N/A |
| 1-51 | A | N/A | N/A |
| 1-23 | A | N/A | N/A |
| 1-25 | A | N/A | N/A |
| 1-11 | A | N/A | N/A |
| 1-9 | A | N/A | N/A |
| 1-12 | C | N/A | N/A |
| 1-10 | C | N/A | N/A |
| 1-8 | A | N/A | N/A |
| 1-55 | A | N/A | N/A |
| 1-56 | A | N/A | N/A |

TABLE 6

AR degradative activity of compounds from cellular assay (A: ≤10 nM; B: >100 nM, C: >10 nM and ≤100 nM)

| Compound | LNCAP (DC50, nM) | VCAP (DC50, nM) | 22RV1 (DC50, nM) |
|---|---|---|---|
| 2-18 | B | N/A | N/A |
| 2-17 | B | N/A | N/A |
| 2-12 | B | N/A | N/A |
| 2-21 | B | N/A | N/A |
| 2-10 | B | N/A | N/A |
| 2-11 | B | N/A | N/A |
| 2-9 | B | N/A | N/A |
| 2-8 | B | N/A | N/A |
| 2-22 | B | N/A | N/A |
| 2-24 | B | N/A | N/A |
| 2-15 | B | N/A | N/A |
| 2-23 | B | N/A | N/A |
| 2-16 | B | N/A | N/A |
| 2-13 | B | N/A | N/A |
| 2-14 | A | N/A | N/A |

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description or examples.

What is claimed is:

1. A compound of Formula 1 or a pharmaceutically acceptable salt thereof:

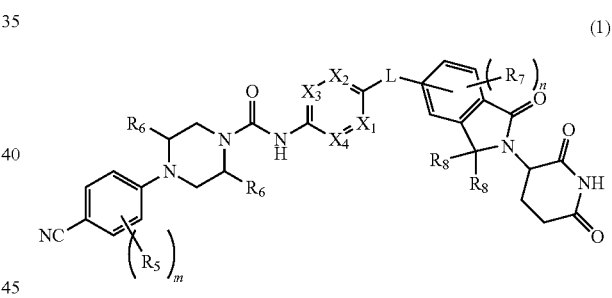

(1)

wherein:
$X_1$ is $CR_1$ or N;
$X_2$ is $CR_2$ or N;
$X_3$ is $CR_3$ or N;
$X_4$ is $CR_4$ or N;
each of $R_1$, $R_2$, $R_3$, and $R_4$ is independently selected from hydrogen, halogen, $C_1$-$C_3$alkoxy, and $C_1$-$C_3$haloalkyl, each of which is substituted with 0, 1, 2, or 3 Rs;
each $R_5$ is independently selected from halogen, hydroxyl, $C_1$-$C_3$alkyl, $C_1$-$C_3$alkoxy, $C_1$-$C_3$haloalkyl, —N($R_9$)$_2$, and —CN, each of which is substituted with 0, 1, 2, or 3 Rs;
each $R_6$ is independently selected from hydrogen, $C_1$-$C_3$alkyl, and $C_1$-$C_3$haloalkyl, each of which is substituted with 0, 1, 2, or 3 Rs;
each $R_7$ is independently selected from halogen, hydroxyl, $C_1$-$C_3$alkyl, $C_1$-$C_3$alkoxy, $C_1$-$C_3$haloalkyl, —N($R_9$)$_2$, and —CN, each of which is substituted with 0, 1, 2, or 3 Rs;
each $R_8$ is independently selected from hydrogen, hydroxyl, $C_1$-$C_3$alkyl, and $C_1$-$C_3$haloalkyl, each of which is substituted with 0, 1, 2, or 3 Rs, or two $R_8$ groups are taken together to form an oxo;

each $R_9$ is independently selected from hydrogen, $C_1$-$C_3$alkyl, —C(=O)—($C_1$-$C_3$alkyl), —C(=O)—O—($C_1$-$C_3$alkyl), and —C(=O)—NH—($C_1$-$C_3$alkyl), each of which is substituted with 0, 1, 2, or 3 Rs, or two $R_9$ groups are taken together to form a 3- to 6-membered heterocycle or heteroaryl;

each Rs is independently selected from halogen, hydroxyl, $C_1$-$C_3$alkyl, $C_1$-$C_3$alkoxy, $C_1$-$C_3$haloalkyl, —N($R_9$)$_2$, and —CN;

L is a linker of 1 to 16 carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 Rs;

m is 0, 1, 2, or 3; and n is 0, 1, 2, or 3, wherein each hydrogen atom is independently and optionally replaced by a deuterium atom.

2. The compound according to claim 1, wherein $X_1$ is $CR_1$, $X_2$ is $CR_2$, $X_3$ is $CR_3$, and $X_4$ is $CR_4$.

3. The compound according to claim 2, wherein $R_1$, $R_2$, $R_3$, and $R_4$ are each independently selected from H and F.

4. The compound according to claim 1, wherein each $R_5$ is independently selected from halogen, $C_1$-$C_3$alkoxy, and $C_1$-$C_3$haloalkyl.

5. The compound according to claim 1, wherein each $R_6$ is independently selected from H and $C_1$-$C_3$alkyl.

6. The compound according to claim 1, wherein each $R_8$ is hydrogen or two $R_8$ groups are taken together to form an oxo.

7. The compound according to claim 1, wherein L is a linker of 1 to 6 carbon atoms in length, wherein one or more carbon atoms are optionally replaced by C(=O), O, N($R_9$), S, $C_2$-alkenyl, $C_2$-alkynyl, cycloalkyl, aryl, heterocycle, or heteroaryl, wherein the $R_9$, $C_2$-alkenyl, cycloalkyl, aryl, heterocycle, and heteroaryl are each independently substituted with 0, 1, 2, or 3 Rs.

8. The compound according to claim 1, wherein L is selected from:

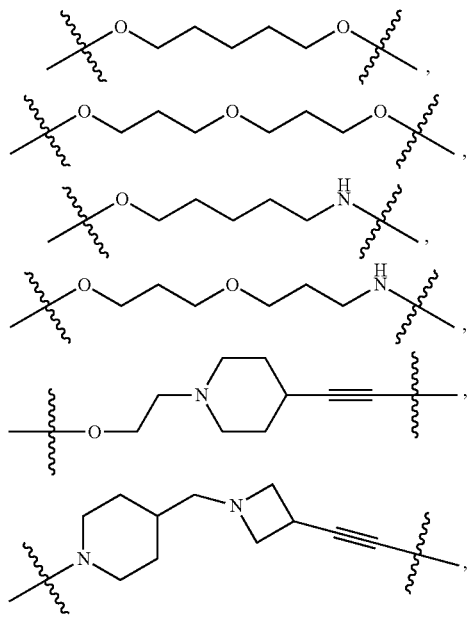

-continued

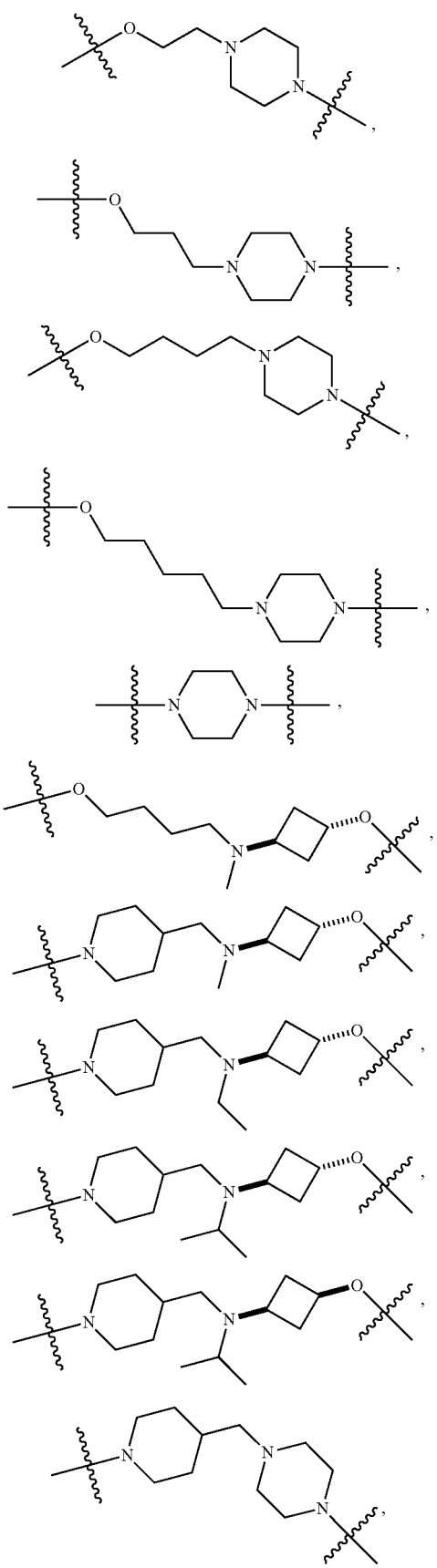

-continued

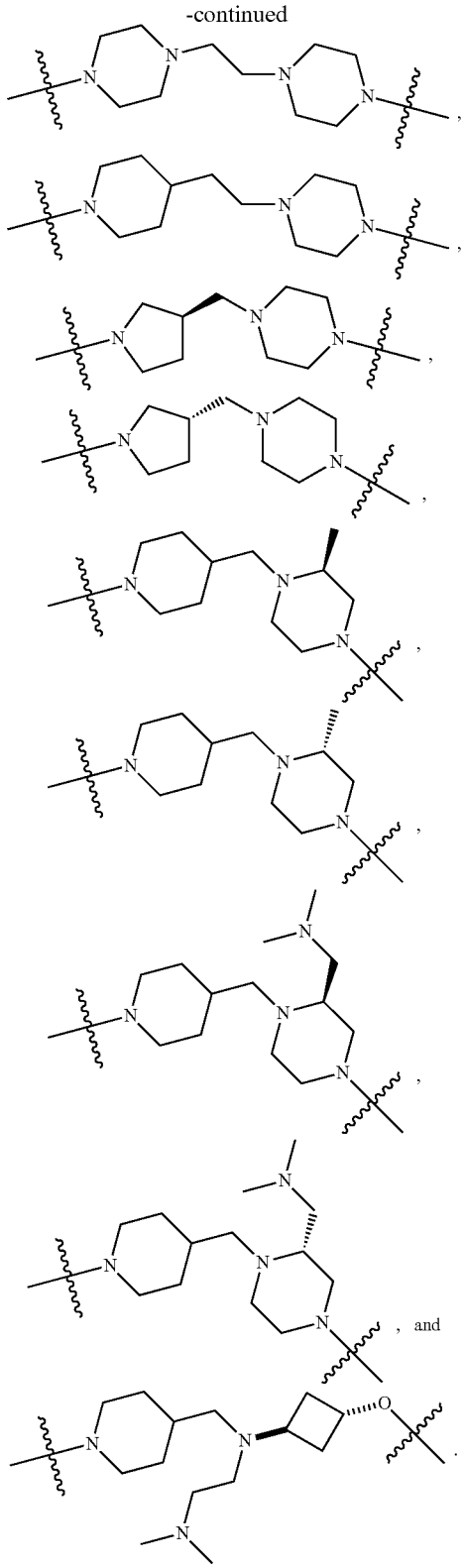

9. The compound according to claim 1, wherein the compound is chosen from:
(2R,5S)-4-(3-chloro-4-cyanophenyl)-N-(6-((5-((2-(2,6-dioxopiperidin-3-yl)-1,3-dioxoisoindolin-5-yl)oxy)pentyl)oxy)pyridin-3-yl)-2,5-dimethylpiperazine-1-carboxamide;

2R,5S)-4-(3-chloro-4-cyanophenyl)-N-(6-(3-(3-((2-(2,6-dioxopiperidin-3-yl)-1,3-dioxoisoindolin-5-yl)oxy)propoxy)propoxy)pyridin-3-yl)-2,5-dimethylpiperazine-1-carboxamide;
(2R,5S)-4-(3-chloro-4-cyanophenyl)-N-(6-(2-(4-(2-(2,6-dioxopiperidin-3-yl)-1,3-dioxoisoindolin-5-yl)piperazin-1-yl)ethoxy)pyridin-3-yl)-2,5-dimethylpiperazine-1-carboxamide;
(2R,5S)-4-(3-chloro-4-cyanophenyl)-N-(6-(3-(4-(2-(2,6-dioxopiperidin-3-yl)-1,3-dioxoisoindolin-5-yl)piperazin-1-yl)propoxy)pyridin-3-yl)-2,5-dimethylpiperazine-1-carboxamide;
(2R,5S)-4-(3-chloro-4-cyanophenyl)-N-(6-(4-(4-(2-(2,6-dioxopipendin-3-yl)-1,3-dioxoisoindolin-5yl)piperazin-1-yl)butoxy)pyridin-3-yl)-2,5-dimethylpiperazine-1-carboxamide;
(2R,5S)-4-(3-chloro-4-cyanophenyl)-N-(6-((5-(4-(2-(2,6-dioxopiperidin-3-yl)-1,3-dioxoisoindolin-5-yl)piperazin-1-yl)pentyl)oxy)pyridin-3-yl)-2,5-dimethylpiperazine-1-carboxamide;
(2R,5S)-4-(3-chloro-4-cyanophenyl)-N-(6-(4-(2-(2,6-dioxopiperidin-3-yl)-1,3-dioxoisoindolin-5-yl)piperazin-1-yl)pyridin-3-yl)-2,5-dimethylpiperazine-1-carboxamide;
(2R,5S)-4-(3-chloro-4-cyanophenyl)-N-(6-(4-(((1r,3r)-3-((2-(2,6-dioxopiperidin-3-yl)-1,3-dioxoisoindolin-5-yl)oxy)cyclobutyl)(methyl)amino)butoxy)pyridin-3-yl)-2,5-dimethylpiperazine-1-carboxamide;
(2R,5S)-4-(3-chloro-4-cyanophenyl)-N-(6-(4-((((1r,3r)-3-((2-(2,6-dioxopiperidin-3-yl)-1,3-dioxoisoindolin-5-yl)oxy)cyclobutyl)(methyl)amino)methyl)piperidin-1-yl)pyridin-3-yl)-2,5-dimethylpiperazine-1-carboxamide;
(2R,5S)-4-(3-chloro-4-cyanophenyl)-N-(6-(4-((((1r,3r)-3-((2-(2,6-dioxopiperidin-3-yl)-1,3-dioxoisoindolin-5-yl)oxy)cyclobutyl)(ethyl)amino)methyl)piperidin-1-yl)pyridin-3-yl)-2,5-dimethylpiperazine-1-carboxamide;
(2R,5S)-4-(3-chloro-4-cyanophenyl)-N-(6-(4-((((1r,3)-3-((2-(2,6-dioxopiperidin-3-yl)-1,3-dioxoisoindolin-5-yl)oxy)cyclobutyl)(isopropyl)amino)methyl)pipendin-1-yl)pyridin-3-yl)-2,5-dimethylpiperazine-1-carboxamide;
(2R,5S)-4-(3-chloro-4-cyanophenyl)-N-(6-(4-((((1s,3s)-3-((2-(2,6-dioxopiperidin-3-yl)-1,3-dioxoisoindolin-5-yl)oxy)cyclobutyl)(isopropyl)amino)methyl)piperidin-1-yl)pyridin-3-yl)-2,5-dimethylpiperazine-1-carboxamide;
(2R,5S)-4-(3-chloro-4-cyanophenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide;
(2R,5S)-4-(3-chloro-4-cyanophenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide;
4-(3-chloro-4-cyanophenyl)-N-(6-(4-((4-(2-(2,6-dioxopipendin-3-yl)-1,3-dioxoisoindolin-5-yl)piperazin-1-yl)methyl)piperidin-1-yl)pyridin-3-yl)-2-methylpiperazine-1-carboxamide;
(3S)-4-(3-chloro-4-cyanophenyl)-N-(6-(4-((4-(2-(2,6-dioxopipendin-3-yl)-1,3-dioxoisoindolin-5-yl)piperazin-1-yl)methyl)piperidin-1-yl)pyridin-3-yl)-3-methylpiperazine-1-carboxamide;
(3R)-4-(3-chloro-4-cyanophenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-3-methylpiperazine-1-carboxamide;

4-(3-chloro-4-cyanophenyl)-N-(6-(4-((4-(2-(2,6-dioxopipendin-3-yl)-1,3-dioxoisoindolin-5-yl)piperazin-1-yl)methyl)piperidin-1-yl)pyridin-3-yl)piperazine-1-carboxamide;

(2R,5S)-4-(3-chloro-4-cyanophenyl)-N-(6-(4-(2-(4-(2-(2,6-dioxopipendin-3-yl)-1,3-dioxoisoindolin-5-yl)piperazin-1-yl)ethyl)piperidin-1-yl)pyridin-3-yl)-2,5-dimethylpiperazine-1-carboxamide;

(2R,5S)-4-(3-chloro-4-cyanophenyl)-N-(2-(4-((4-(2-(2,6-dioxopipendin-3-yl)-1,3-dioxoisoindolin-5-yl)piperazin-1-yl)methyl)pipendin-1-yl)pyrimidin-5-yl)-2,5-dimethylpiperazine-1-carboxamide;

(2R,5S)-4-(3-chloro-4-cyanophenyl)-N-(2-(4-((4-(2-(2,6-dioxopipendin-3-yl)-1,3-dioxoisoindolin-5-yl)piperazin-1-yl)methyl)pipendin-1-yl)pyridin-5-yl)-2,5-dimethylpiperazine-1-carboxamide;

(2S,5R)-4-(3-chloro-4-cyanophenyl)-N-(2-(4-((4-(2-(2,6-dioxopiperidin-3-yl)-1,3-dioxoisoindolin-5-yl)piperazin-1-yl)methyl)pipendin-1-yl)pyrimidin-5-yl)-2,5-dimethylpiperazine-1-carboxamide;

(2R,5S)-4-(3-chloro-4-cyanophenyl)-N-(4-(4-((4-(2-(2,6-dioxopiperidin-3-yl)-1,3-dioxoisoindolin-5-yl)piperazin-1-yl)methyl)pipendin-1-yl)-2-fluorophenyl)-2,5-dimethylpiperazine-1-carboxamide;

(2R,5S)-4-(3-chloro-4-cyanophenyl)-N-(4-(4-((4-(2-(2,6-dioxopipendin-3-yl)-1,3-dioxoisoindolin-5-yl)piperazin-1-yl)methyl)pipendin-1-yl)-2,6-difluorophenyl)-2,5-dimethylpiperazine-1-carboxamide;

(2R,5S)-4-(4-cyano-3-methoxyphenyl)-N-(4-(4-((4-(2-(2,6-dioxopipendin-3-yl)-1,3-dioxoisoindolin-5-yl)piperazin-1-yl)methyl)pipendin-1-yl)-2-fluorophenyl)-2,5-dimethylpiperazine-1-carboxamide;

(2R,5S)-4-(4-cyano-3-methoxyphenyl)-N-(6-(4-((4-(2-(2,6-dioxopipendin-3-yl)-1,3-dioxoisoindolin-5-yl)piperazin-1-yl)methyl)pipendin-1-yl)pyridin-3-yl)-2,5-dimethylpiperazine-1-carboxamide;

(2R,5S)-4-(4-cyano-3-methoxyphenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide;

(2R,5S)-4-(4-cyano-3-methoxyphenyl)-N-(2-(4-(2-(4-(2-(2,6-dioxopiperidin-3-yl)-1,3-dioxoisoindolin-5-yl)piperazin-1-yl)ethyl)piperidin-1-yl)pyrimidin-5-yl)-2,5-dimethylpiperazine-1-carboxamide (2R,5S)-4-(4-cyano-3-methoxyphenyl)-N-(4-(4-((4-(2-(2,6-dioxopiperidin-3-yl)-1,3-dioxoisoindolin-5-yl)piperazin-1-yl)methyl)piperidin-1-yl)-2,5-difluorophenyl)-2,5-dimethylpiperazine-1-carboxamide;

(2R,5S)-4-(4-cyano-3-(trifluoromethyl)phenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide;

(2R,5S)-4-(4-cyano-3-(trifluoromethyl)phenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide;

(2R,5S)-4-(4-cyano-3-(trifluoromethyl)phenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide;

(2R,5S)-4-(4-cyano-3-methoxyphenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide;

(2R,5S)-4-(4-cyano-3-methoxyphenyl)-N-(4-(4-((4-(2-((S)-2,6-dioxopiperidin-3-yl)-1-oxoisoindolin-5-yl)piperazin-1-yl)methyl)piperidin-1-yl)-2,5-difluorophenyl)-2,5-dimethylpiperazine-1-carboxamide;

(2R,5S)-4-(3-chloro-4-cyanophenyl)-N-(4-(4-((4-(2-((S)-2,6-dioxopiperidin-3-yl)-1-oxoisoindolin-5-yl)piperazin-1-yl)methyl)piperidin-1-yl)-2,5-difluorophenyl)-2,5-dimethylpiperazine-1-carboxamide;

(2R,5S)-4-(4-cyano-3-fluoro-5-methoxyphenyl)-N-(6-(4-((4-(2-(2,6-dioxopiperidin-3-yl)-1,3-dioxoisoindolin-5-yl)piperazin-1-yl)methyl)piperidin-1-yl)pyridin-3-yl)-2,5-dimethylpiperazine-1-carboxamide;

(2R,5S)-4-(4-cyano-3-fluoro-5-methoxyphenyl)-N-(2-(4-((4-(2-(2,6-dioxopiperidin-3-yl)-1,3-dioxoisoindolin-5-yl)piperazin-1-yl)methyl)piperidin-1-yl)pyrimidin-5-yl)-2,5-dimethylpiperazine-1-carboxamide;

(2R,5S)-4-(4-cyano-3-fluoro-5-methoxyphenyl)-N-(4-(4-((4-(2-(2,6-dioxopiperidin-3-yl)-1,3-dioxoisoindolin-5-yl)piperazin-1-yl)methyl)piperidin-1-yl)-2,5-difluorophenyl)-2,5-dimethylpiperazine-1-carboxamide;

(2R,5S)-4-(4-cyano-3-methoxyphenyl)-N-(6-(4-((4-(2-(2,6-dioxopiperidin-3-yl)-6-fluoro-1,3-dioxoisoindolin-5-yl)piperazin-1-yl)methyl)piperidin-1-yl)pyridin-3-yl)-2,5-dimethylpiperazine-1-carboxamide;

(2R,5S)-4-(4-cyano-3-methoxyphenyl)-N-(6-(4-((4-(2-((S)-2,6-dioxopiperidin-3-yl)-6-fluoro-1-oxoisoindolin-5-yl)piperazin-1-yl)methyl)piperidin-1-yl)pyridin-3-yl)-2,5-dimethylpiperazine-1-carboxamide;

(2R,5S)-4-(3-chloro-4-cyanophenyl)-N-(2-(4-((4-(2-(2,6-dioxopiperidin-3-yl)-6-fluoro-1,3-dioxoisoindolin-5-yl)piperazin-1-yl)methyl)piperidin-1-yl)pyrimidin-5-yl)-2,5-dimethylpiperazine-1-carboxamide;

(2R,5S)-4-(3-chloro-4-cyanophenyl)-N-(2-(4-((4-(2-((S)-2,6-dioxopiperidin-3-yl)-6-fluoro-1-oxoisoindolin-5-yl)piperazin-1-yl)methyl)piperidin-1-yl)pyrimidin-5-yl)-2,5-dimethylpiperazine-1-carboxamide;

(2R,5S)-4-(4-cyano-3-(trifluoromethyl)phenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide;

(2R,5S)-4-(3-chloro-4-cyanophenyl)-N-(6-(4-((4-(2-((S)-2,6-dioxopiperidin-3-yl)-1-oxoisoindolin-5-yl)piperazin-1-yl)methyl)piperidin-1-yl)pyridin-3-yl)-2,5-dimethylpiperazine-1-carboxamide;

(2R,5S)-4-(4-cyano-3-(trifluoromethyl)phenyl)-N-(4-(4-((4-(2-(2,6-dioxopiperidin-3-yl)-1,3-dioxoisoindolin-5-yl)piperazin-1-yl)methyl)piperidin-1-yl)-3-fluorophenyl)-2,5-dimethylpiperazine-1-carboxamide;

(2R,5S)-4-(3-chloro-4-cyanophenyl)-N-(4-(4-((4-(2-((S)-2,6-dioxopiperidin-3-yl)-1-oxoisoindolin-5-yl)piperazin-1-yl)methyl)piperidin-1-yl)-3-fluorophenyl)-2,5-dimethylpiperazine-1-carboxamide;

(2R,5S)-4-(3-chloro-4-cyanophenyl)-N-(4-(4-((4-(2-(2,6-dioxopiperidin-3-yl)-1,3-dioxoisoindolin-5-yl)piperazin-1-yl)methyl)piperidin-1-yl)-3-fluorophenyl)-2,5-dimethylpiperazine-1-carboxamide;

(2R,5S)-4-(4-cyano-3-methoxyphenyl)-N-(4-(4-((4-(2-(2,6-dioxopiperidin-3-yl)-1,3-dioxoisoindolin-5-yl)piperazin-1-yl)methyl)piperidin-1-yl)-3-fluorophenyl)-2,5-dimethylpiperazine-1-carboxamide;

(2R,5S)-4-(4-cyano-3-(trifluoromethyl)phenyl)-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide;

(2R,5S)-4-(4-cyano-3-(trifluoromethyl)phenyl)-N-(4-(4-((4-(2-((S)-2,6-dioxopiperidin-3-yl)-1-oxoisoindolin-5-yl)piperazin-1-yl)methyl)piperidin-1-yl)-3-fluorophenyl)-2,5-dimethylpiperazine-1-carboxamide;

(2R,5S)-4-(3-chloro-4-cyanophenyl)-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide;

(2R,5S)-4-(4-cyano-3-methoxyphenyl)-N-(2-(4-((4-(2-((S)-2,6-dioxopiperidin-3-yl)-1-oxoisoindolin-5-yl)piperazin-1-yl)methyl)piperidin-1-yl)pyrimidin-5-yl)-2,5-dimethylpiperazine-1-carboxamide;

(2R,5S)-4-(4-cyano-3-methoxyphenyl)-N-(4-(4-((4-(2-((S)-2,6-dioxopiperidin-3-yl)-1-oxoisoindolin-5-yl)piperazin-1-yl)methyl)piperidin-1-yl)-3-fluorophenyl)-2,5-dimethylpiperazine-1-carboxamide;

(2R,5S)-4-(3-chloro-4-cyanophenyl)-N-(6-(4-((4-(2-(2,6-dioxopiperidin-3-yl)-6-fluoro-1,3-dioxoisoindolin-5-yl)piperazin-1-yl)methyl)piperidin-1-yl)pyridin-3-yl)-2,5-dimethylpiperazine-1-carboxamide;

(2R,5S)-4-(4-cyano-3-methoxyphenyl)-N-(4-(4-((4-(2-((S)-2,6-dioxopiperidin-3-yl)-6-fluoro-1-oxoisoindolin-5-yl)piperazin-1-yl)methyl)piperidin-1-yl)-3-fluorophenyl)-2,5-dimethylpiperazine-1-carboxamide;

(2R,5S)-4-(3-chloro-4-cyanophenyl)-N-(4-(4-((4-(2-((S)-2,6-dioxopiperidin-3-yl)-6-fluoro-1-oxoisoindolin-5-yl)piperazin-1-yl)methyl)piperidin-1-yl)-3-fluorophenyl)-2,5-dimethylpiperazine-1-carboxamide;

or a pharmaceutically salt thereof, wherein each hydrogen atom is independently and optionally replaced by a deuterium atom.

10. A pharmaceutical composition comprising at least one compound or pharmaceutically acceptable salt thereof according to claim 1 and a pharmaceutically acceptable carrier.

* * * * *

UNITED STATES PATENT AND TRADEMARK OFFICE
CERTIFICATE OF CORRECTION

PATENT NO. : 11,220,490 B2
APPLICATION NO. : 17/331015
DATED : January 11, 2022
INVENTOR(S) : Jie Fan et al.

It is certified that error appears in the above-identified patent and that said Letters Patent is hereby corrected as shown below:

In the Claims

In Claim 1, Column 171, Line 9, "$C_1$i-C3" should read --$C_1$-$C_3$--.

In Claim 9, Column 174, Lines 5-8, "(2R,5S)-4-(3-chloro-4-cyanophenyl)-N-(6-(2-(4-(2-(2,6-dioxopiperidin-3-yl)-1,3-dioxoisoindolin-5-yl)piperazin-$_1$-yl)ethoxy)pyridin-3-yl)-2,5-dimethylpiperazine-1-carboxamide" should read --(2R,5S)-4-(3-chloro-4-cyanophenyl)-N-(6-(2-(4-(2-(2,6-dioxopiperidin-3-yl)-1,3-dioxoisoindolin-5-yl)piperazin-1-yl)ethoxy)pyridin-3-yl)-2,5-dimethylpiperazine-1-carboxamide--.

In Claim 9, Column 174, Lines 38-42, "(2R,5S)-4-(3-chloro-4-cyanophenyl)-N-(6-(4-(((1r,3)-3-((2-(2,6-dioxopiperidin-3-yl)-1,3-dioxoisoindolin-5-yl)oxy)cyclobutyl)(isopropyl)amino)methyl)pipendin-1-yl)pyridin-3-yl)-2,5-dimethylpiperazine-1-carboxamide;" should read --(2R,5S)-4-(3-chloro-4-cyanophenyl)-N-(6-(4-(((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyridin-3-yl)-2,5-dimethylpiperazine-1-carboxamide;--.

Signed and Sealed this
Fifth Day of July, 2022

Katherine Kelly Vidal
*Director of the United States Patent and Trademark Office*